United States Patent [19]

Osugi et al.

[11] Patent Number: 4,684,664

[45] Date of Patent: Aug. 4, 1987

[54] DERIVATIVES OF β-(4-ISOCYANO-1,2,3,4-DIEPOXYCYCLO-PENTYL) ACRYLIC ACID

[75] Inventors: Katsuhisa Osugi; Isao Ichinose; Eisaku Takahashi; Masato Arahira, all of Iwaki, Japan

[73] Assignee: Kureha Kagaku Kogyo Kabushiki Kaisha, Tokyo, Japan

[21] Appl. No.: 692,104

[22] Filed: Jan. 16, 1985

[30] Foreign Application Priority Data

Jan. 23, 1984 [JP] Japan .................................. 59-9876
Jan. 23, 1984 [JP] Japan .................................. 59-9877

[51] Int. Cl.$^4$ .................. A61K 31/335; A61K 31/43; C07D 499/32; C07D 265/30; C07D 405/14; C07D 303/06
[52] U.S. Cl. .................................. 514/475; 514/196; 514/234; 514/255; 514/338; 514/362; 514/370; 514/422; 514/464; 540/217; 540/228; 540/329; 544/176; 544/375; 544/378; 546/270; 548/525; 549/332; 549/365; 549/545
[58] Field of Search .................... 260/239.1; 548/525, 548/526; 544/22, 176, 375, 378; 546/270; 536/16.8, 22; 549/332, 545, 365; 514/42, 196, 202, 255, 234, 338, 362, 365, 383, 475, 370, 464; 540/217, 228, 329

[56] References Cited

U.S. PATENT DOCUMENTS 4,360,685 11/1982 Haslanger et al. .................. 549/386
4,542,154 9/1985 Ohsugi et al. ...................... 514/475

OTHER PUBLICATIONS

Fujiwara et al: "Fermentation, Isolation and Characterization of Isonitrile Antibiotics", Agric. Biol. Chem., 46(7), 1803–1809, 1982.
Brewer et al: "Ovine Ill-Thrift in Nova Scotia, 9, Production of Experimental Quantities of Isocyanide Metabolites of *Trichoderma Hamatum*, Can. J. Microbiol., vol. 28, pp. 1252–1260, 1982.

*Primary Examiner*—Werren B. Lone
*Assistant Examiner*—Vera C. Clarke
*Attorney, Agent, or Firm*—Cushman, Darby & Cushman

[57] ABSTRACT

Disclosed herein are derivatives of β-(4-isocyano-1,2,3,4-diepoxycyclopentyl)acrylic acid, the derivatives showing an antibacterial activity, an antifungal activity and an antimycoplasmal activity.

8 Claims, 157 Drawing Figures

DERIVATIVES OF β-(4-ISOCYANO-1,2,3,4-DIEPOXYCYCLOPENTYL) ACRYLIC ACID

BACKGROUND OF THE INVENTION

The present invention relates to a derivative of β-(4-isocyano-1,2,3,4-diepoxycyclopentyl)acrylic acid represented by the formula:

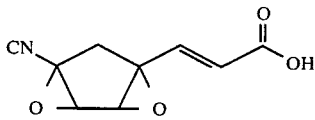

and more in detail, the present invention relates to a derivative of the β-substituted acrylic acid, the derivative being represented by the formula (I):

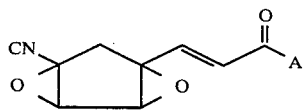 (I)

wherein A represents
(1) —OR, wherein R is a residual group of an ester or

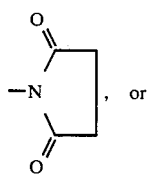, or

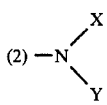

wherein X and Y may be the same or different from each other and represent respectively a hydrogen atom or a group bonded to N, or X and Y may form a ring together with N. In the case where A represents

in the formula (I),

includes not only a group —NH$_2$ but also an amino group having various substituting groups and a heterocyclic group including N, and in the case where A represents —OR in the formula (I), the R is a residual group of an ester, having various groups other than an alkyl group.

Previously, the present inventors found a new antibiotic substance, β-(4-isocyano-1,2-3,4-diepoxycyclopentyl)acrylic acid (hereinafter referred to as the β-substituted acrylic acid) in a cultured product of "No. 2188 production strain" (deposition number of the Fermentation Research Institute of Japanese Government: FERM P-142) of a mold belonging to Penicillium, producing an antibiotic substance, which had been isolated from soil. The antibiotic substance is disclosed in Japanese Patent Applications Laying-Open No. 59-17989 and No. 59-25398.

Thereafter, as a result of the present inventors' studies on the pharmaceutically improved derivatives of the β-substituted acrylic acid, the present inventors have found that the esters of β-substituted acrylic acid, a hydroxysuccinimide-derivative of β-substituted acrylic acid and the acid amide of β-substituted acrylic acid show antibacterial activity, antifungal activity and antimycoplasmal activity and have attained the present invention.

SUMMARY OF THE INVENTION

In a first aspect of the present invention, there is provided a derivative of β-(4-isocyano-1,2-3,4-diepoxycyclopentyl)acrylic acid represented by the formula (I):

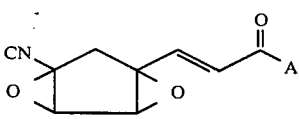 (I)

wherein A represents
(1) —OR wherein R represents a residual group of an ester or

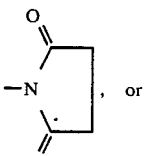, or

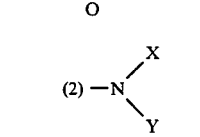

wherein X and Y may be the same or different from each other and represent respectively a hydrogen atom or a group bonded to N, or X and Y may form a ring together with N.

In a second aspect of the present invention, there is provided a pharmaceutical composition having antibacterial activity, antifungal activity and antimycoplasmal activity in dosage unit form which comprises a dosage effective to produce the activities of a derivative of β-(4-isocyano-1,2-3,4-diepoxycyclopentyl)acrylic acid represented by the formula (I):

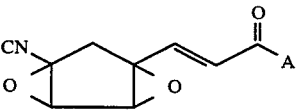 (I)

wherein A represents
(1) —OR wherein R represents a residual group of an ester or

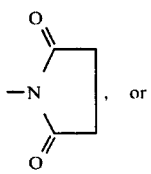, or (2) 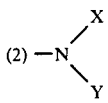

wherein X and Y may be the same or different from each other and represent respectively a hydrogen atom or a group bonded to N, or X and Y may form a ring together with N.

BRIEF EXPLANATION OF DRAWINGS

Of the attached drawings.

DETAILED DESCRIPTION OF THE INVENTION

Figure 1:
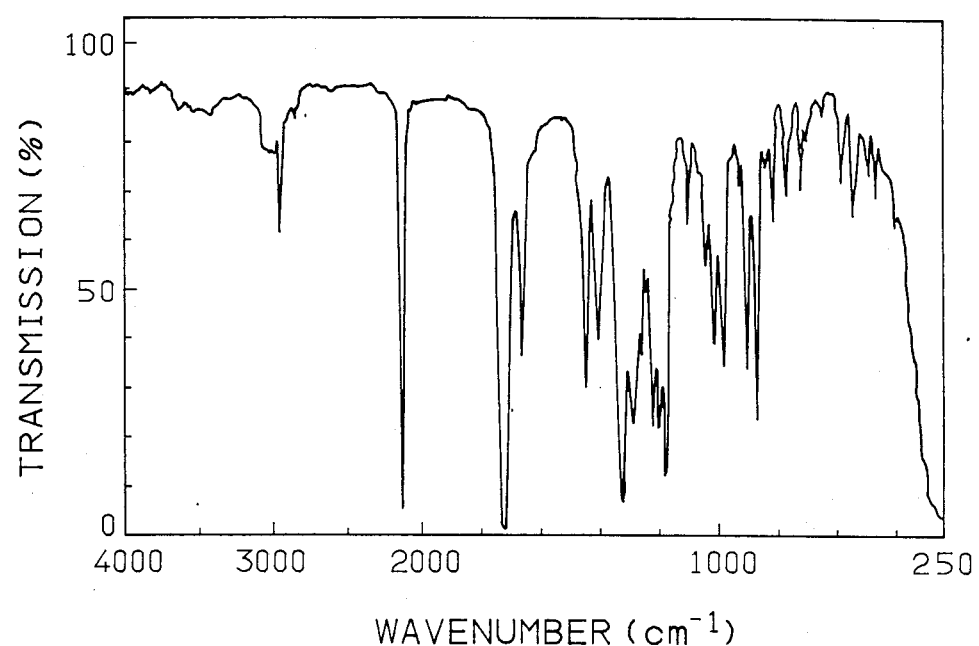
FIGS 1 to 74 are the respective infrared absorption spectra of the derivative of β-substituted acrylic acid Nos. 1 to 72.

The novel derivative of β-substituted acrylic acid according to the present invention includes esters of the β-substituted acrylic acid, hydroxysuccinimide-derivatives of the β-substituted acrylic acid and the β-substituted acrylamide. The derivative is represented by the formula (I):

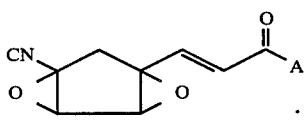 (I)

wherein A represents (1) —OR wherein R represents a residual group of an ester or

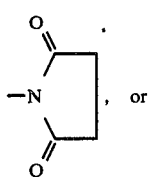, or (2) 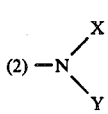

wherein X and Y may be the same or different from each other and represent respectively a hydrogen atom or a group bonding to N, or X and Y may form a ring together with N.

In the case where A of the formula (I) is the —OR, as R, an alkyl group of 1 to 4 carbon atoms, namely methyl group, ethyl group, propyl group, iso-propyl group, butyl group, iso-butyl group and t-butyl group may be mentioned, and various substituted alkyl groups may be mentioned. As the substituted alkyl group, those represented by the formula:

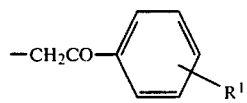

wherein $R^1$ represents a hydrogen atom, a chlorine atom, a bromine atom, a methyl group, a methoxy group or a nitro group, may be mentioned.

The residual group of the ester includes the non-substituted and substituted benzyl groups represented by the formula:

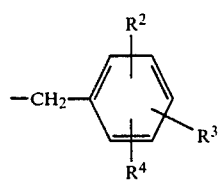

wherein $R^2$, $R^3$ and $R^4$ may be the same or different from each other and respectively represent a hydrogen atom, a methyl group, a methoxy group, a nitro group or a hydroxy group.

Furthermore, R may be

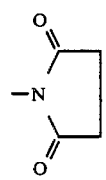

In the case where A in the formula (I) is

the group includes not only an amino group but also substituted amino groups and heterocyclic groups containing N thereof. The heterocyclic group containing N includes those having substituent(s). As such a heterocyclic group,

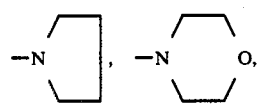

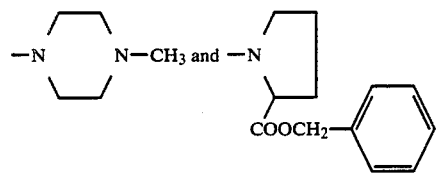

may be mentioned.

In the case where X and Y are the same or different from each other and represent respectively a hydrogen atom or a group bonded to N, as

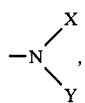

an amino group or a mono-substituted amino group or disubstituted amino group may be mentioned.

As examples of disubstituted amino groups,

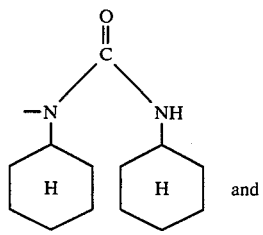

and

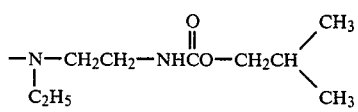

may be mentioned.

Those of monosubstituted amino group are represented by the formula —NHR$^5$, and as R$^5$, a cyclohexyl group, phenyl group, substituted phenyl group, benzyl group, 2-hydroxyethyl group, methoxy group, benzyloxy group, 4-pyridyl group,

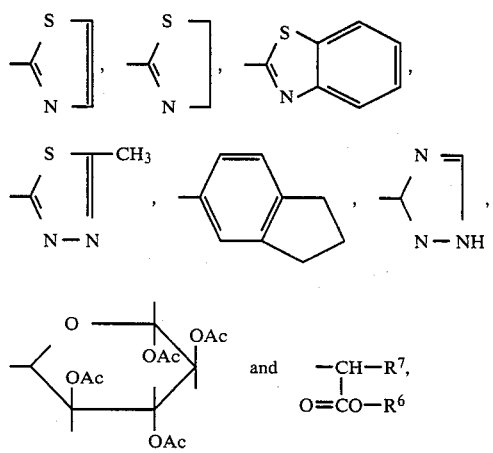

wherein R$^6$ represents a methyl group or benzyl group and R$^7$ represents a 2-methoxycarbonylethyl group, 2-benzyloxycarbonylethyl group, methoxycarbonylmethyl group, benzyloxycarbonylmethyl group, isopropyl group or benzyl group may be mentioned.

In addition, in the case where R$^5$ represents a substituted phenyl group, as R$^5$, a methylphenyl group, fluorophenyl group, chlorophenyl group, bromophenyl group, iodophenyl group, 3-trifluoromethylphenyl group, 4-trifluoromethylphenyl group, 3-nitrophenyl group, 3-methoxycarbonylphenyl group, 4-methoxycarbonylphenyl group, 3-carboxyphenyl group, 4-carboxyphenyl group, methoxyphenyl group, hydroxyphenyl group, aminophenyl group, 2-carbamoylphenyl group, 4-sulfamidophenyl group, 4-propoxyphenyl group, 4-isopropoxyphenyl group, 4-methylthiophenyl group, 2-methoxy-5-methoxycarbonylphenyl group, 4-benzoylphenyl group, 4-acetylphenyl group and

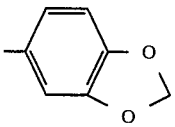

may be mentioned.

Furthermore, as an example of the groups represented by the formula —NHR$^5$, a group derived from other antibiotic substances such as

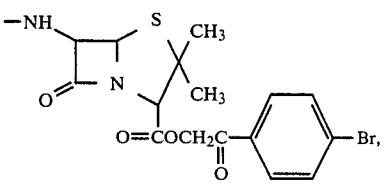

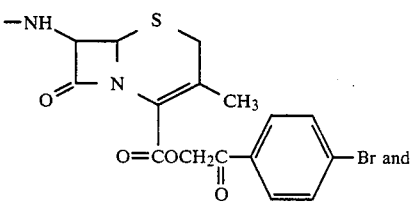

and

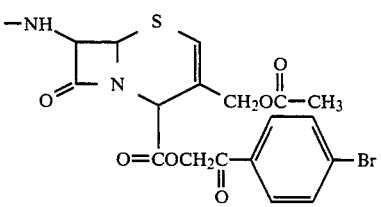

may also be mentioned.

It will be easily understood for the person skilled in the art that any one of the conventional and known processes can be applied in the case of producing one of the compounds of the present invention. For instance, in order to produce an ester of the β-substituted acrylic acid, an alcohol or a halide, for example, ethanol, p-bromophenacyl bromide, etc. is added to a solution of β-substituted acrylic acid in methylene chloride, and then reacted in the presence of an organic base such as triethylamine, 4-dimethylaminopyridine, 1,8-diazabicyclo-[5,4,0]-7-undecene, etc. at a boiling point of the mixture or a temperature of lower than the boiling point thereof.

A derivative of succinimido-derivative may be prepared by using N-hydroxysuccinimide and dicyclohexylcarbodiimide for preparing the ester derivative.

In order to prepare β-substituted acrylamide, any one of the known processes may be applied. For instance, after adding triethylamine into a solution of the β-substituted acrylic acid in methylene chloride, isobutyl chloroformate is added to the mixture to obtain a mixed acid anhydride. By reacting an amine compound having a group to be introduced with the thus obtained acid anhydride, the object acidamide is obtained. In another process, a solution of dicyclohexylcarbodiimide in methylene chloride was added dropwise to a solution of the β-substituted acrylic acid in methylene chloride at room temperature, and by adding a solution of an amine compound having the group to be introduced in methylene chloride to the mixture, the resultant mixture is reacted to obtain the objective substance.

For separating the objective substance from the reaction mixture and purifying the objective substance, chromatography on silica gel is advantageously utilizable regardless of the chemical structure of the objective substance.

The concrete embodiments of the derivative of β-substituted acrylic acid, according to the present invention (hereinafter referred to as the present compound) are shown in Table 1. The results of determination of the antibacterial activity, antifungal activity and antimycoplasmal activity of the present compound are shown in Table 2 as compared to those of β-substituted acrylic acid. The method for determining the respective activities are as follows.

(1) Antibacterial activity and antifungal activity:

Agar-dilution method was used for determination of the antibacterial activity and antifungal activity while using bouillon-agar culture medium, and the minimum inhibitory concentration of the specimen was expressed by μg/ml of the culture medium.

(2) Antimycoplasmal activity:

*Mycoplasma pneumoniae* IID817 was used as the test microorganism in a culture medium prepared by adding 1% of glucose to "PPLO broth (manufactured by Difco Co.) liquid culture medium" at 37° C. with phenol red as an indicator, thereby culturing the test microorganism. In control test where any antimycoplasmal substance is added to the culture medium, the culture medium became acidic by the proliferation of the mycoplasma, thereby the colour of phenol red was changed, and in the case of the actual test, the minimum concentration of the specimen in the culture medium which inhibited the colour change of phenol red, namely, inhibited the proliferation of the mycoplasm, was adopted as the minimum inhibitory concentration (MIC).

The name of the microorganism tested in the above-mentioned tests are shown in Table 2.

TABLE 1

[Structure shown at top of table:]

A cyclic compound with CN and two O atoms in the ring, substituted with -CH=CH-C(=O)-A group

Figure 2:
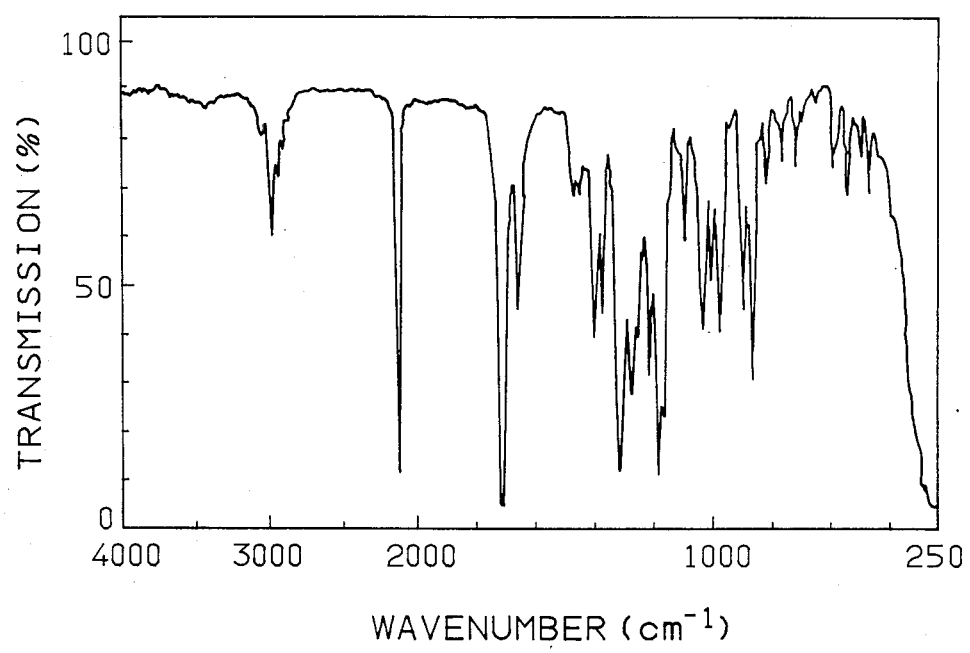
Figure 3:
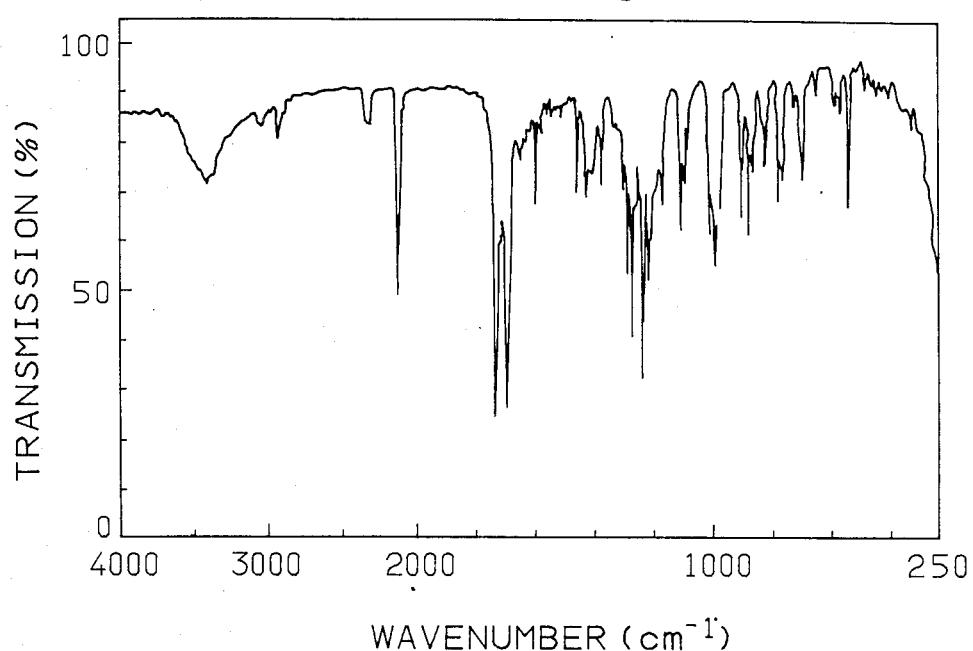
Figure 5:
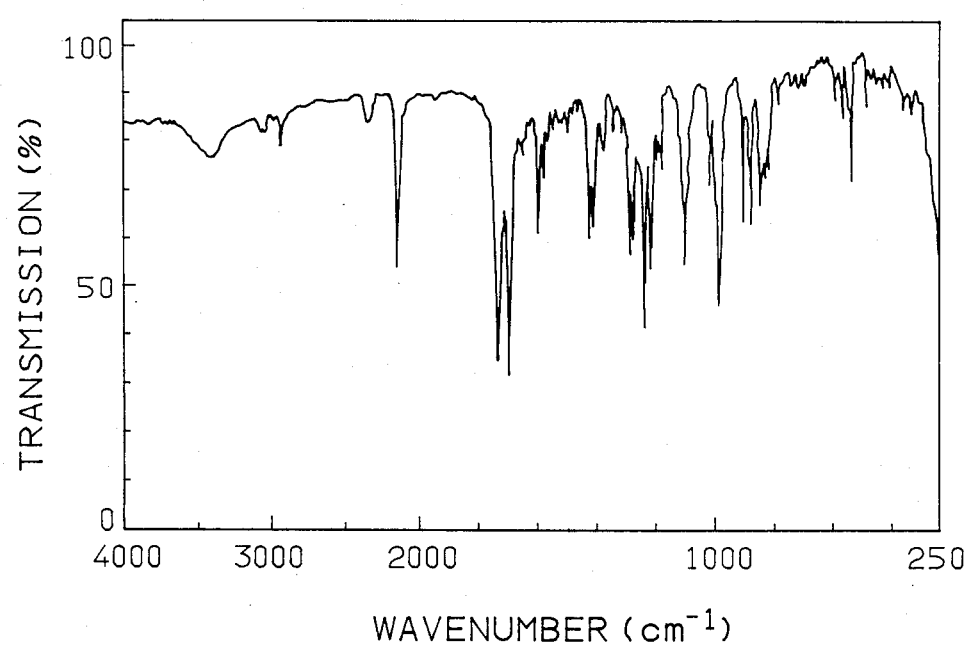
Figure 4:
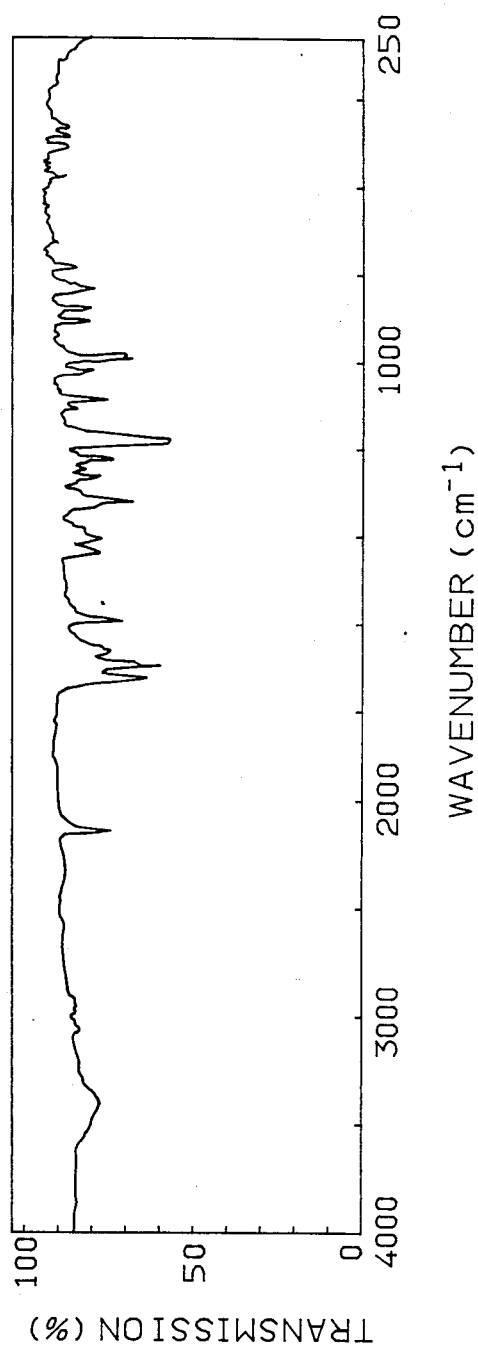
Figure 6:
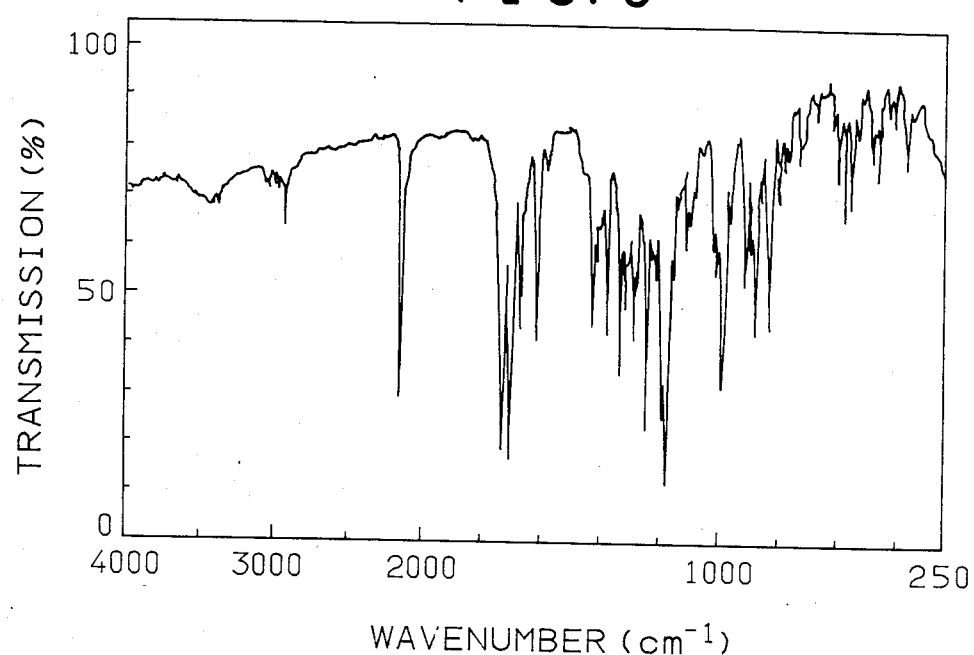
Figure 7:
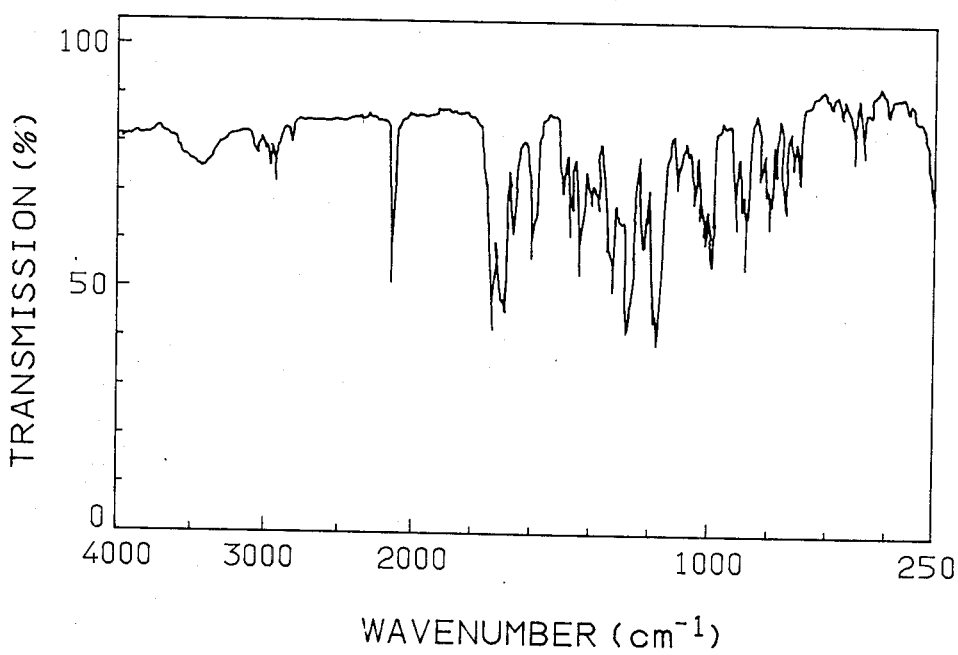
Figure 8:
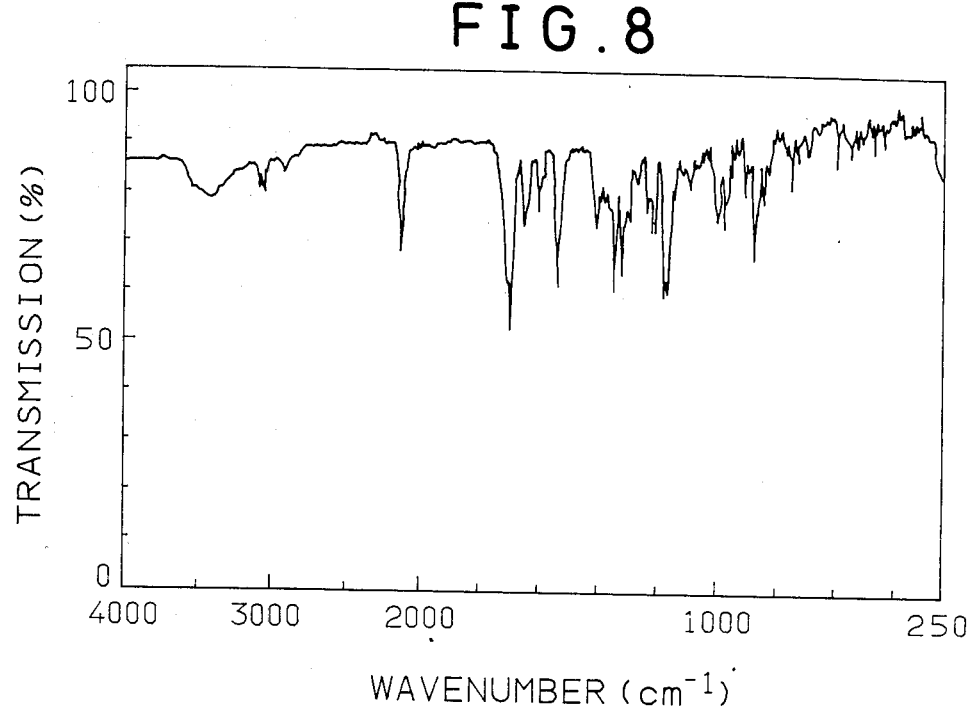
Figure 75:
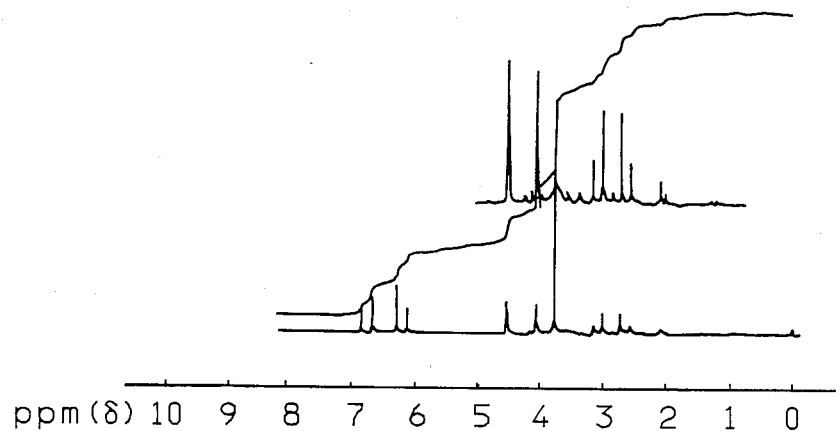
FIGS. 75 to 157 are the respective nuclear magnetic resonance spectra thereof.
Figure 76:
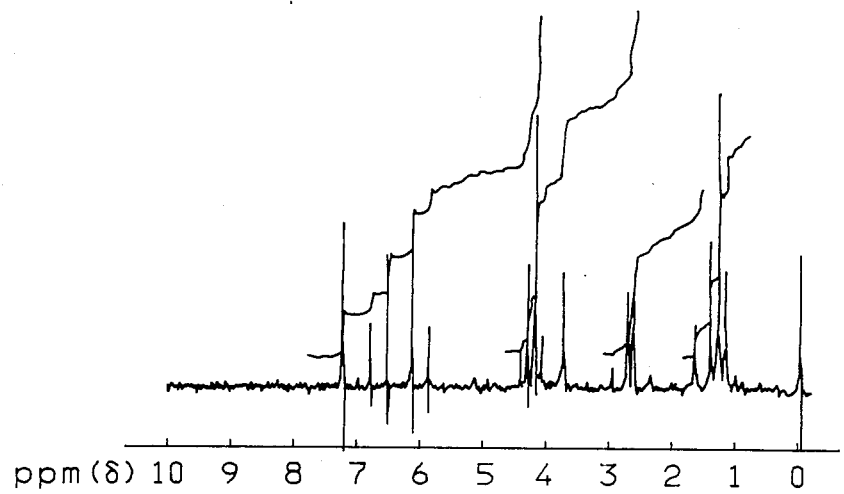
Figure 77:
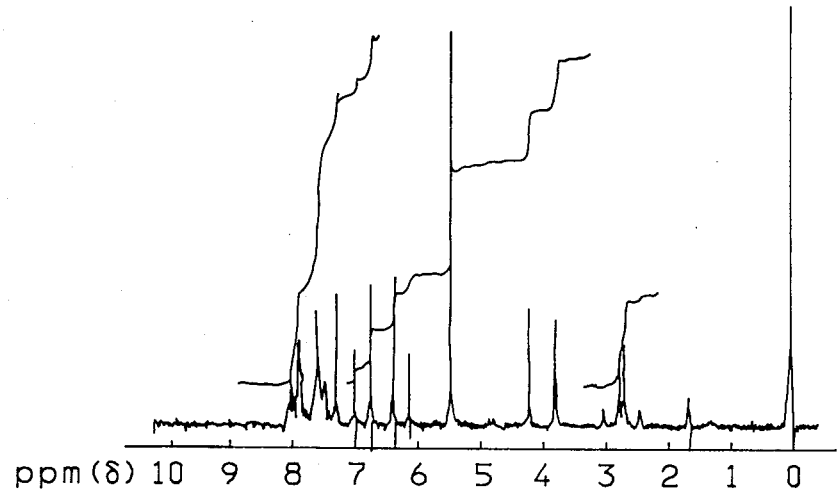
Figure 78:
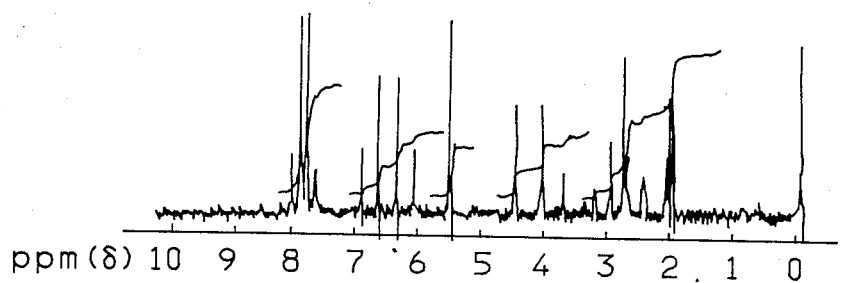
Figure 79:
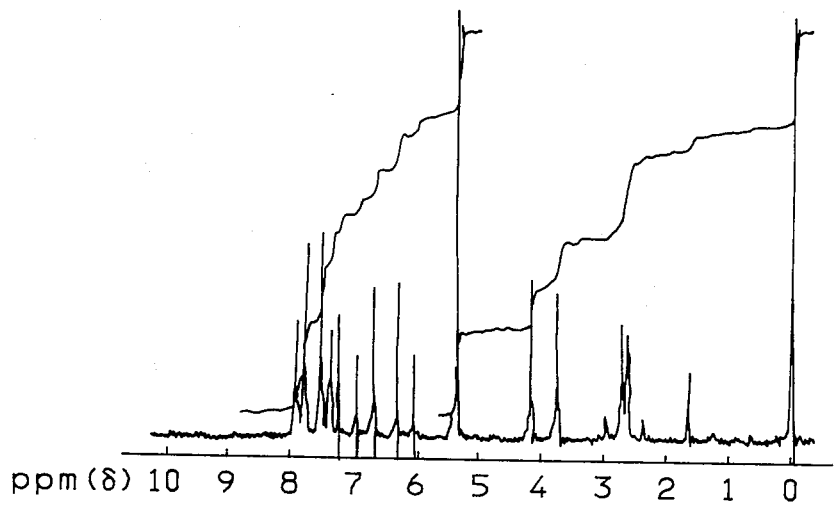
Figure 80:
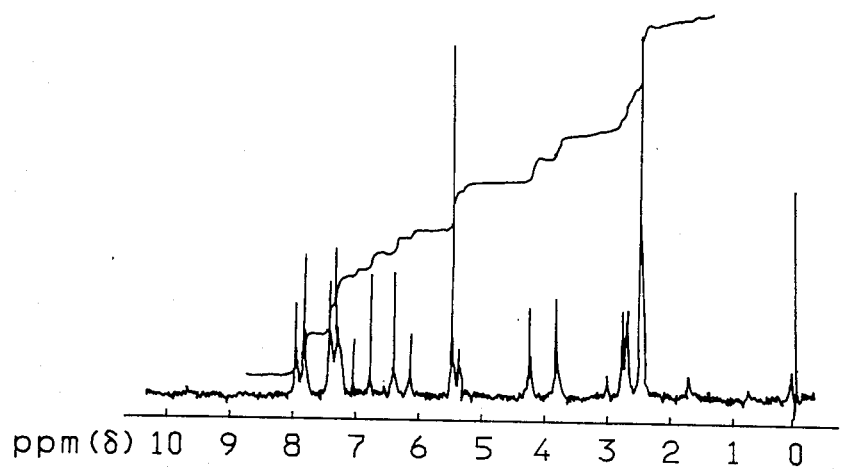
Figure 81:
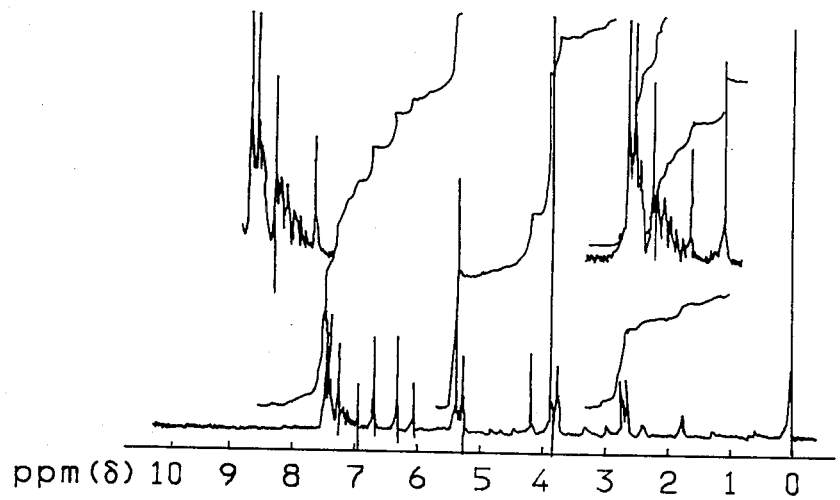
Figure 82:
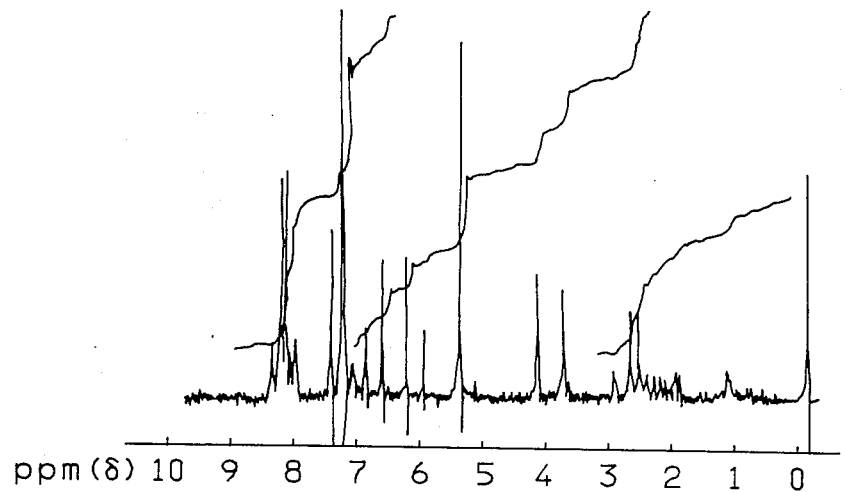

| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 1 | —O—CH$_3$ | oil | — | FIG. 1 | FIG. 75 (CDCl$_3$) |
| 2 | —O—C$_2$H$_5$ | oil | — | FIG. 2 | FIG. 76 (CDCl$_3$) |
| 3 | —O—CH$_2$CO—C$_6$H$_5$ | lamellar crystal | 128–129 (dec.) | FIG. 3 | FIG. 77 (CDCl$_3$) |
| 4 | —O—CH$_2$CO—C$_6$H$_4$—Br (4-) | acicular crystal | 153.5–154.5 (dec.) | FIG. 4 | FIG. 78 ((CD$_3$)$_2$CO) |
| 5 | —O—CH$_2$CO—C$_6$H$_4$—Cl (4-) | lamellar crystal | 144–145 (dec.) | FIG. 5 | FIG. 79 (CDCl$_3$) |
| 6 | —O—CH$_2$CO—C$_6$H$_4$—CH$_3$ (4-) | acicular crystal | 139–140 (dec.) | FIG. 6 | FIG. 80 (CDCl$_3$) |
| 7 | —O—CH$_2$CO—C$_6$H$_4$—OCH$_3$ (3-) | acicular crystal | 49–50 (dec.) | FIG. 7 | FIG. 81 (CDCl$_3$) |
| 8 | —O—CH$_2$CO—C$_6$H$_4$—NO$_2$ (4-) | lamellar crystal | 123–127 (dec.) | FIG. 8 | FIG. 82 (CDCl$_3$ + (CD$_3$)$_2$CO) |

Figure 9:
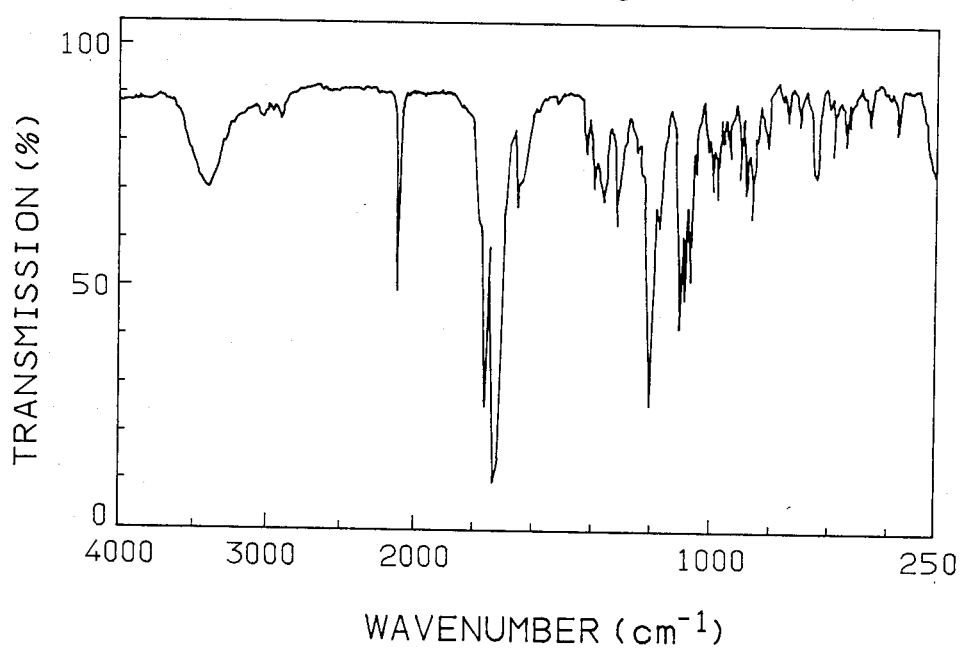
Figure 10:
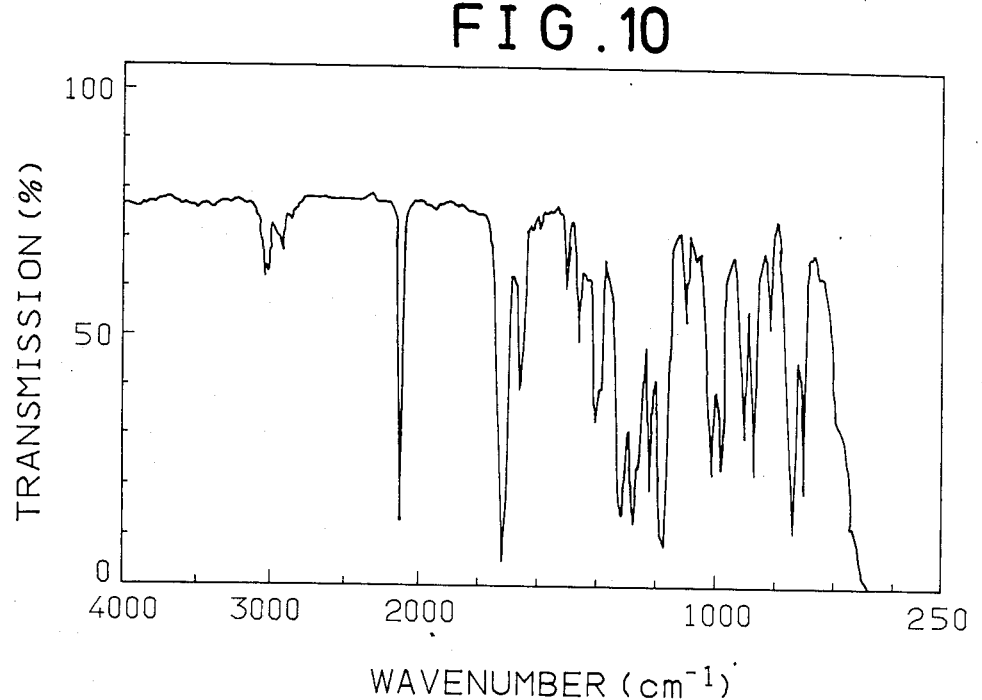
Figure 11:
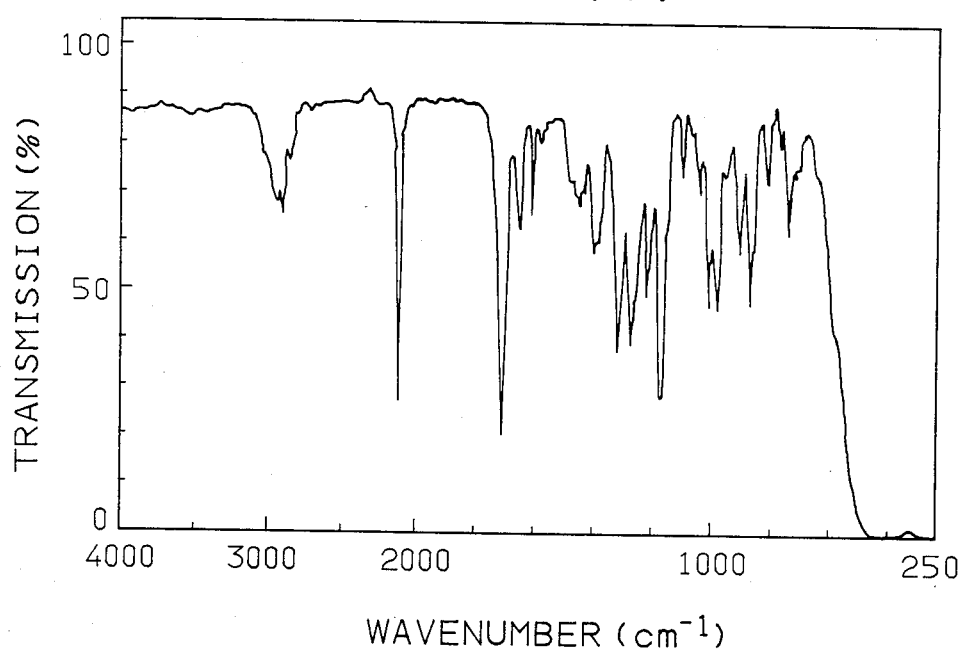
Figure 12:
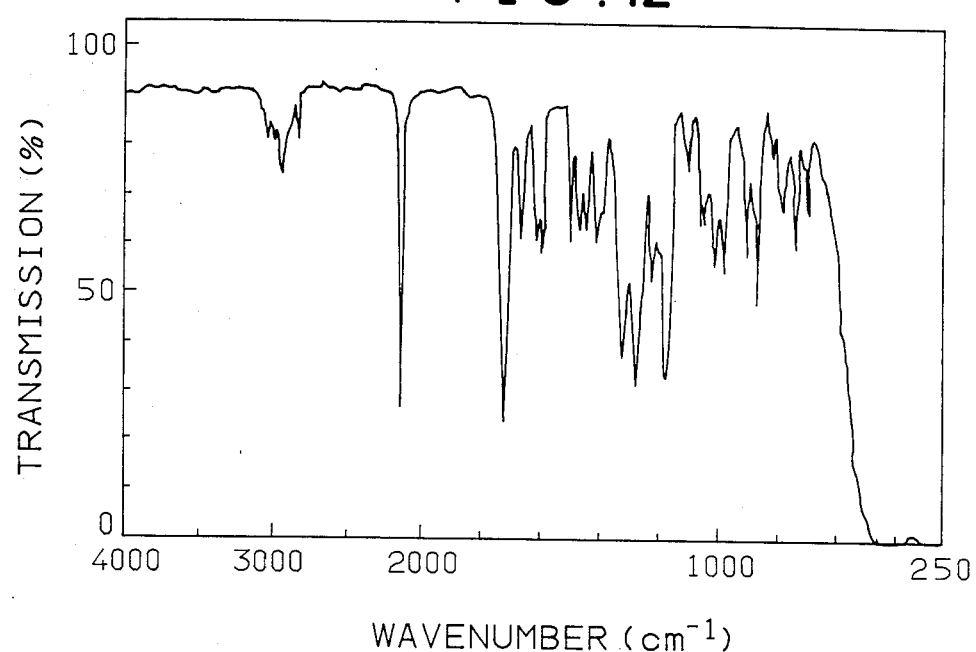
Figure 13:
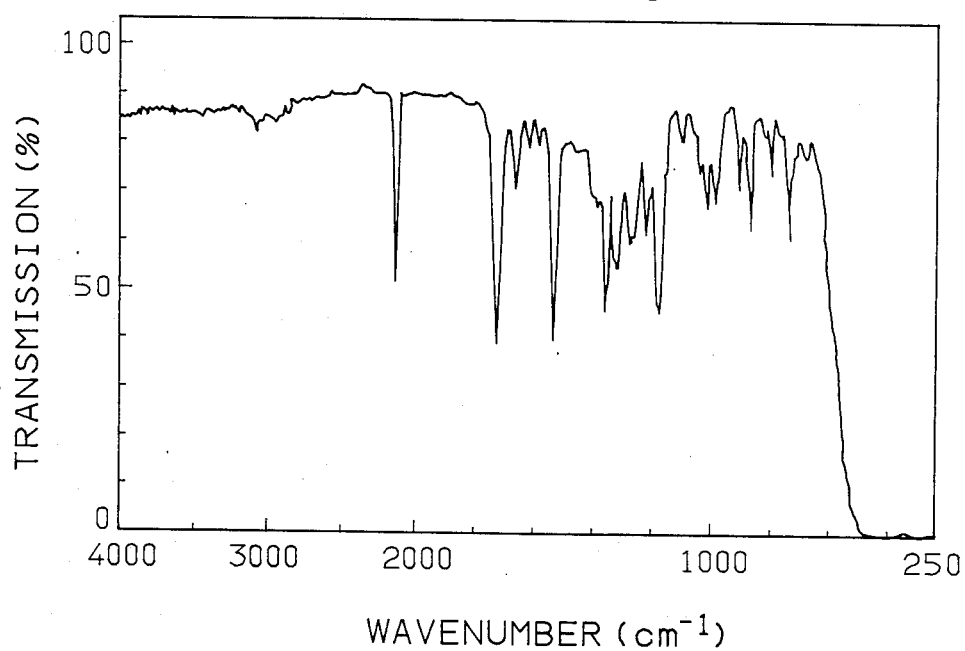
Figure 83:
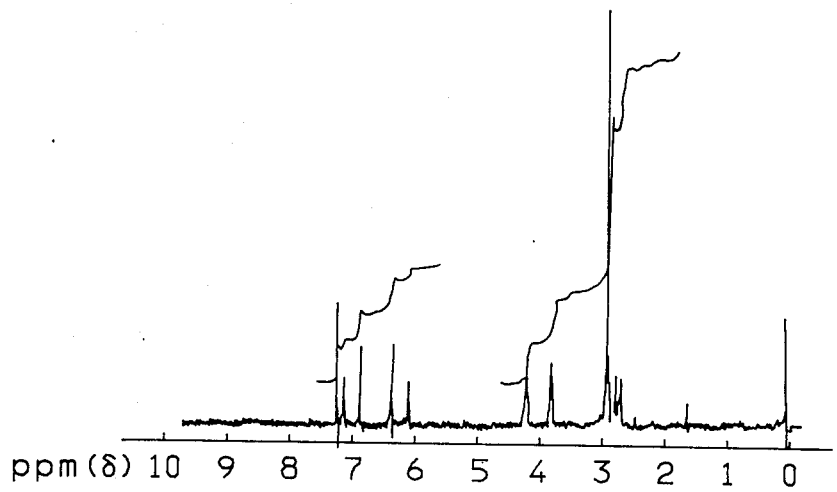
Figure 84:
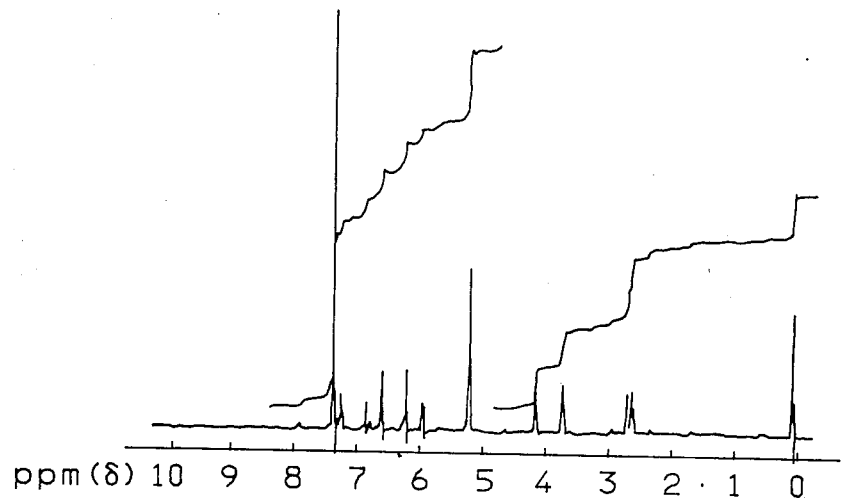
Figure 85:
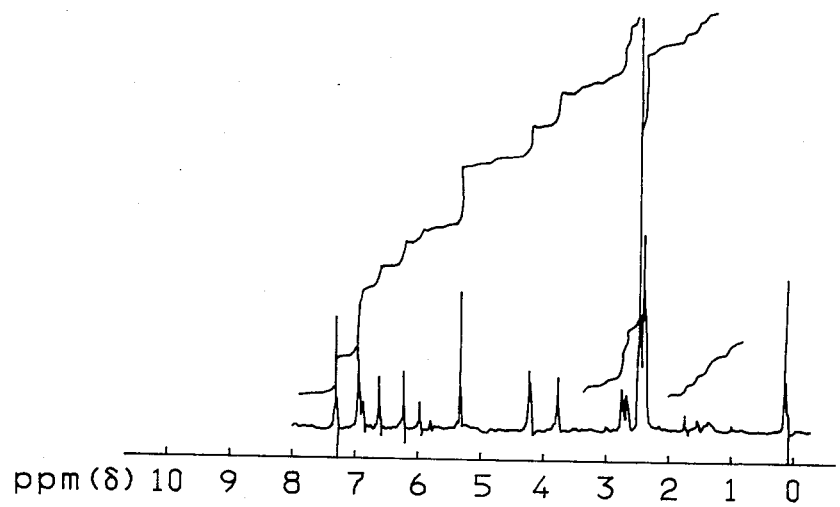
Figure 86:
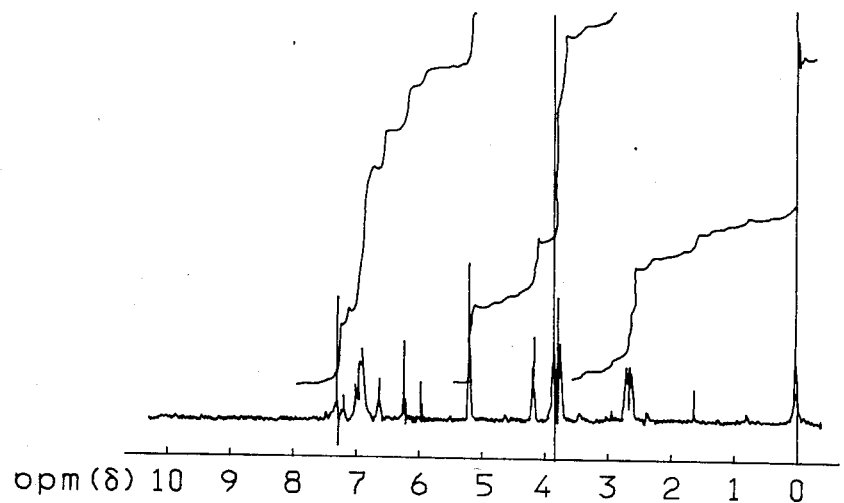
Figure 87:
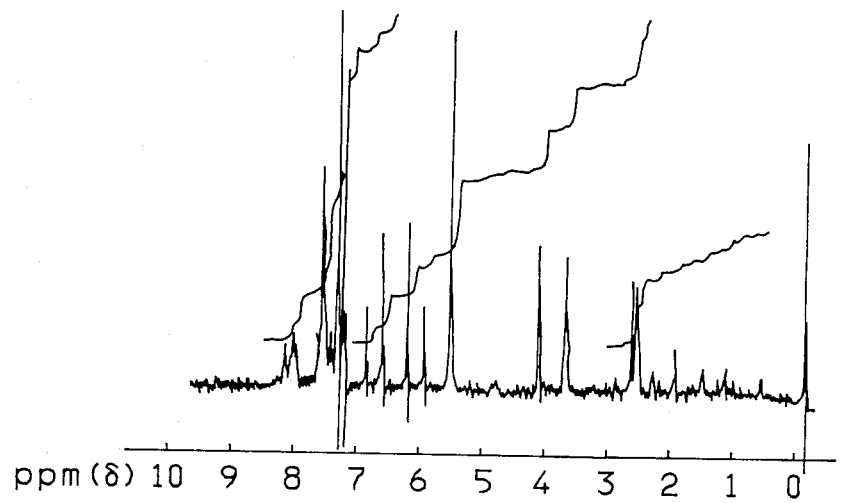

TABLE 1-continued
| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 9 |  | acicular crystal | 115 (dec.) | FIG. 9 | FIG. 83 (CDCl$_3$) |
| 10 | 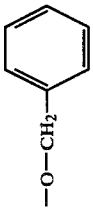 | oil | — | FIG. 10 | FIG. 84 (CDCl$_3$) |
| 11 | 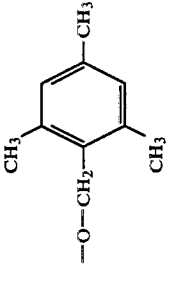 | oil | — | FIG. 11 | FIG. 85 (CDCl$_3$) |
| 12 | 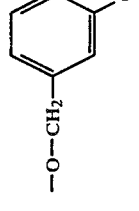 | oil | — | FIG. 12 | FIG. 86 (CDCl$_3$) |
| 13 | 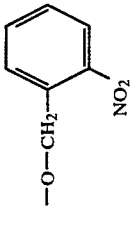 | oil | — | FIG. 13 | FIG. 87 (CDCl$_3$) |

TABLE 1-continued

[Structure: cyclopentane ring with CN, two O substituents, and CH=CH-C(=O)-A group]

Figure 14:
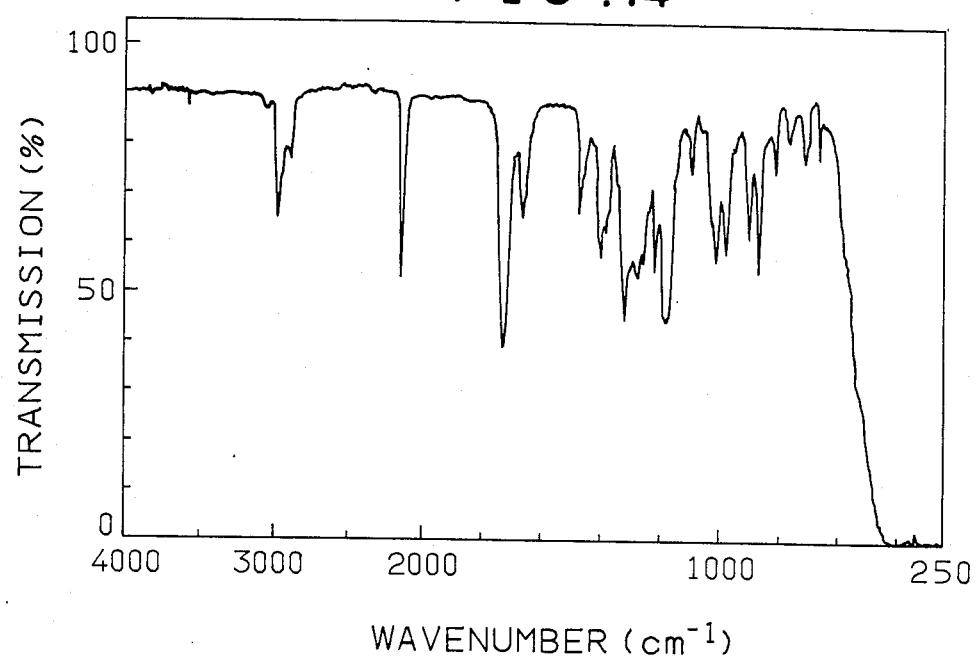
Figure 15:
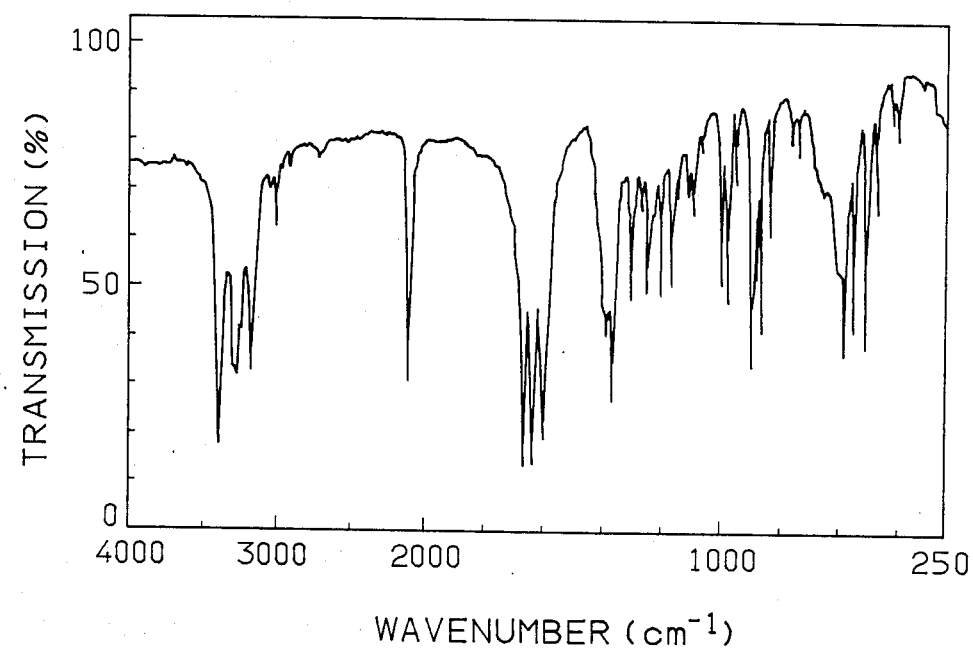
Figure 88:
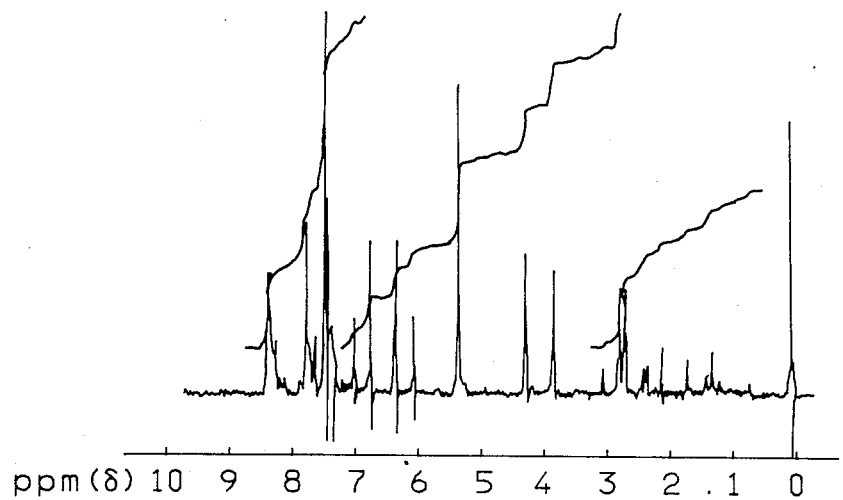
Figure 89:
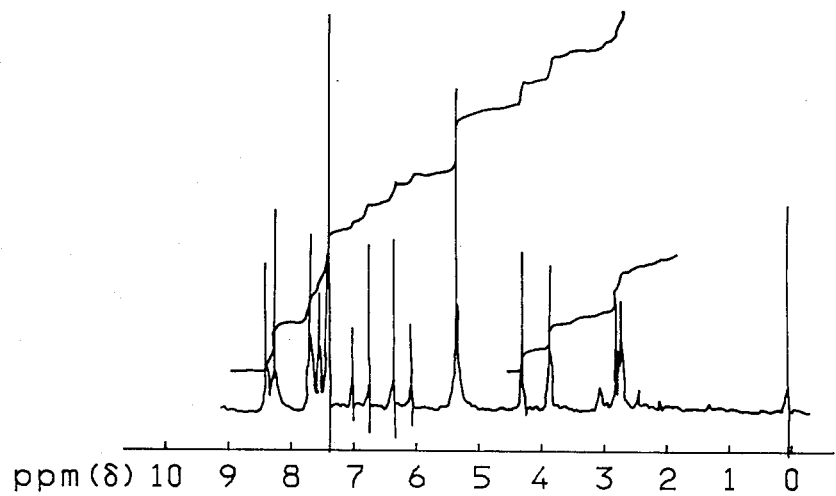
Figure 90:
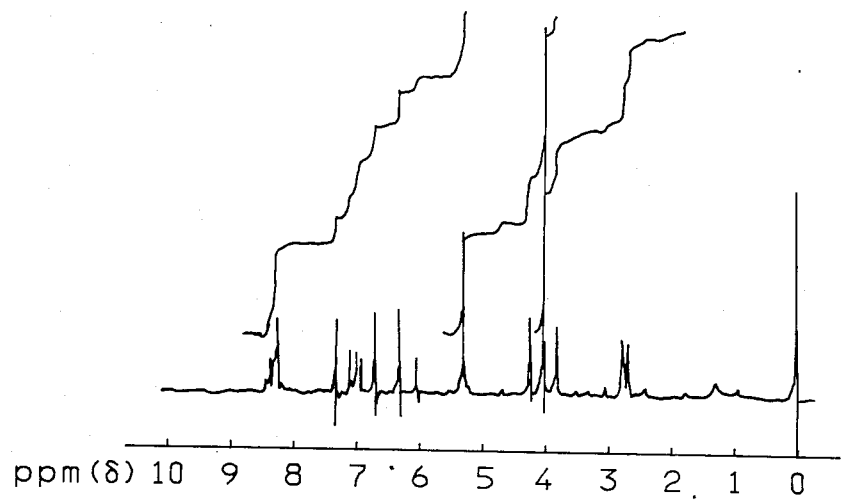
Figure 91:
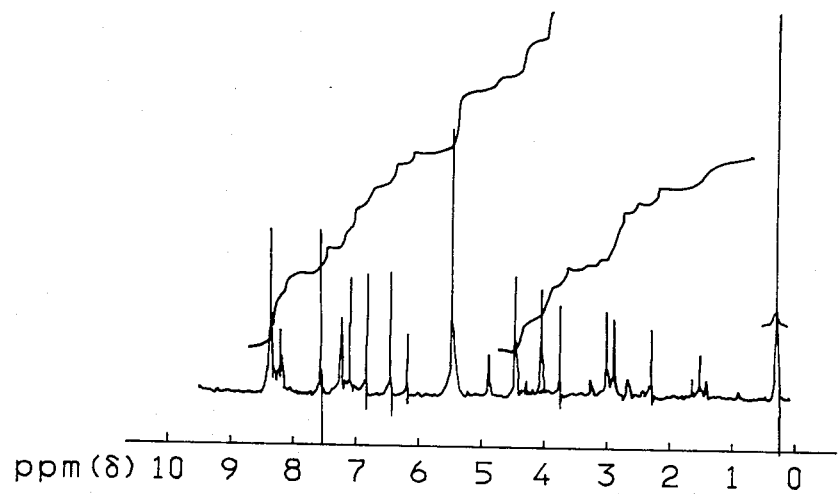
Figure 92:
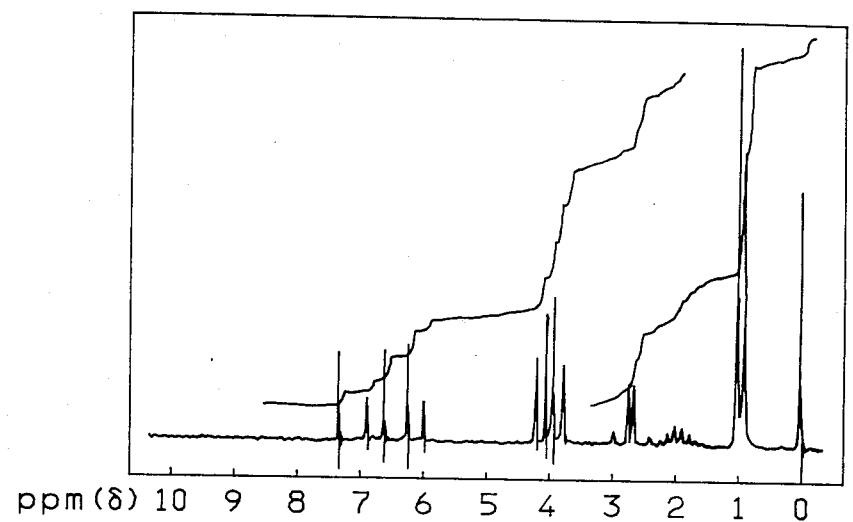
Figure 93:
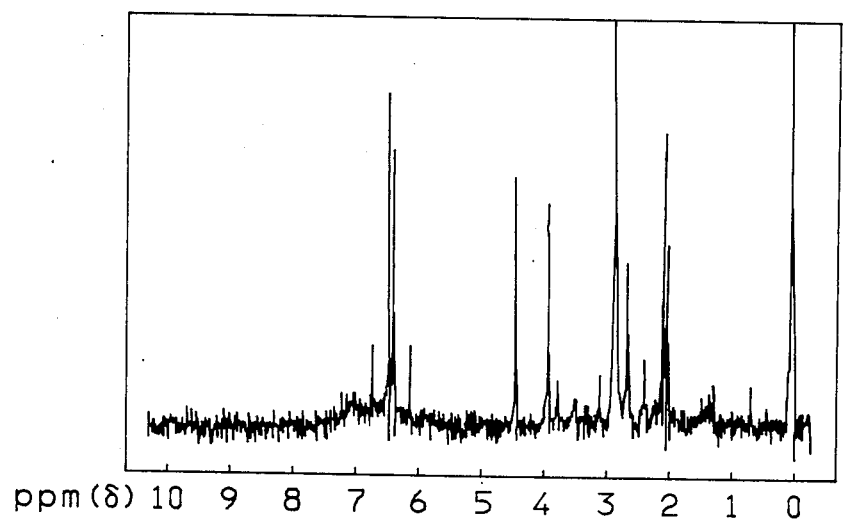

| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 14 | —O—CH$_2$—(3-NO$_2$-C$_6$H$_4$) | oil | — | | FIG. 88 (CDCl$_3$) |
| 15 | —O—CH$_2$—(4-NO$_2$-C$_6$H$_4$) | oil | — | | FIG. 89 (CDCl$_3$) |
| 16 | —O—CH$_2$—(4-NO$_2$-2-CH$_3$O-C$_6$H$_3$) | oil | — | | FIG. 90 (CDCl$_3$) |
| 17 | —O—CH$_2$—(4-NO$_2$-2-HO-C$_6$H$_3$) | oil | — | | FIG. 91 (CDCl$_3$ + (CD$_3$)$_2$CO) |
| 18 | —O—CH$_2$CH(CH$_3$)$_2$ | oil | — | FIG. 14 | FIG. 92 |
| 19 | —NH$_2$ | acicular crystal | >120 (dec.) | FIG. 15 | FIG. 93 ((CD$_3$)$_2$CO) |

TABLE 1-continued

Figure 16:
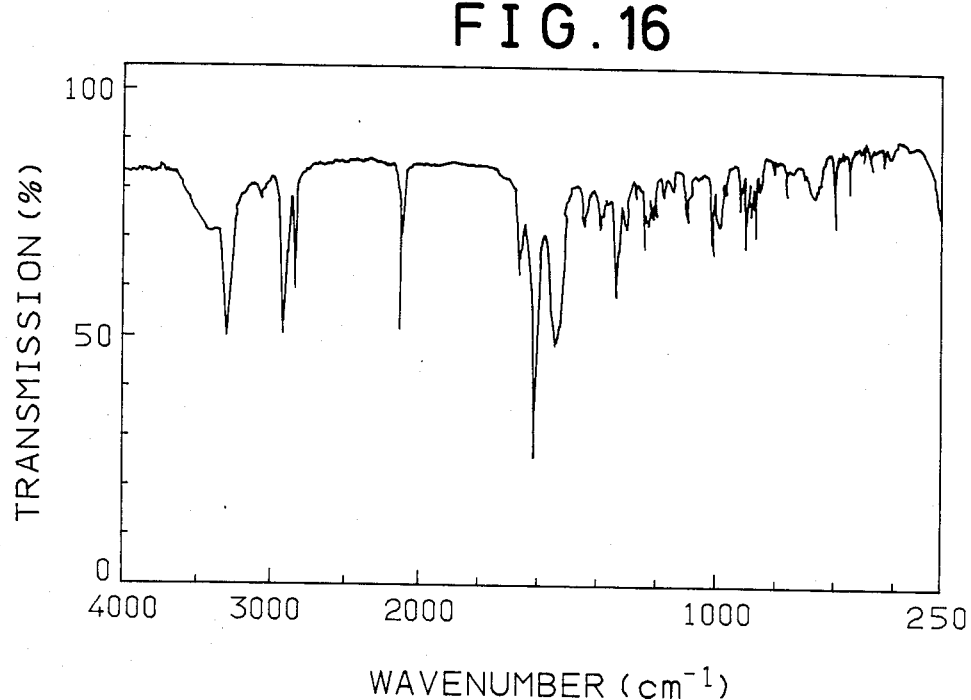
Figure 17:
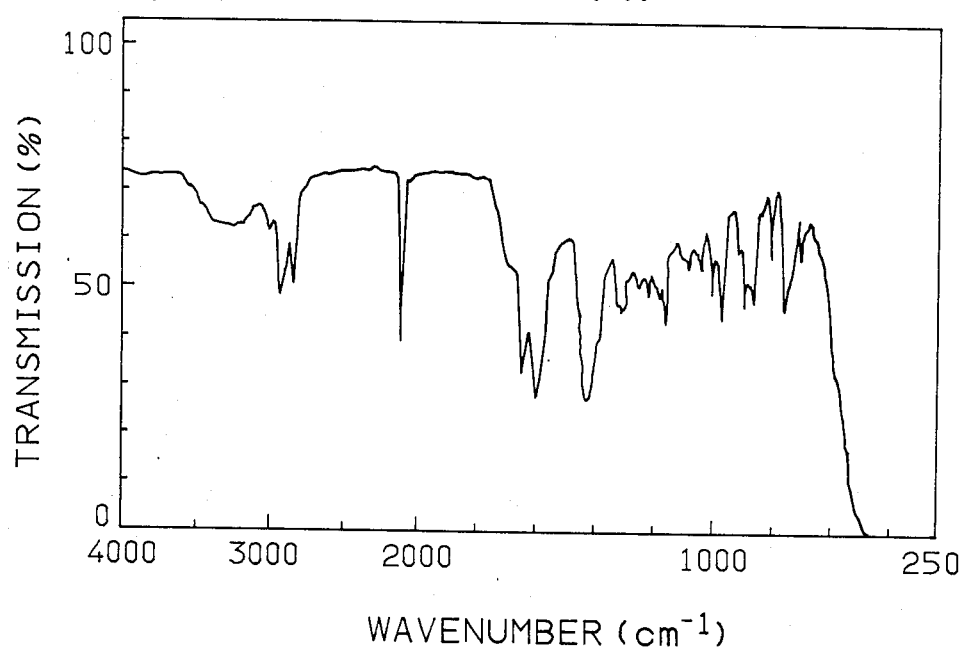
Figure 18:
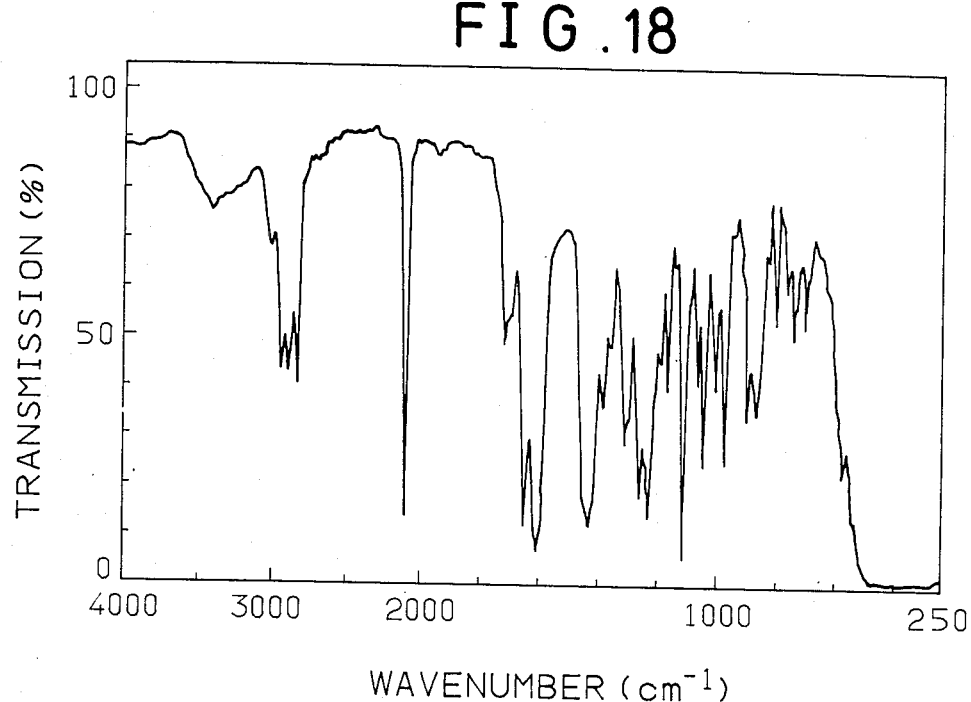
Figure 19:
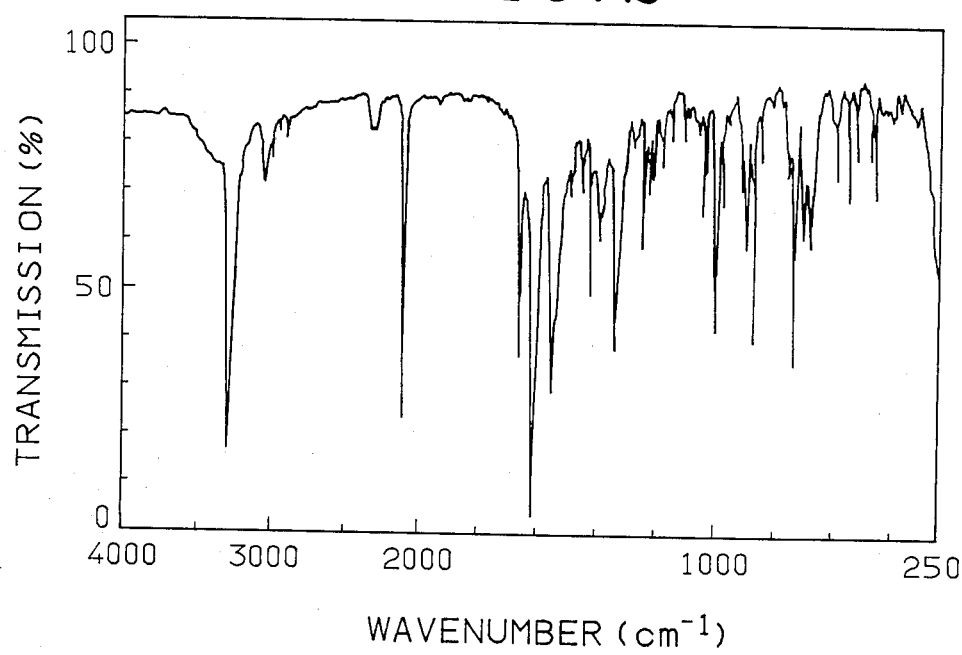
Figure 20:
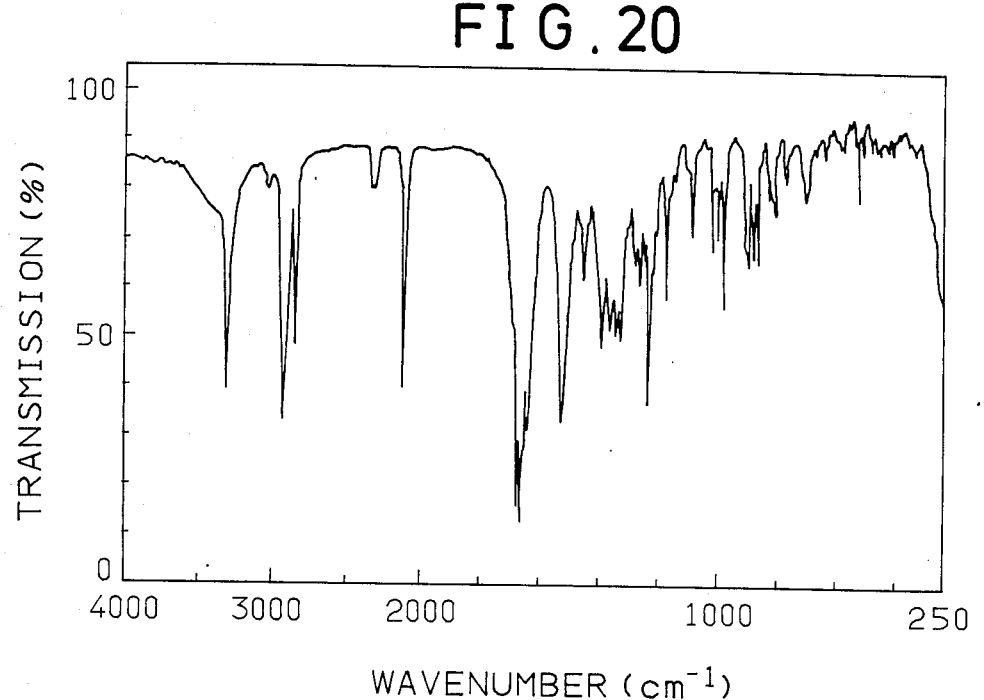
Figure 21:
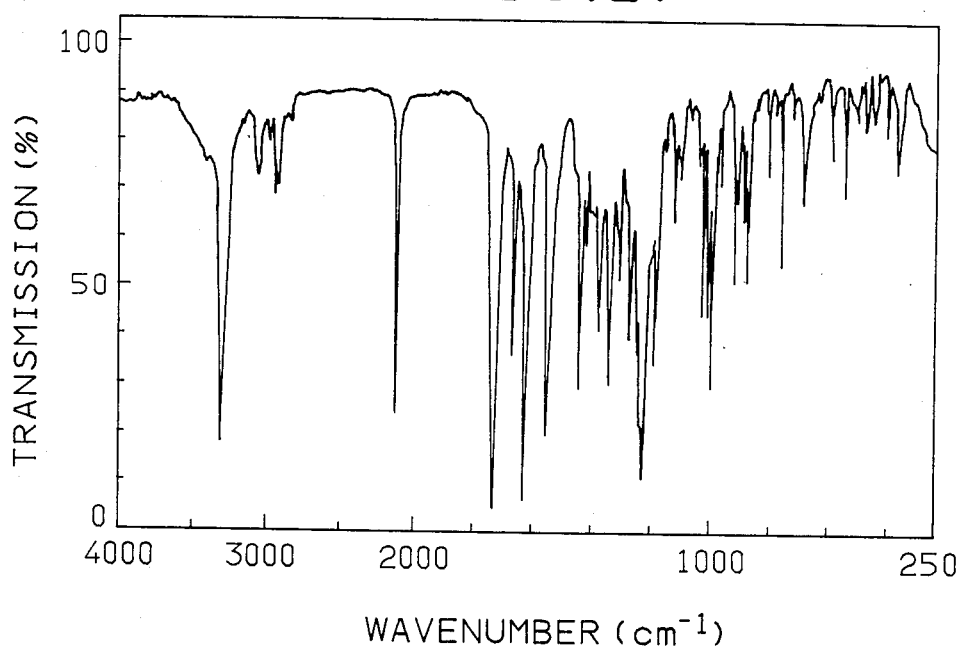
Figure 94:
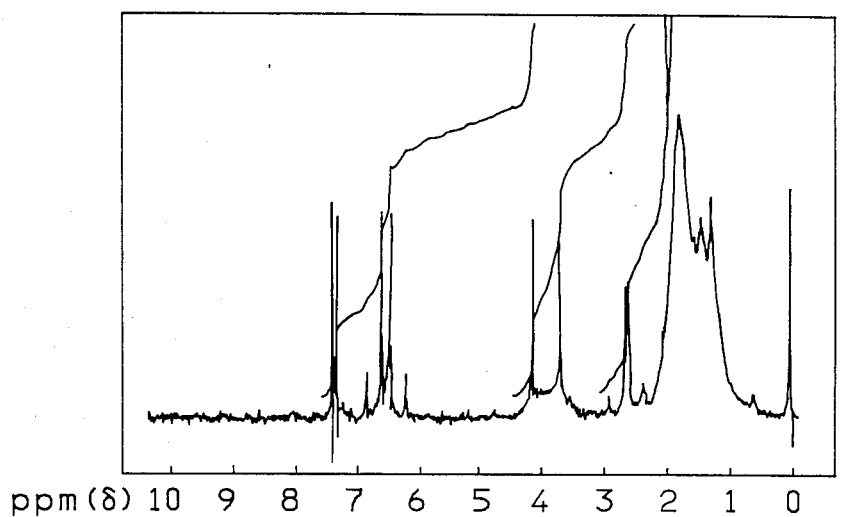
Figure 95:
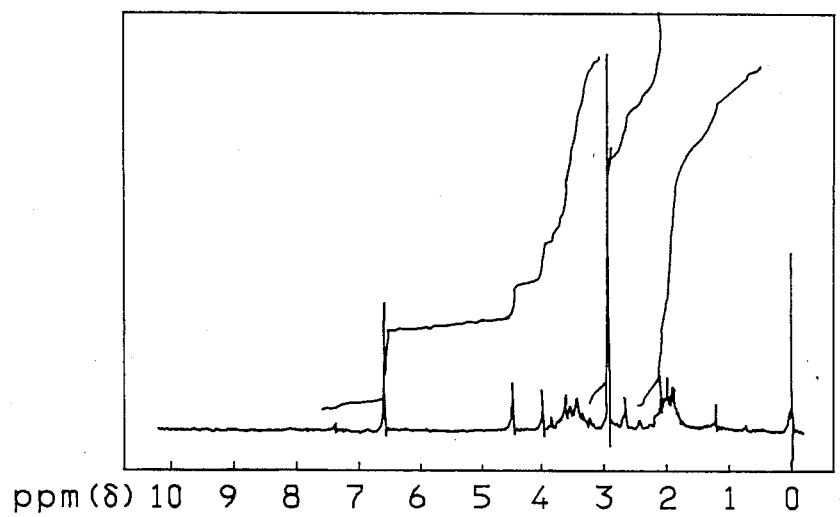
Figure 96:
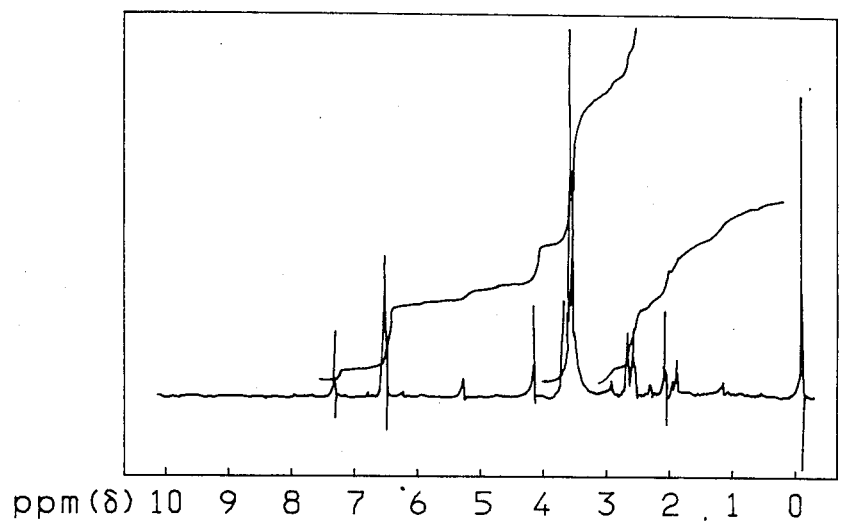
Figure 97:
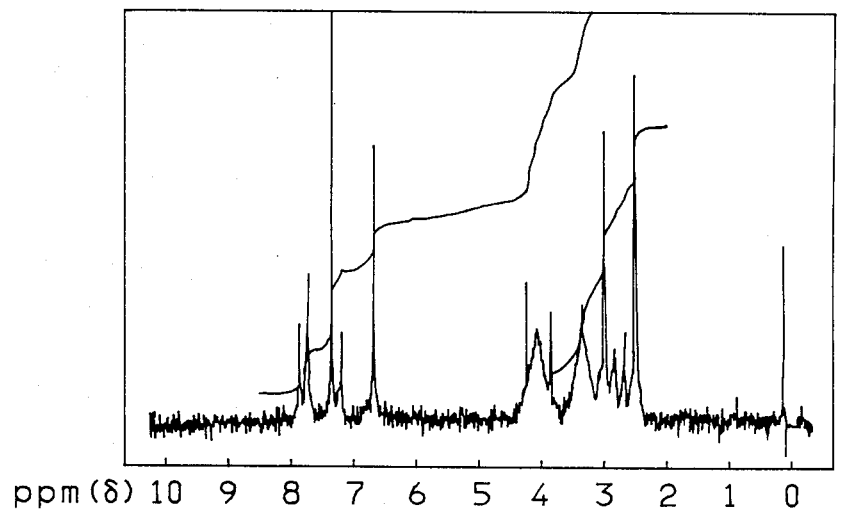
Figure 98:
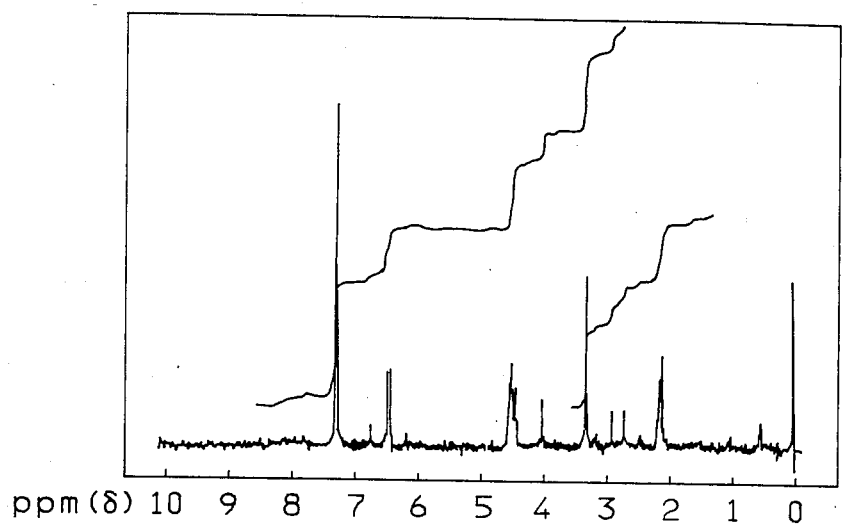
Figure 99:
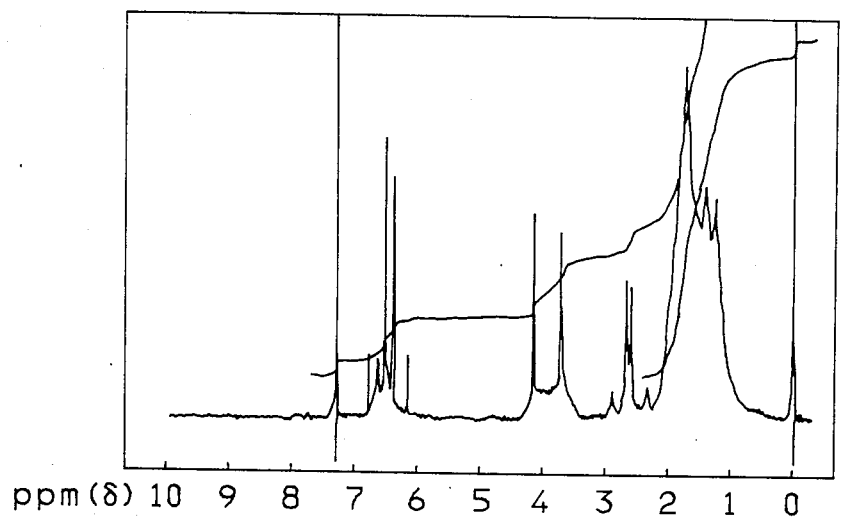
Figure 100:
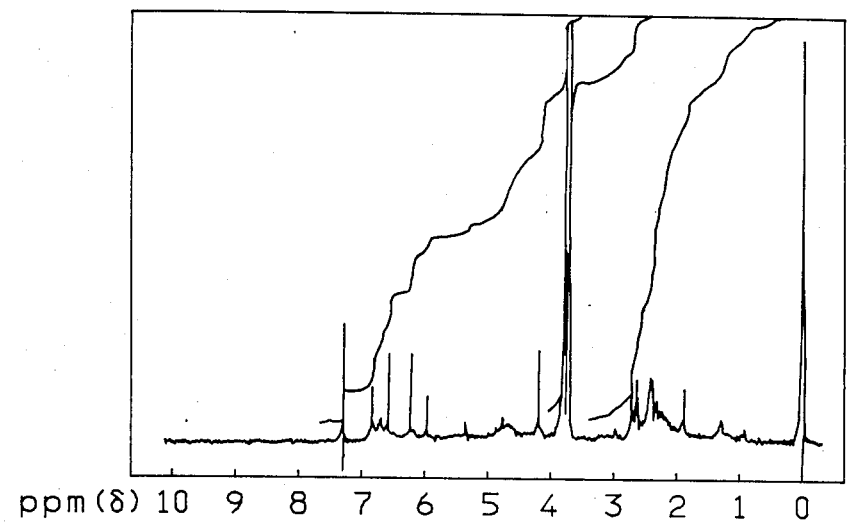

| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 20 | 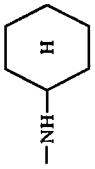 | acicular crystal | >178 (dec.) | FIG. 16 | FIG. 94 ((CD$_3$)$_2$CO) |
| 21 | 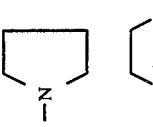 | oil | — | FIG. 17 (NaCl) | FIG. 95 ((CD$_3$)$_2$CO) |
| 22 | 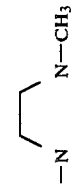 | oil | | FIG. 18 (NaCl) | FIG. 96 (CD$_2$Cl$_2$) |
| 23 | 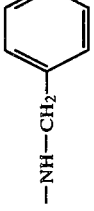 | oil | | — | FIG. 97 (CD$_2$Cl$_2$) |
| 24 | —NH—CH$_2$— 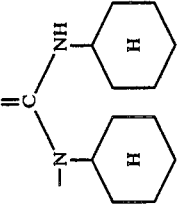 | acicular crystal | >160 (dec.) | FIG. 19 | FIG. 98 ((CD$_3$)$_2$CO + D$_2$O) |
| 25 |  | lamellar crystal | 156–157 (dec.) | FIG. 20 | FIG. 99 (CDCl$_3$) |
| 26 | —NH—CH—CH$_2$CH$_2$COOCH$_3$<br>  \|<br>  O=CO—CH$_3$ | acicular crystal | 131–132 | FIG. 21 | FIG. 100 (CDCl$_3$) |

TABLE 1-continued

[Structure: compound with CN, O, O ring and C=C-C(=O)-A group]

Figure 22:
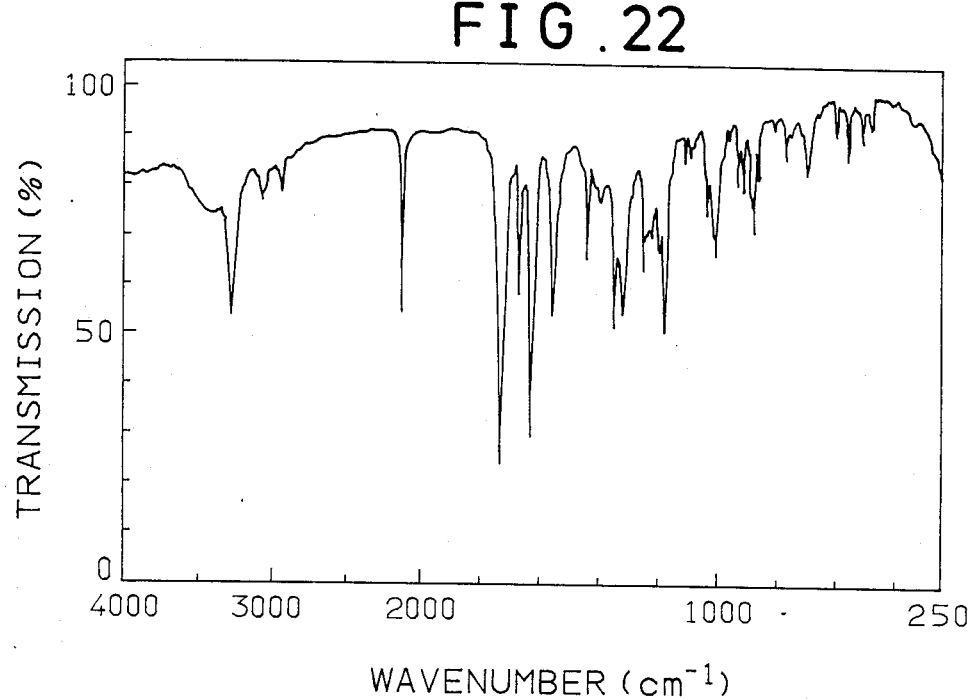
Figure 23:
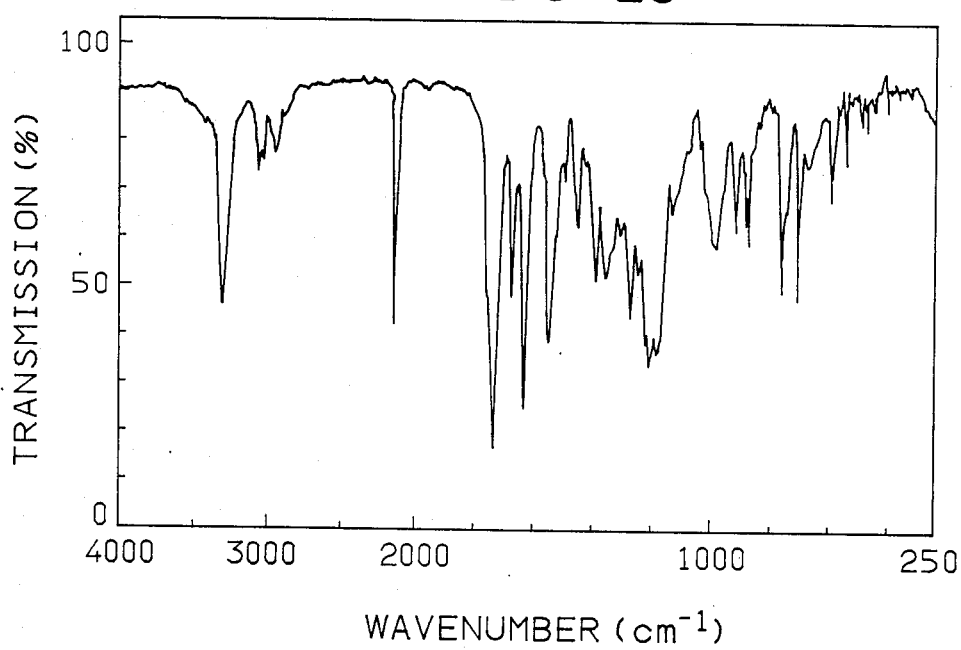
Figure 24:
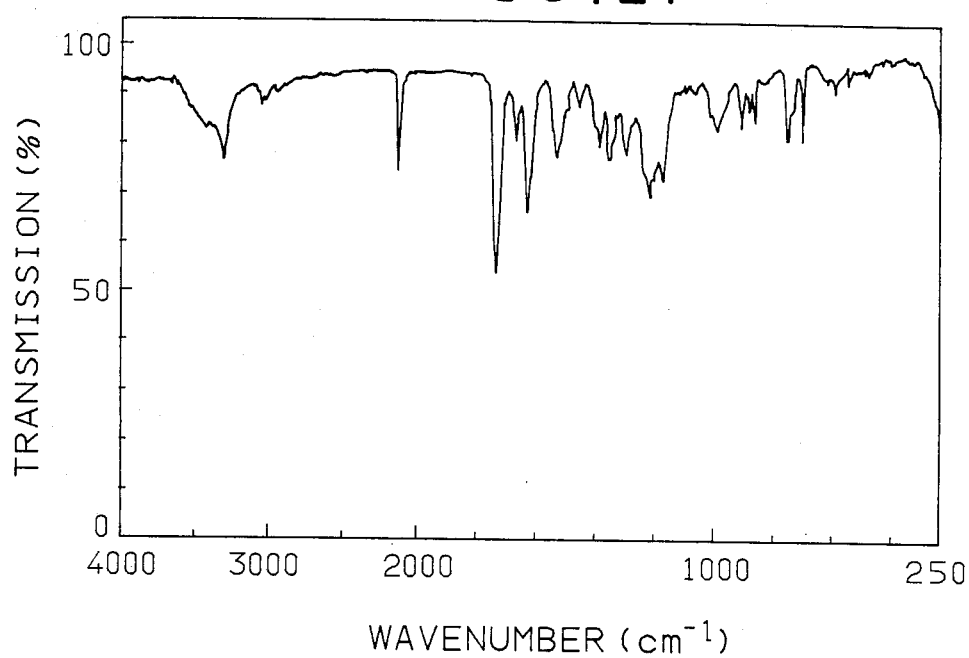
Figure 25:
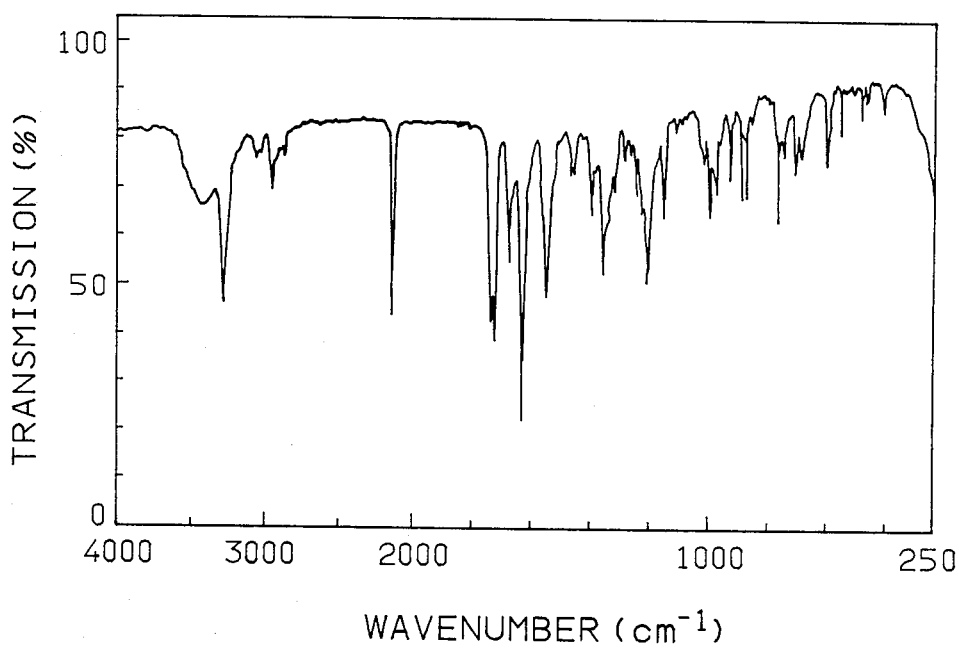
Figure 26:
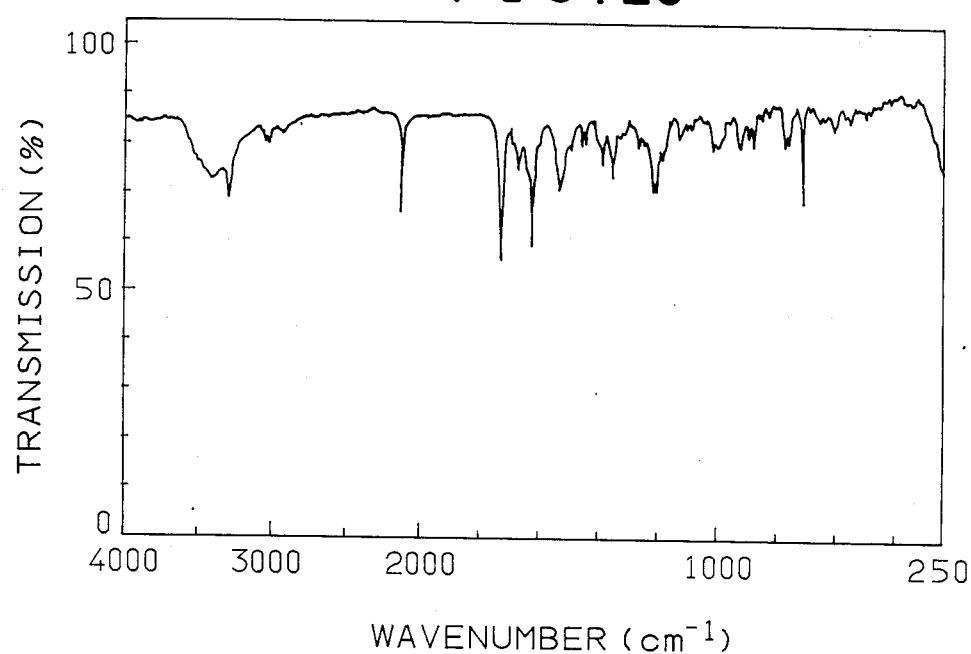
Figure 101:
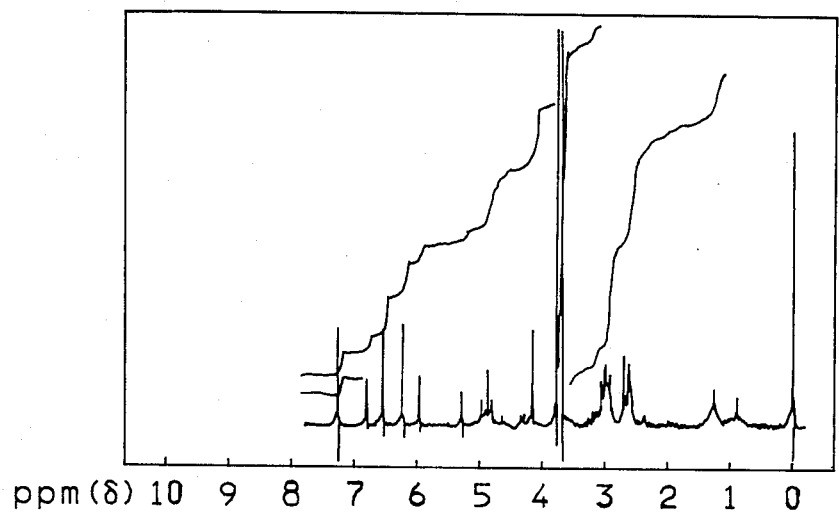
Figure 102:
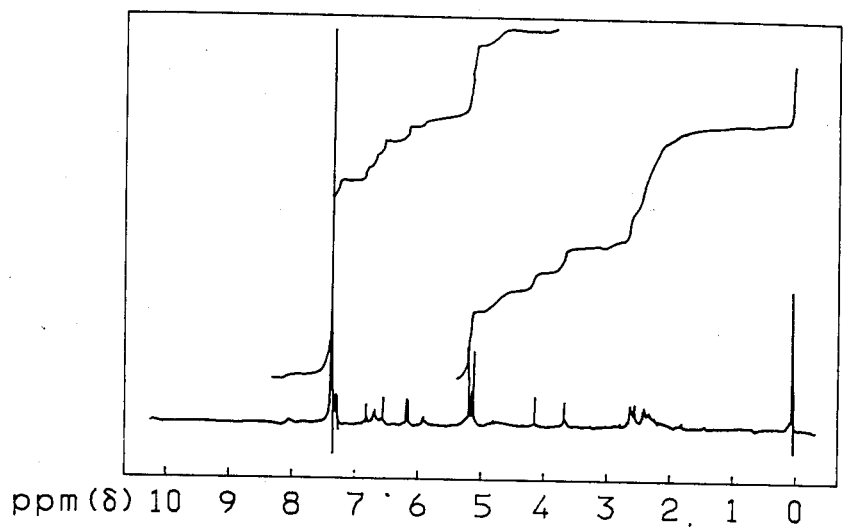
Figure 103:
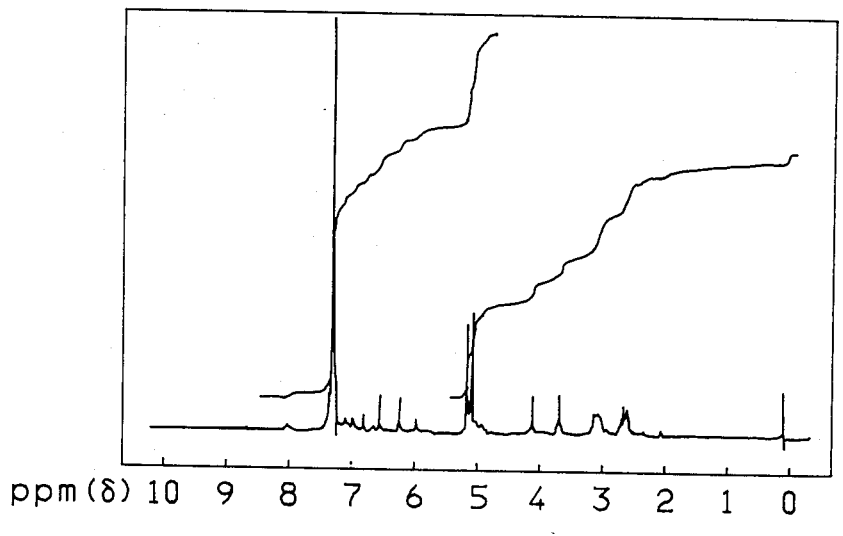
Figure 104:
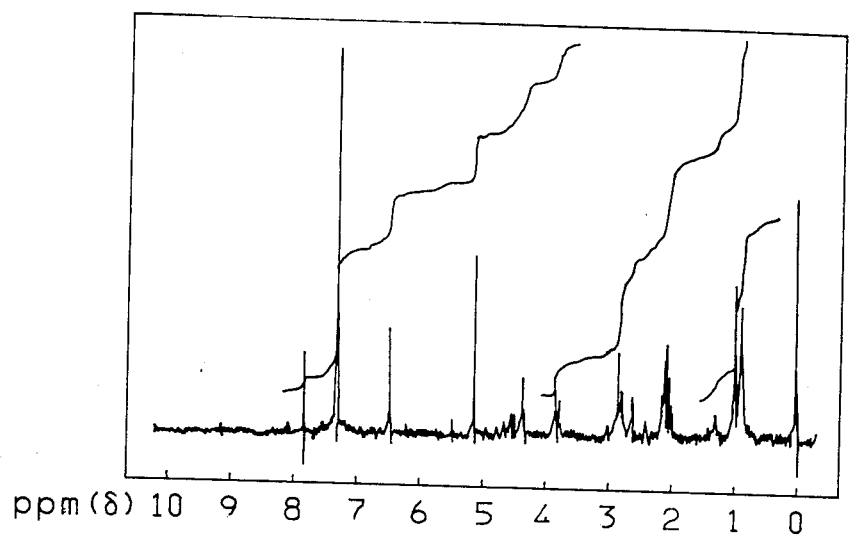
Figure 105:
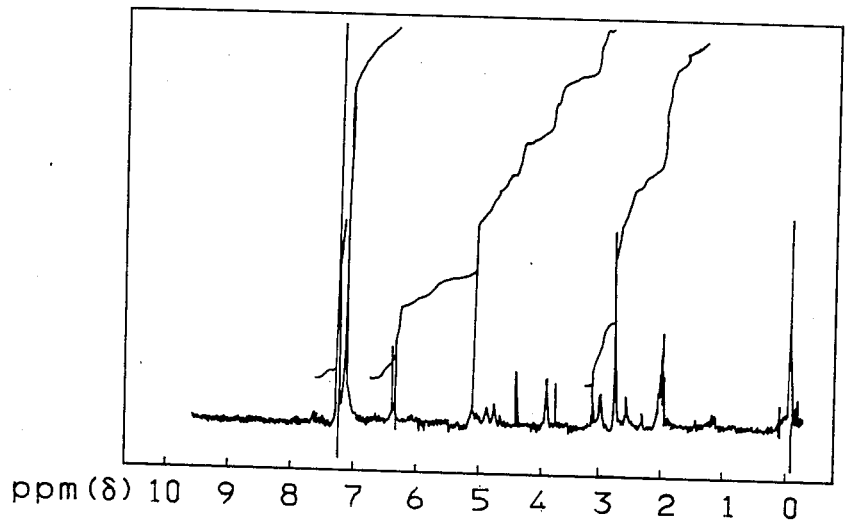

| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 27 | —NH—*CH—CH$_2$COOCH$_3$<br>　　　　O=CO—CH$_3$ | acicular crystal | 135–136 (dec.) | FIG. 22 | FIG. 101 (CDCl$_3$) |
| 28 | —NH—*CH—CH$_2$CH$_2$COOCH$_2$—C$_6$H$_5$<br>　　　　O=CO—CH$_3$ | acicular crystal | 110–111.5 (dec.) | FIG. 23 | FIG. 102 (CDCl$_3$) |
| 29 | —NH—*CH—CH$_2$—COOCH$_2$—C$_6$H$_5$<br>　　　　O=CO—CH$_2$—C$_6$H$_5$ | acicular crystal | 111–115 (dec.) | FIG. 24 | FIG. 103 (CDCl$_3$) |
| 30 | —NH—**CH—CH(CH$_3$)$_2$<br>　　　　O=CO—CH$_2$—C$_6$H$_5$ | acicular crystal | 148 (dec.) | FIG. 25 | FIG. 104 ((CD$_3$)$_2$CO) |
| 31 | —NH—*CH—CH$_2$—C$_6$H$_5$<br>　　　　O=CO—CH$_2$—C$_6$H$_5$ | acicular crystal | >120 (coloration) | FIG. 26 | FIG. 105 ((CD$_3$)$_2$CO + CDCl$_3$) |

TABLE 1-continued

Figure 27:
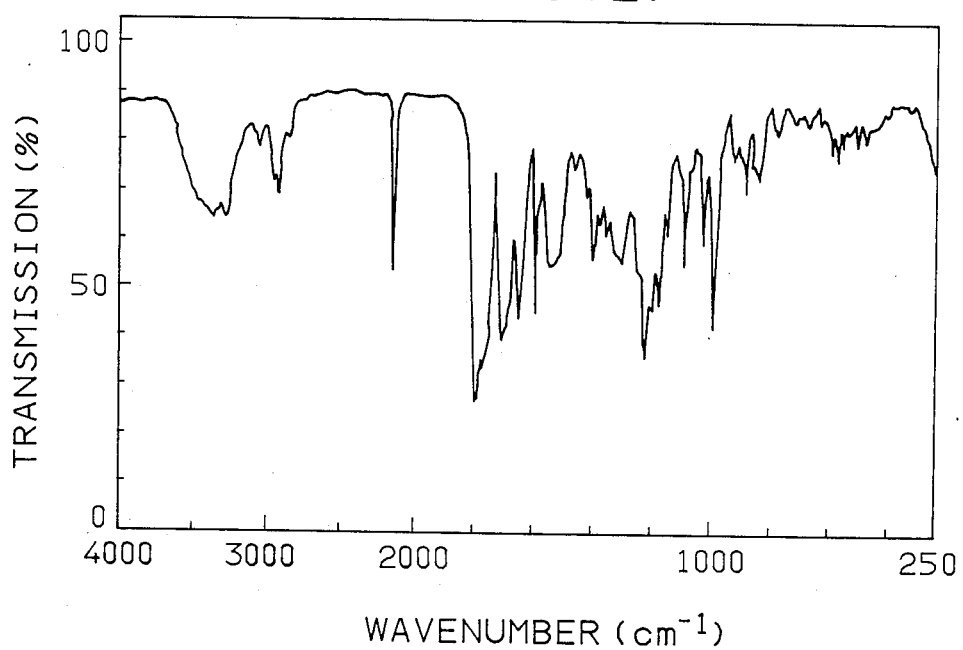
Figure 28:
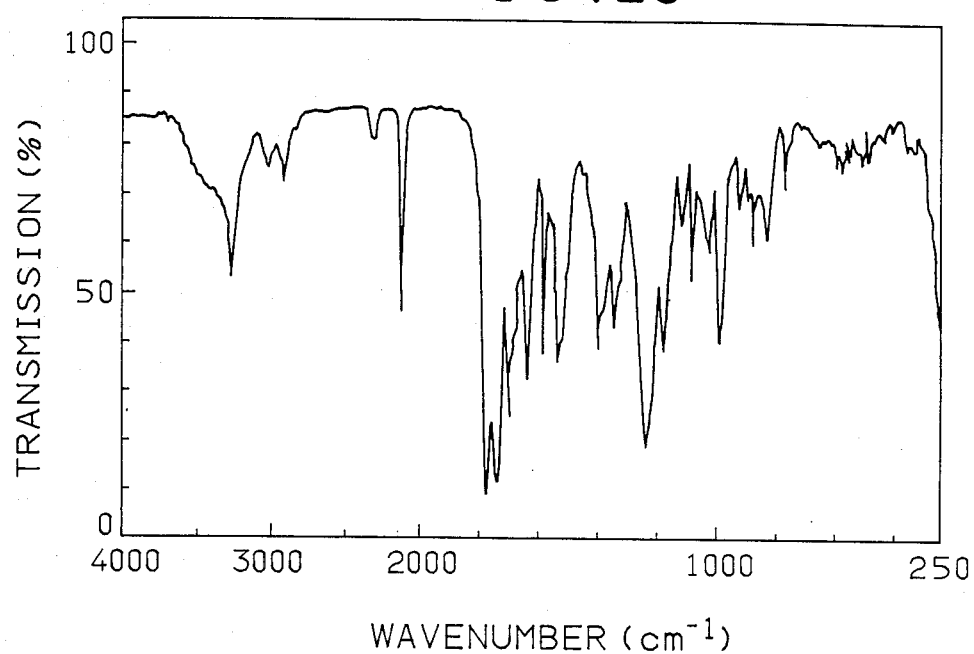
Figure 29:
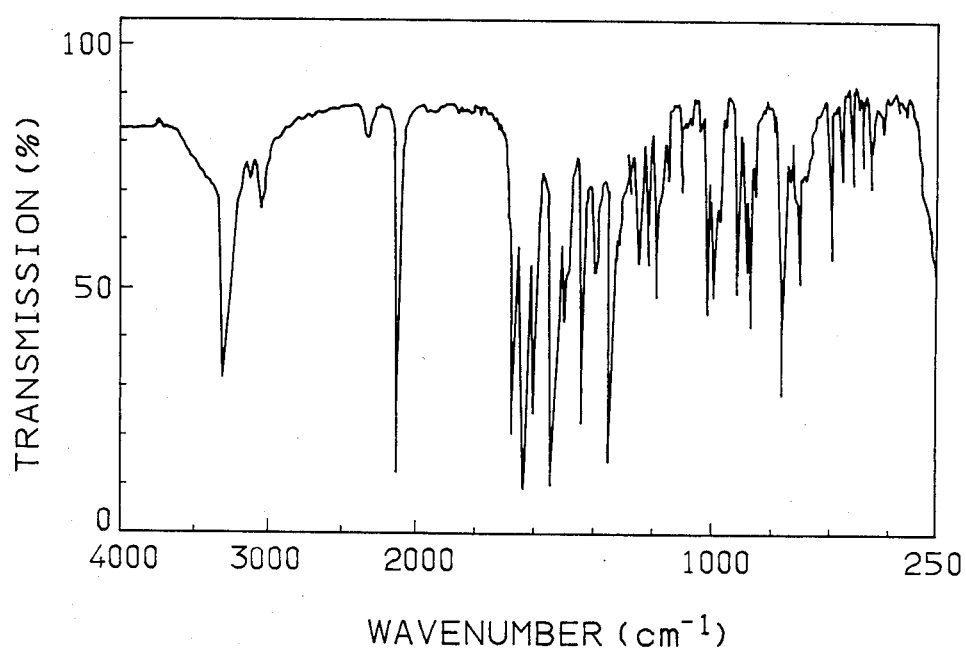
Figure 106:
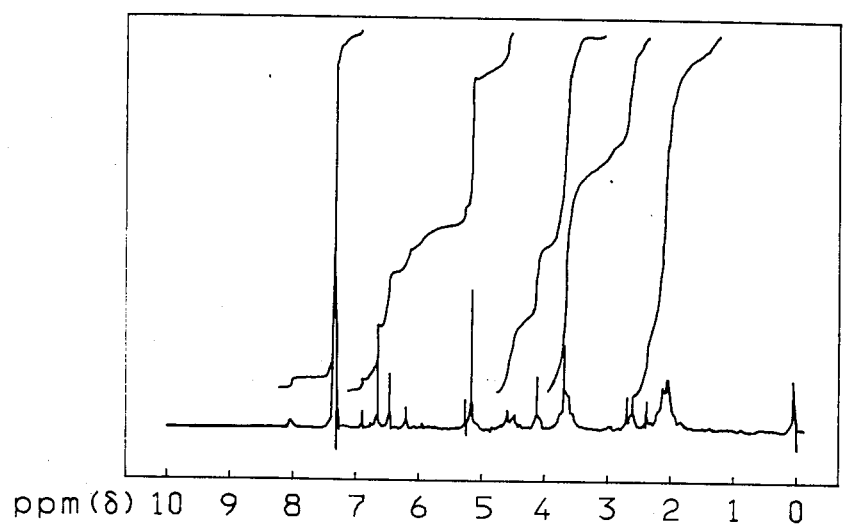
Figure 107:
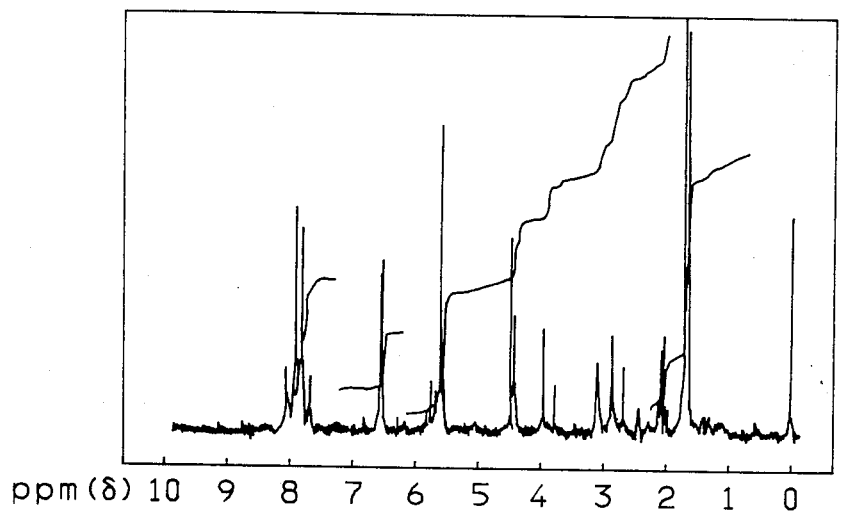
Figure 108:
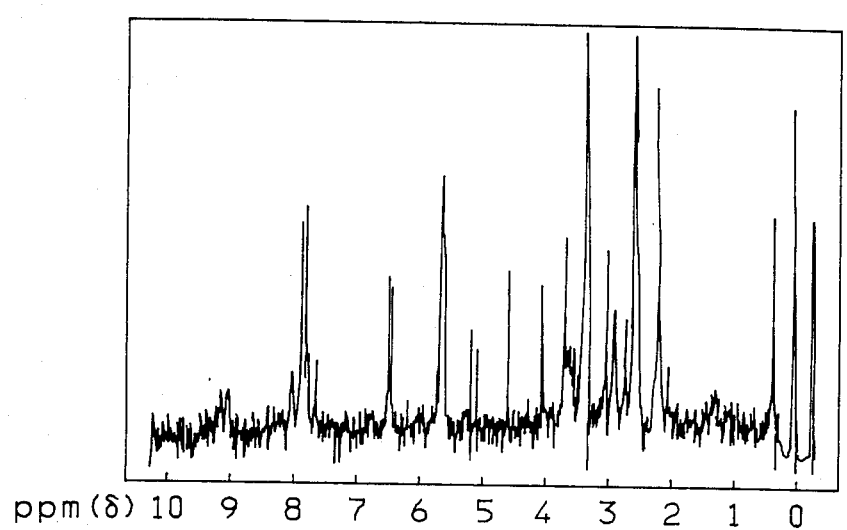
Figure 109:
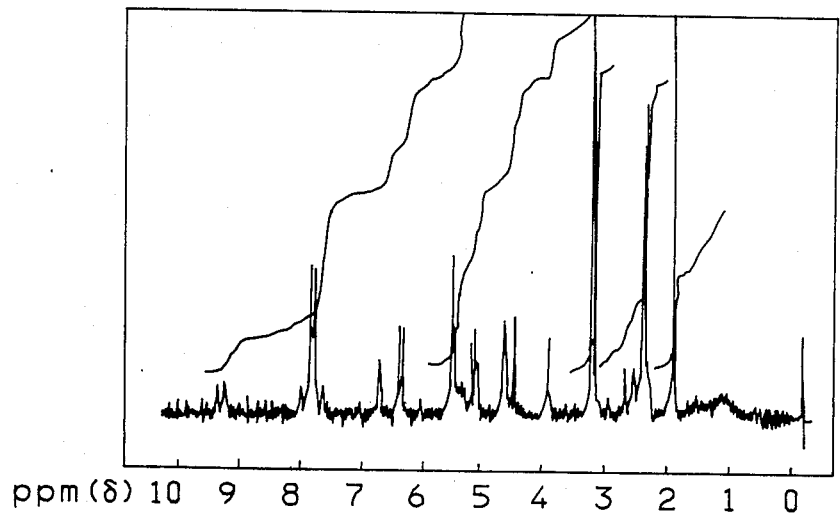
Figure 110:
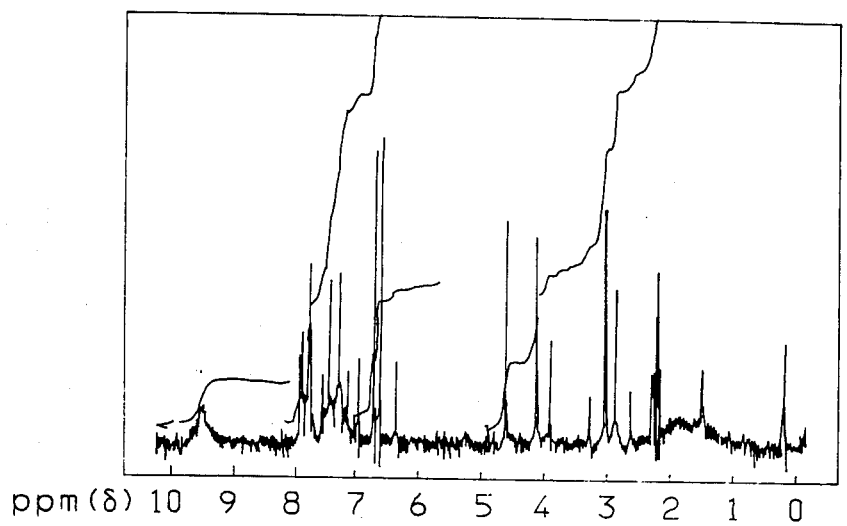

| No. of the compound of the present invention | A | Appearance | Melting point (°C.) | Infrared spectrum (KBr-method or Neat-method) | ¹H—nuclear magnetic resonance spectrum (Solvent) |
|---|---|---|---|---|---|
| 32 | (pyrrolidine with -CO-CH₂-phenyl) | oil | — | — | FIG. 106 (CDCl₃) |
| 33 | (β-lactam with S, CH₃, CH₃, -NH-, O=CO-CH₂CO-C₆H₄-Br) | acicular crystal | >100 (coloration) | FIG. 27 | FIG. 107 ((CD₃)₂CO) |
| 34 | (β-lactam with S, CH₃, =CH-CH₃, -NH-, O=CO-CH₂CO-C₆H₄-Br) | acicular crystal | — | — | FIG. 108 ((CD₃)₂CO + CD₂Cl₂) |
| 35 | (β-lactam with S, =CH-CH₃, CH₂O-CO-CH₃, -NH-, O=COCH₂CO-C₆H₄-Br) | acicular crystal | >100 (coloration) | FIG. 28 | FIG. 109 ((CD₃)₂CO + CD₂Cl₂) |
| 36 | —NH—C₆H₅ | acicular crystal | >154 (dec.) | FIG. 29 | FIG. 110 ((CD₃)₂CO + D₂O) |

TABLE 1-continued

[Structure: CN-substituted bicyclic compound with -CH=CH-C(=O)-A group]

Figure 30:
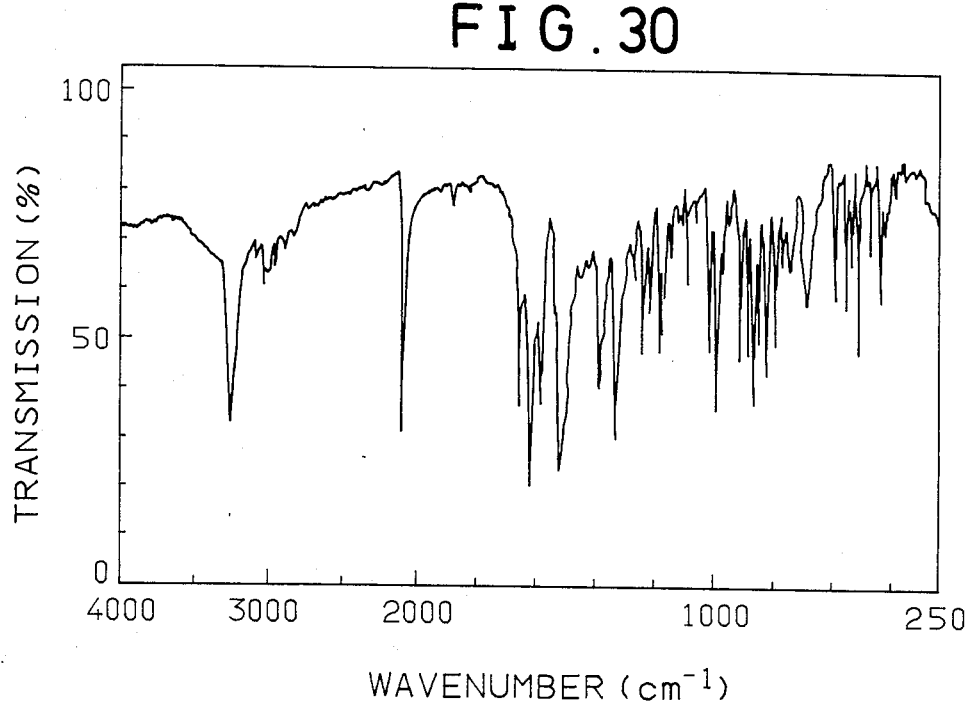
Figure 31:
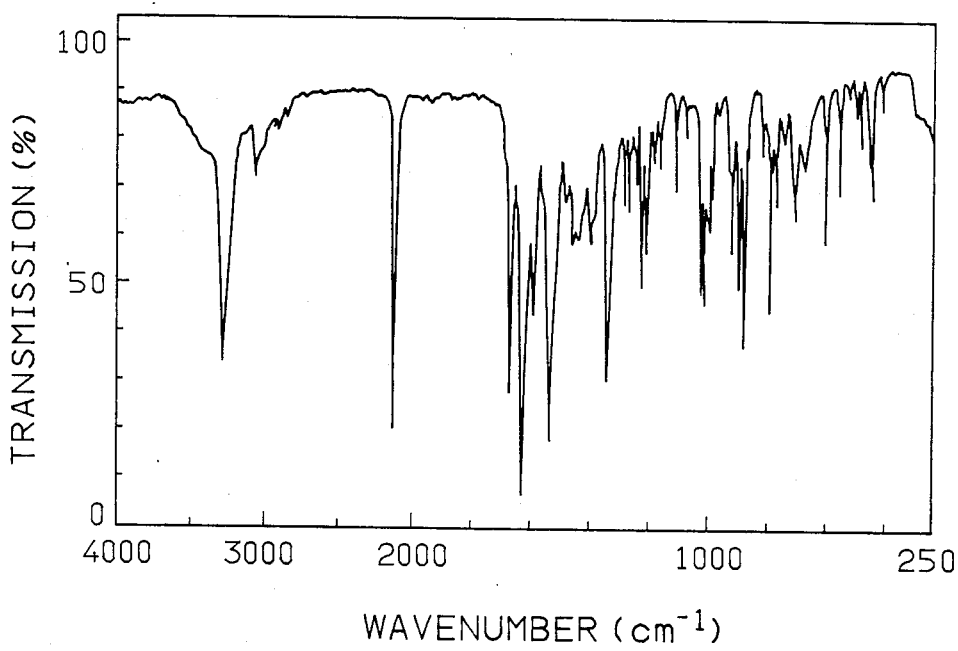
Figure 32:
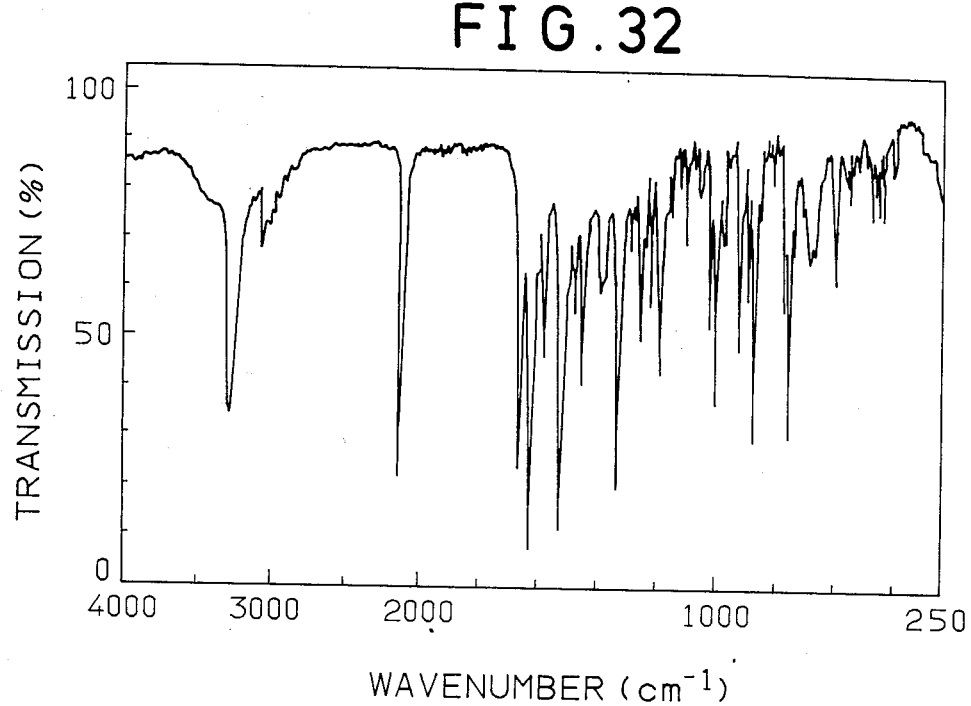
Figure 33:
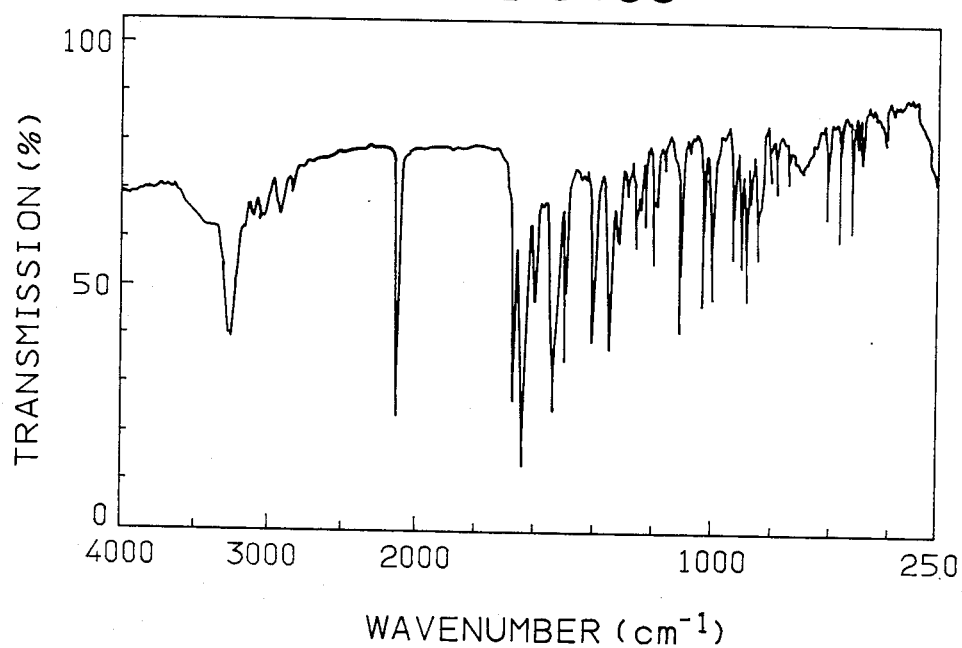
Figure 34:
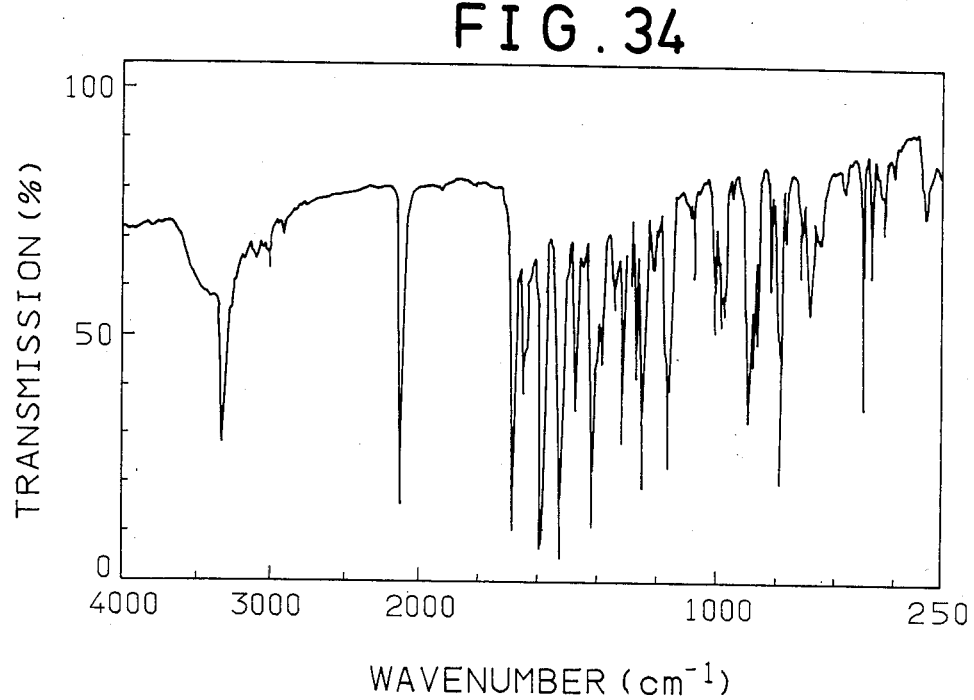
Figure 35:
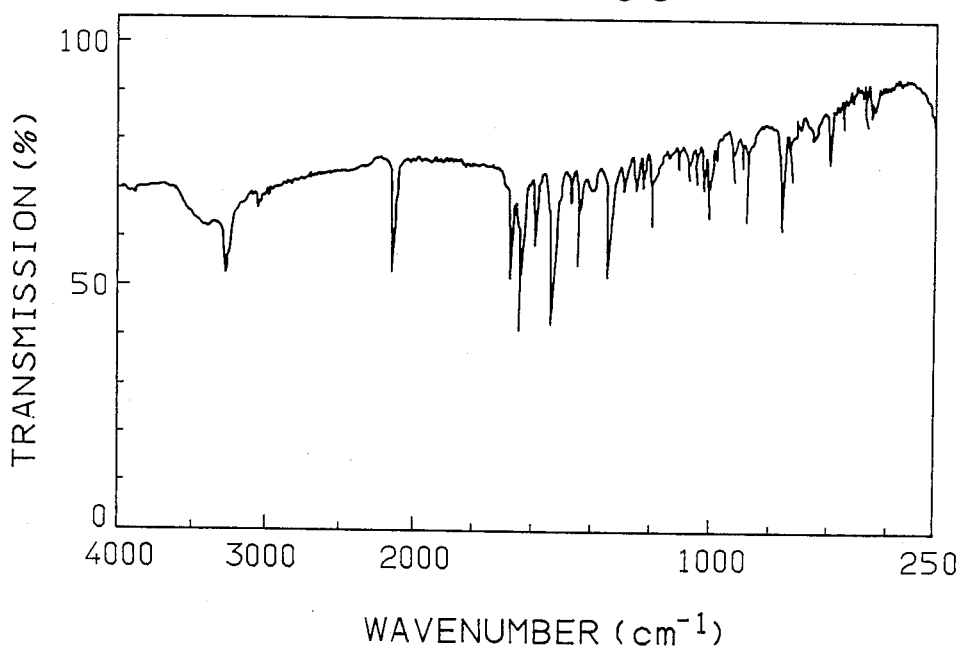
Figure 111:
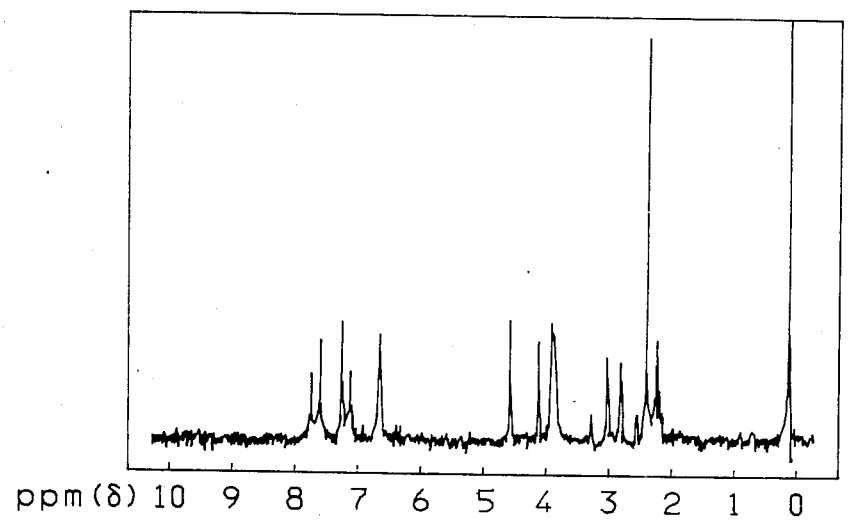
Figure 112:
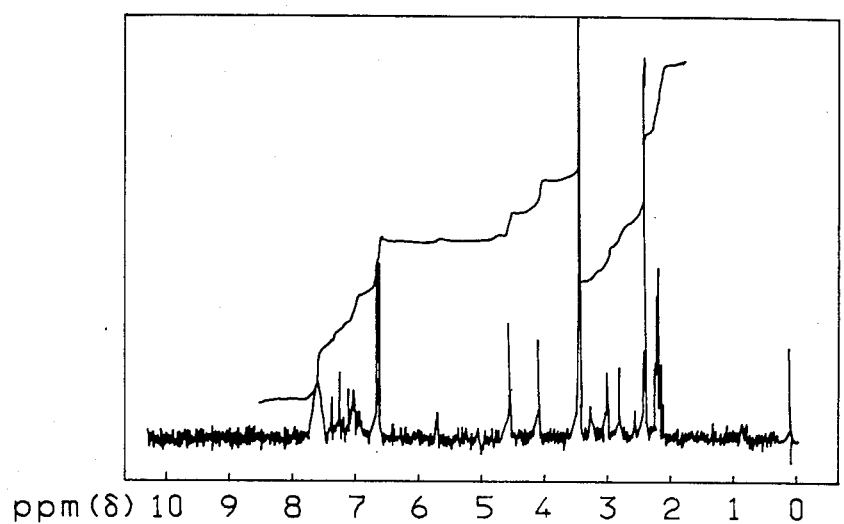
Figure 113:
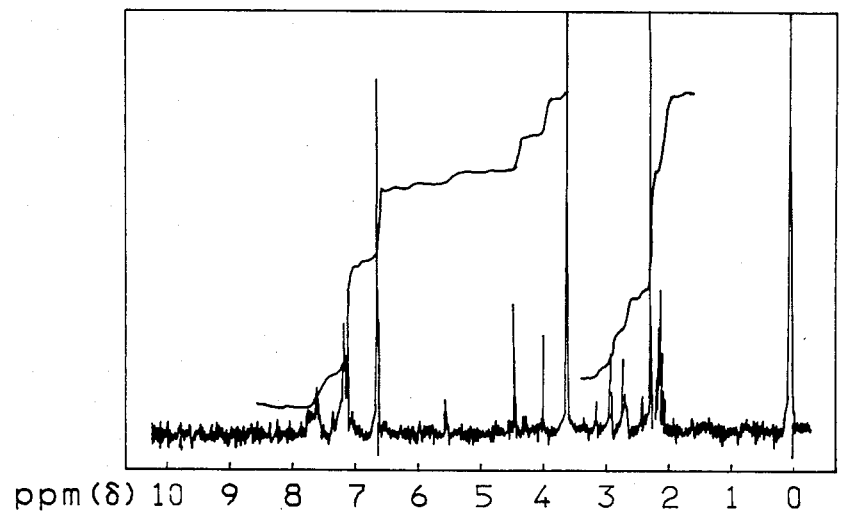
Figure 114:
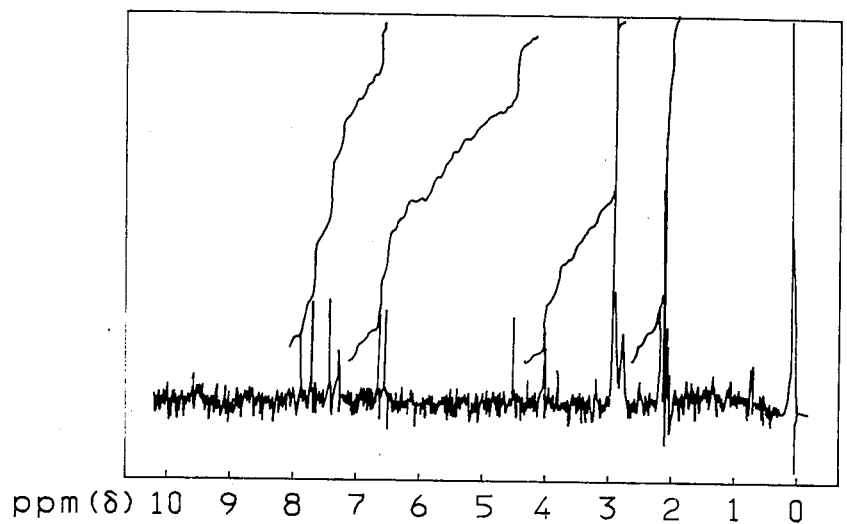
Figure 115:
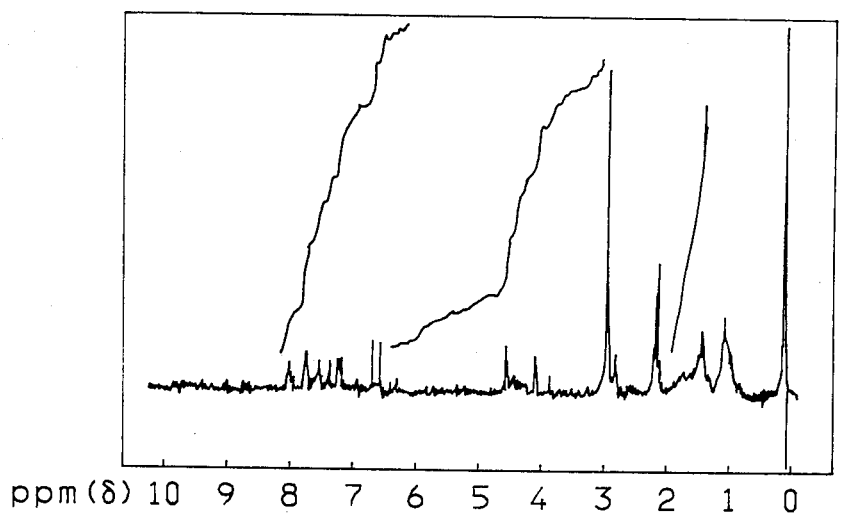
Figure 116:
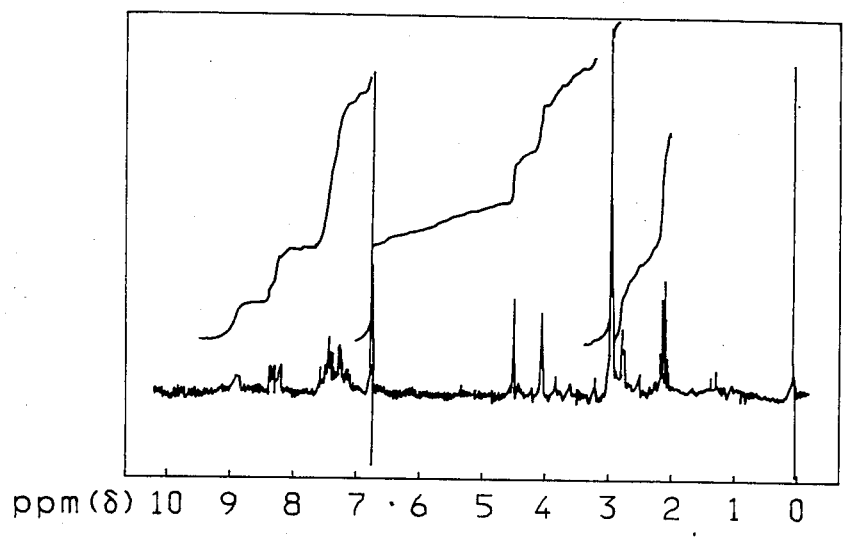

| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 37 | —NH—C$_6$H$_4$—CH$_3$ (para) | acicular crystal | >160 (coloration) | FIG. 30 | FIG. 111 ((CD$_3$)$_2$CO + D$_2$O) |
| 38 | —NH—C$_6$H$_4$—CH$_3$ (meta) | acicular crystal | >150 (coloration) | FIG. 31 | FIG. 112 ((CD$_3$)$_2$CO + D$_2$O) |
| 39 | —NH—C$_6$H$_4$—CH$_3$ (ortho) | acicular crystal | >120 (coloration) | FIG. 32 | FIG. 113 ((CD$_3$)$_2$CO + CD$_2$Cl$_2$ + D$_2$O) |
| 40 | —NH—C$_6$H$_4$—Cl (para) | acicular crystal | >157 (coloration) | FIG. 33 | FIG. 114 ((CD$_3$)$_2$CO) |
| 41 | —NH—C$_6$H$_4$—Cl (meta) | acicular crystal | >160 (coloration) | FIG. 34 | FIG. 115 ((CD$_3$)$_2$CO) |
| 42 | —NH—C$_6$H$_4$—Cl (ortho) | acicular crystal | >148 (coloration) | FIG. 35 | FIG. 116 ((CD$_3$)$_2$CO) |

TABLE 1-continued

Figure 36:
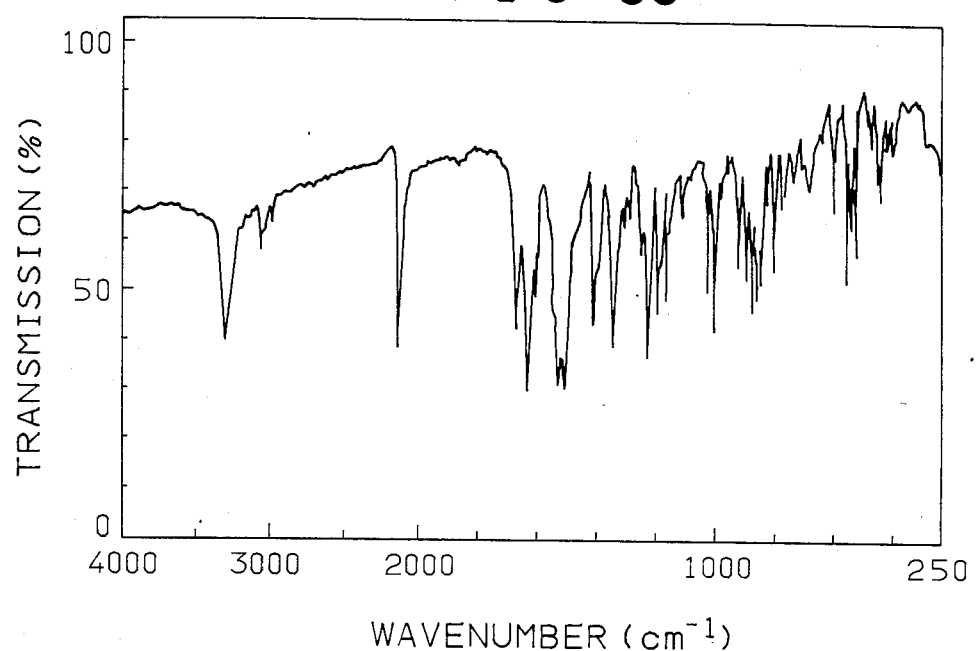
Figure 37:
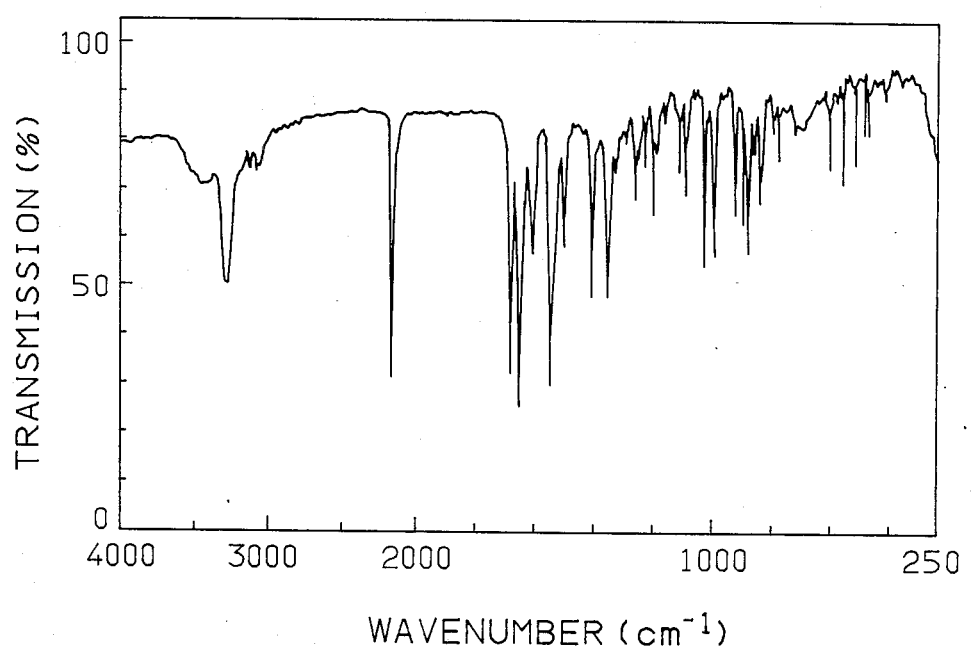
Figure 38:
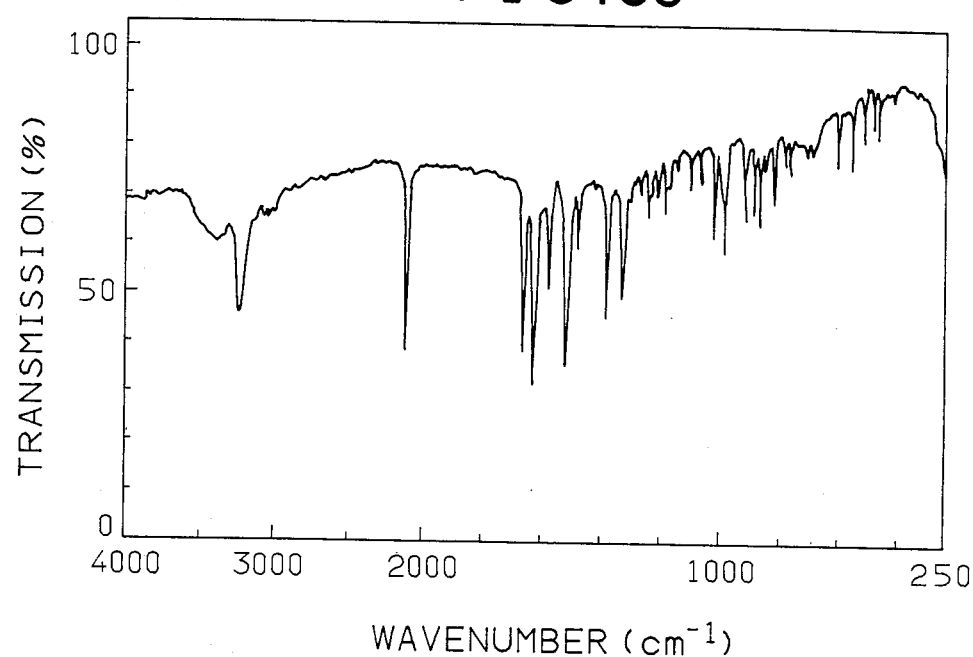
Figure 39:
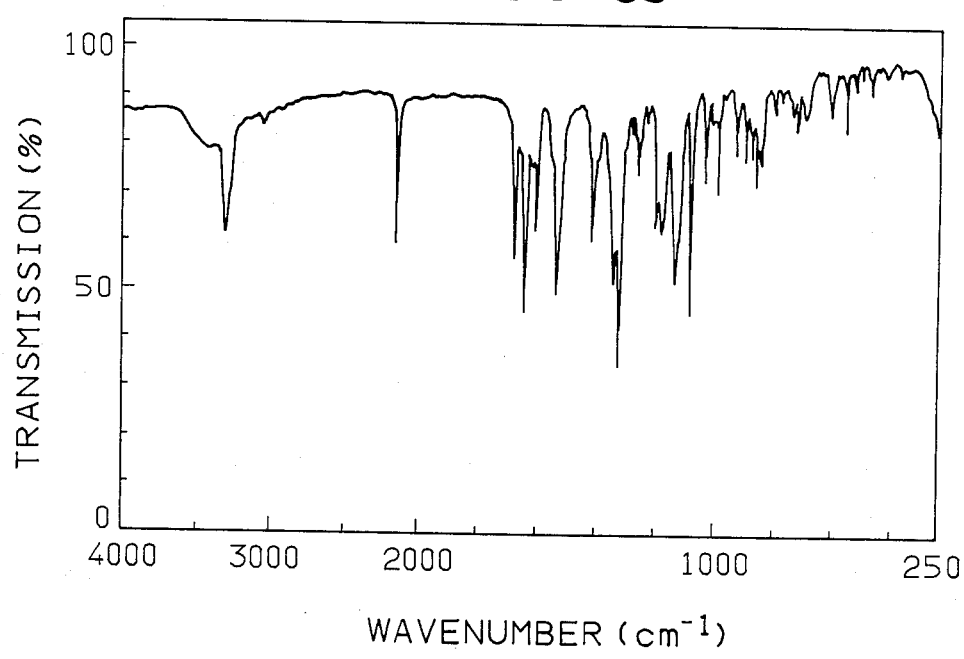
Figure 40:
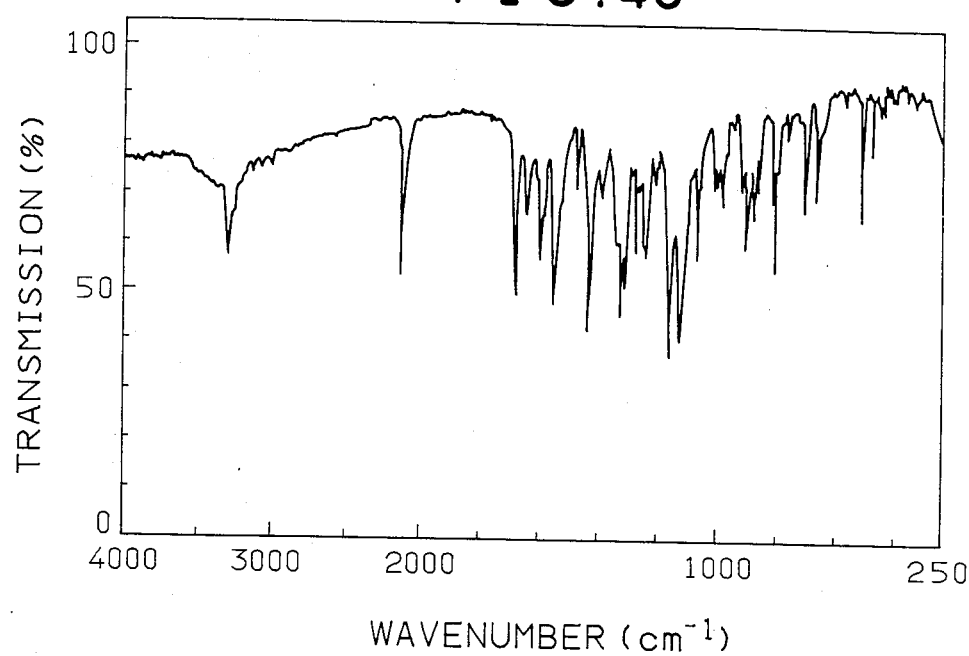
Figure 41:
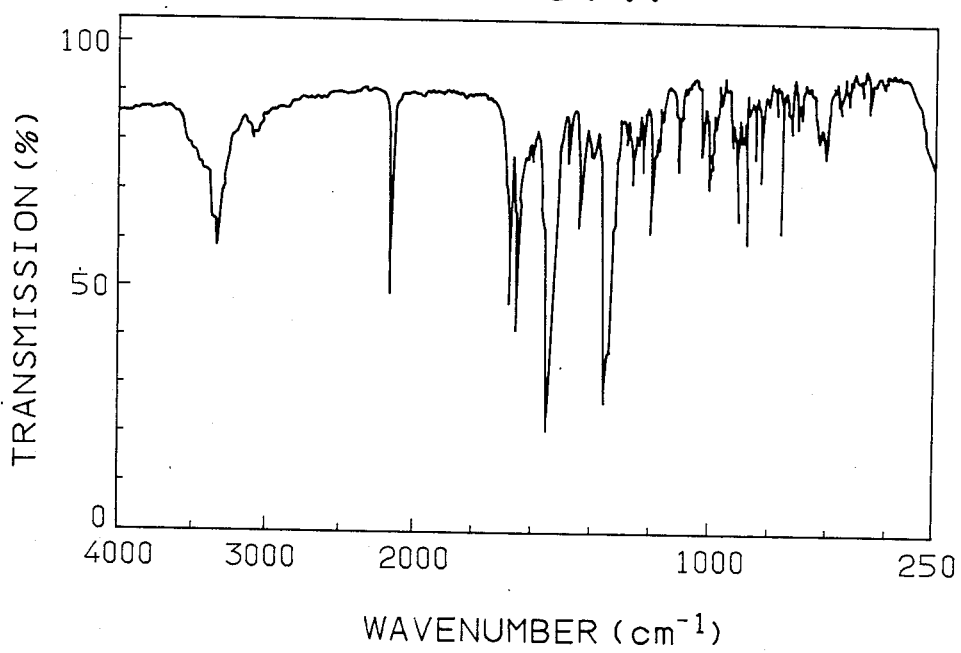
Figure 42:
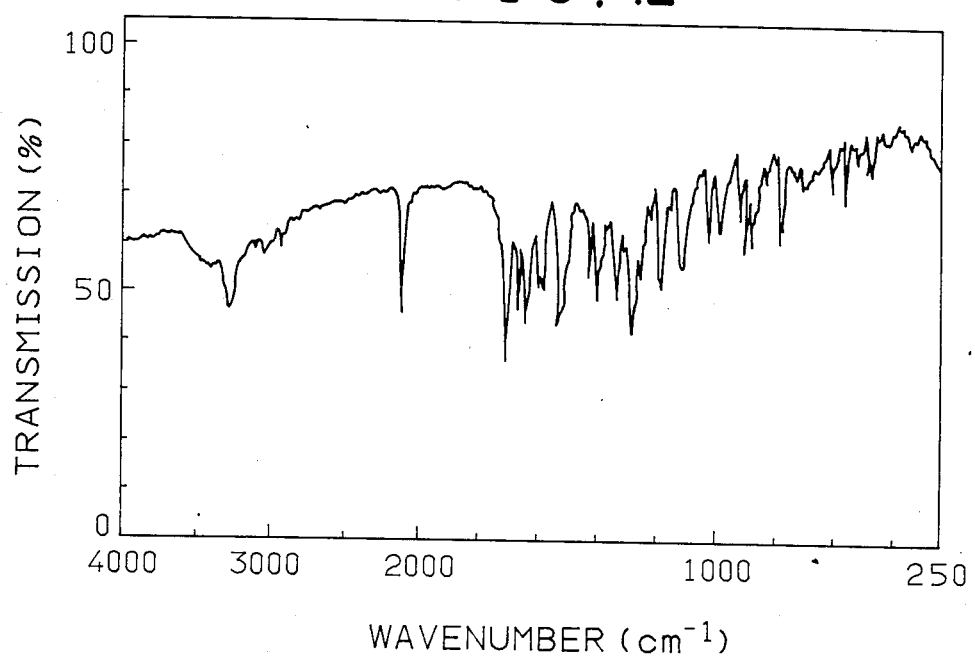
Figure 117:
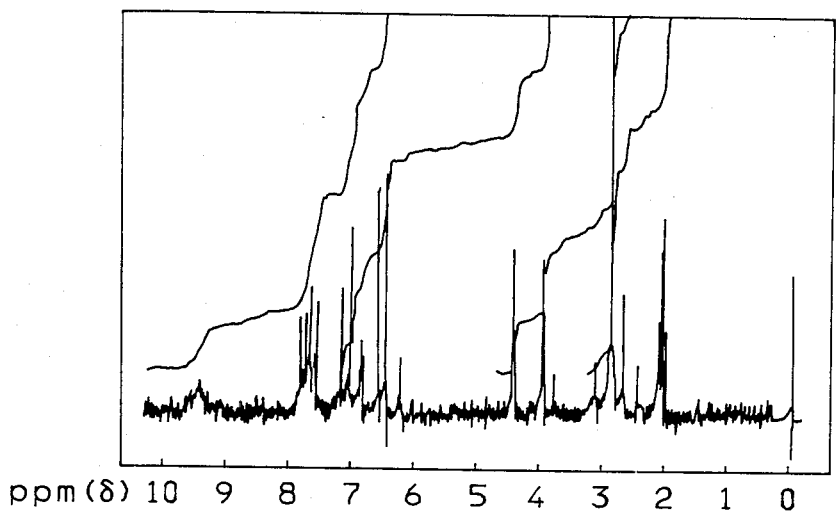
Figure 118:
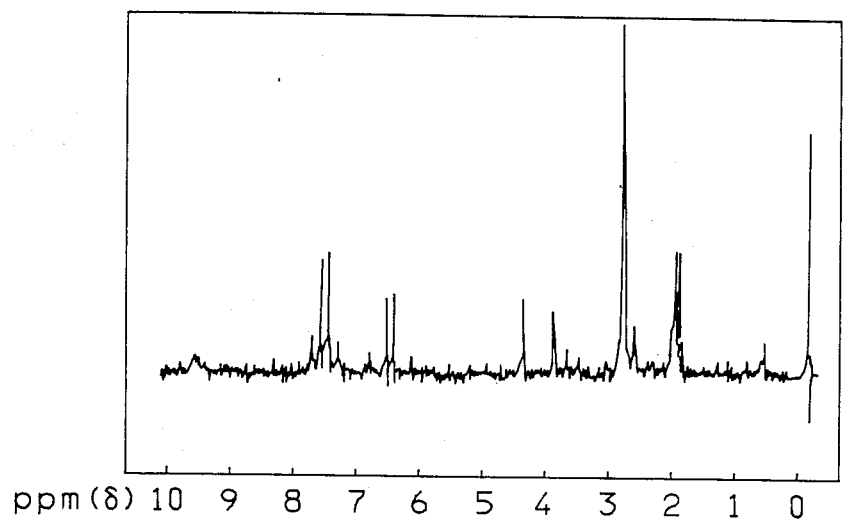
Figure 119:
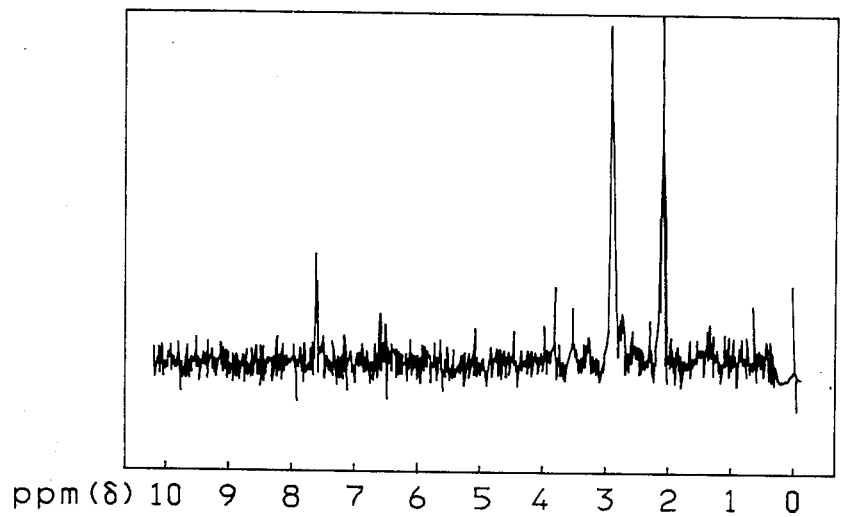
Figure 120:
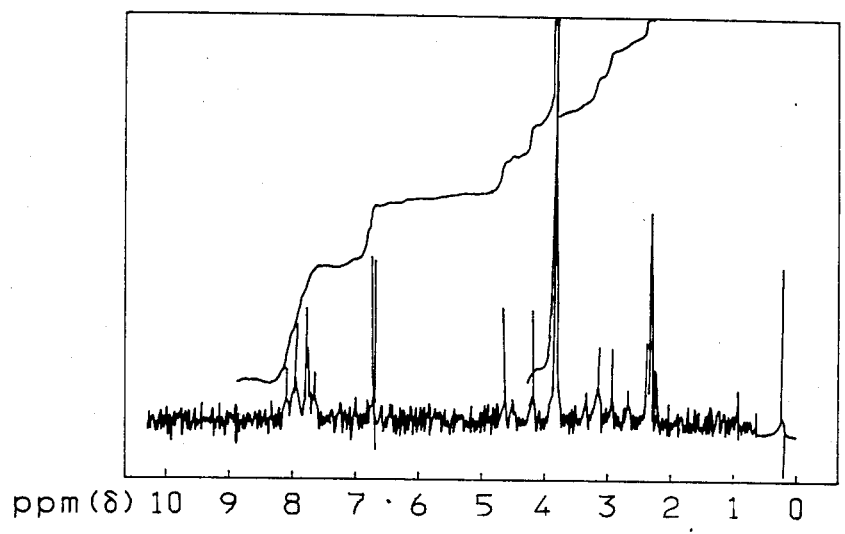
Figure 121:
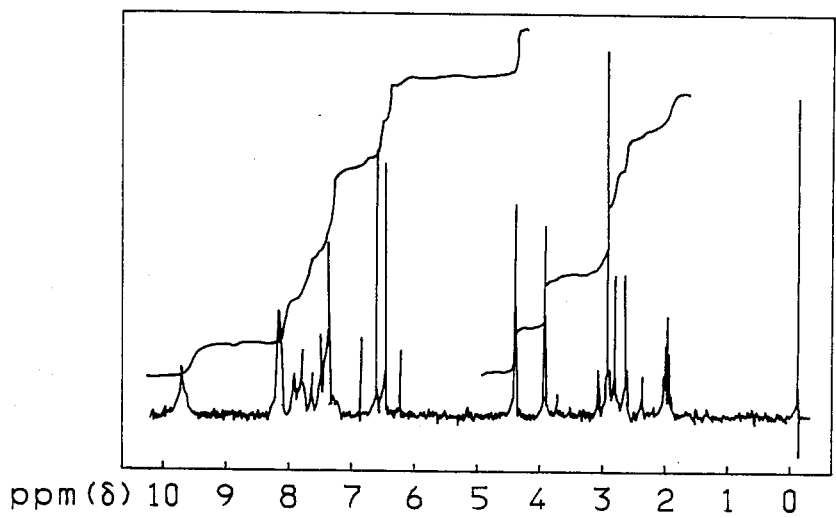
Figure 122:
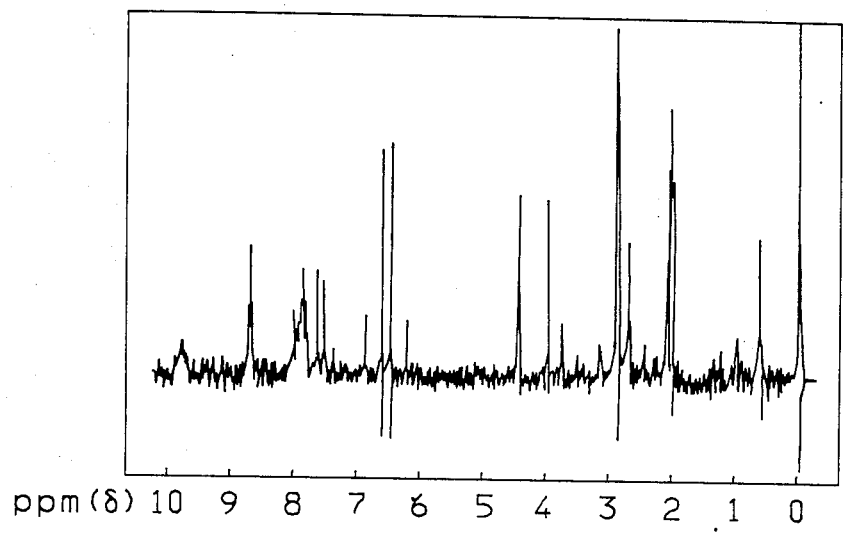
Figure 123:
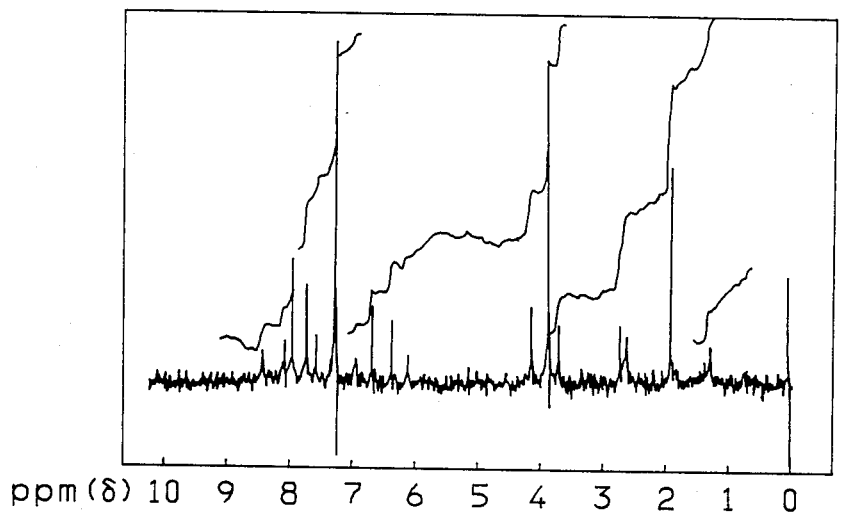

| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 43 | —NH—C₆H₄—F (p) | micro-acicular crystal | >160 (dec.) | FIG. 36 | FIG. 117 ((CD₃)₂CO) |
| 44 | —NH—C₆H₄—Br (p) | acicular crystal | >165 (coloration) | FIG. 37 | FIG. 118 ((CD₃)₂CO) |
| 45 | —NH—C₆H₄—I (p) | acicular crystal | >164 | FIG. 38 | FIG. 119 ((CD₃)₂CO) |
| 46 | —NH—C₆H₄—CF₃ (p) | acicular crystal | >140 (decom. coloration) not melting | FIG. 39 | FIG. 120 ((CD₃)₂CO + D₂O) |
| 47 | —NH—C₆H₄—CF₃ (m) | acicular crystal | >145 (decom. coloration) | FIG. 40 | FIG. 121 ((CD₃)₂CO) |
| 48 | —NH—C₆H₄—NO₂ (m) | acicular crystal | >140 (coloration) Not melting | FIG. 41 | FIG. 122 ((CD₃)₂CO) |
| 49 | —NH—C₆H₄—COOCH₃ (p) | acicular crystal | >131 (coloration) | FIG. 42 | FIG. 123 ((CD₃)₂CO + CDCl₃) |

TABLE 1-continued

Figure 43:
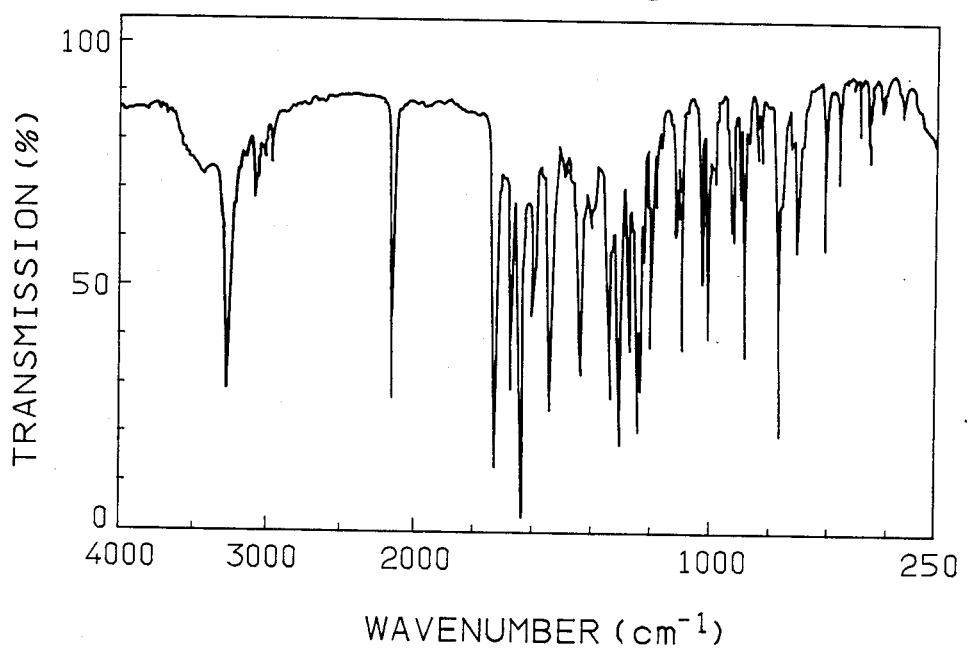
Figure 44:
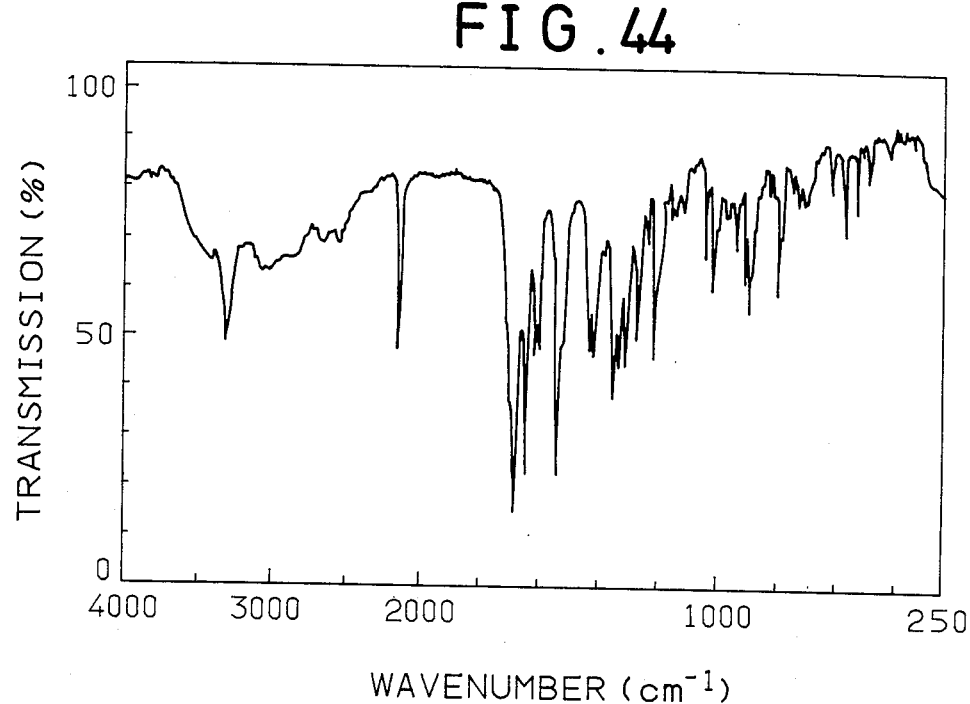
Figure 45:
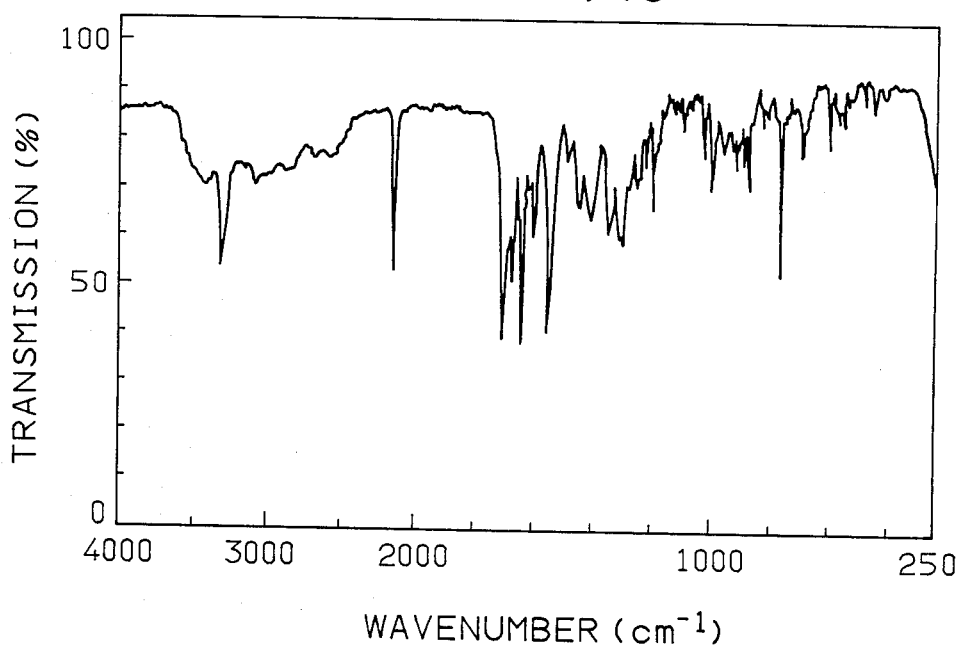
Figure 46:
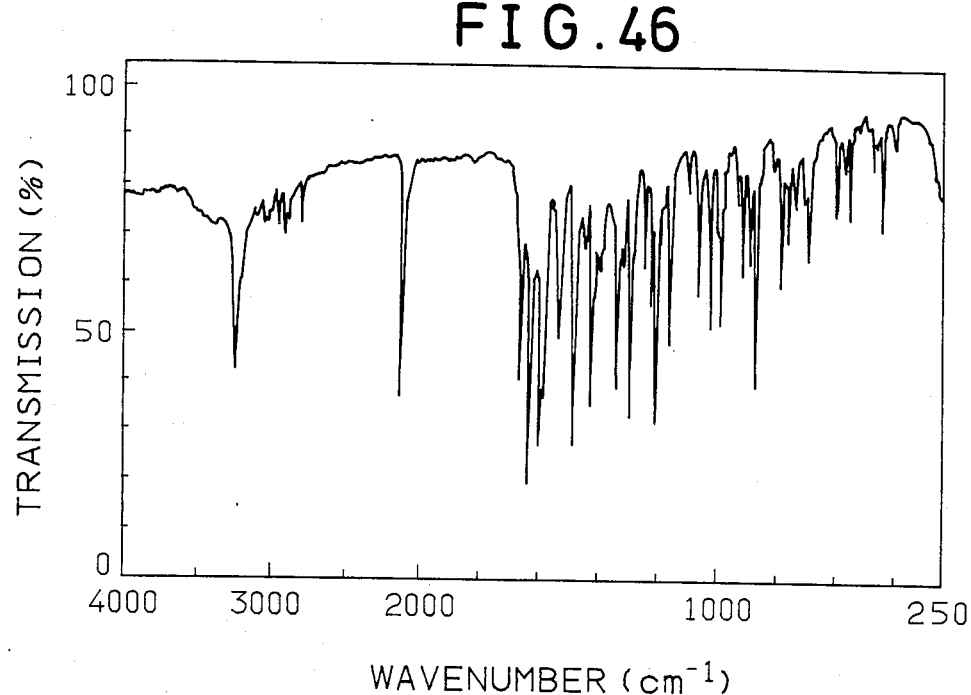
Figure 47:
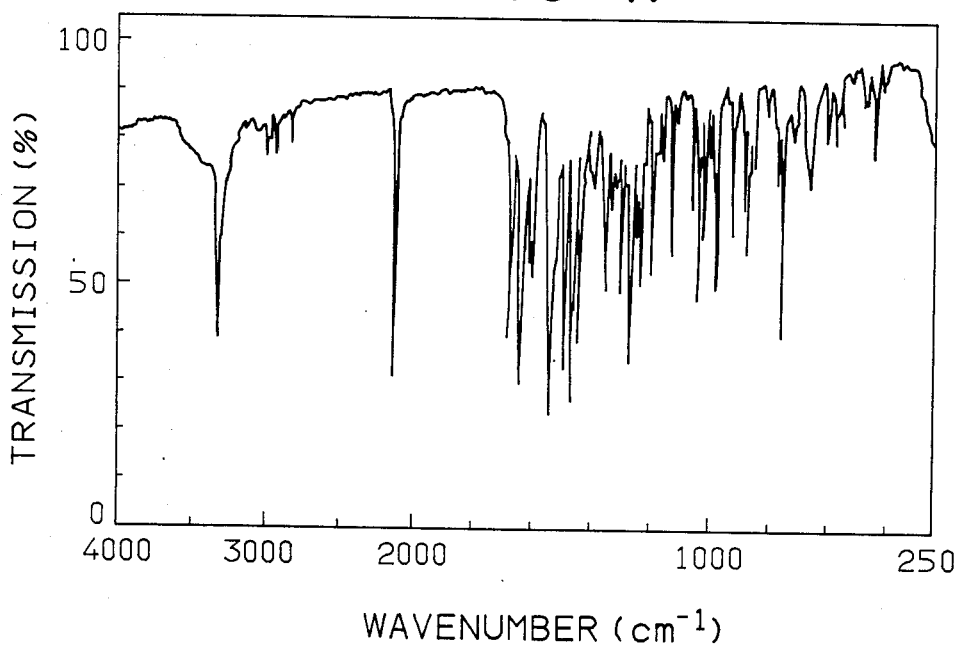
Figure 124:
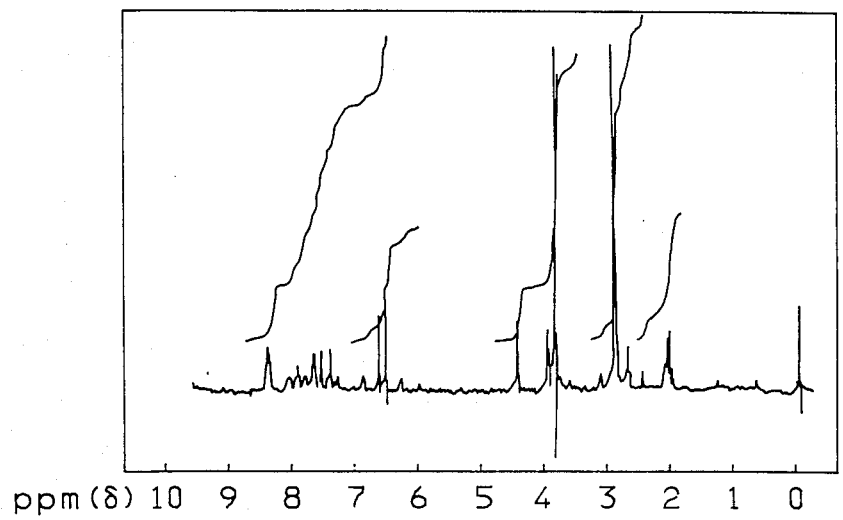
Figure 125:
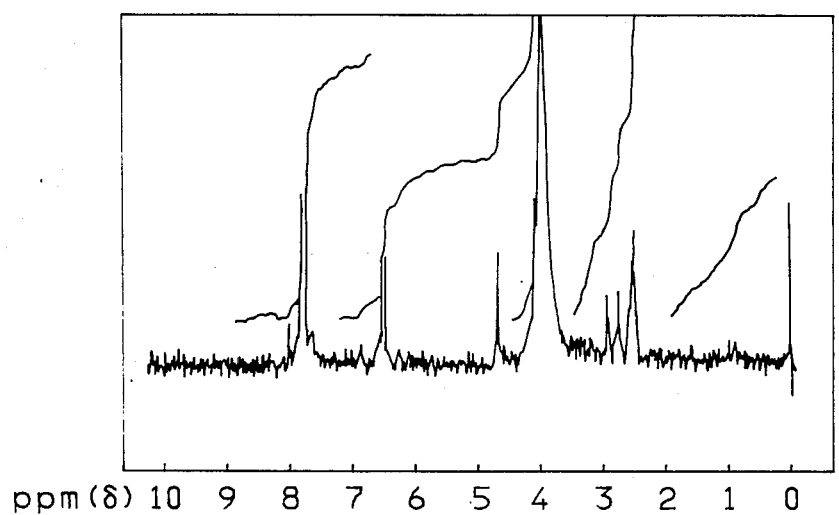
Figure 126:
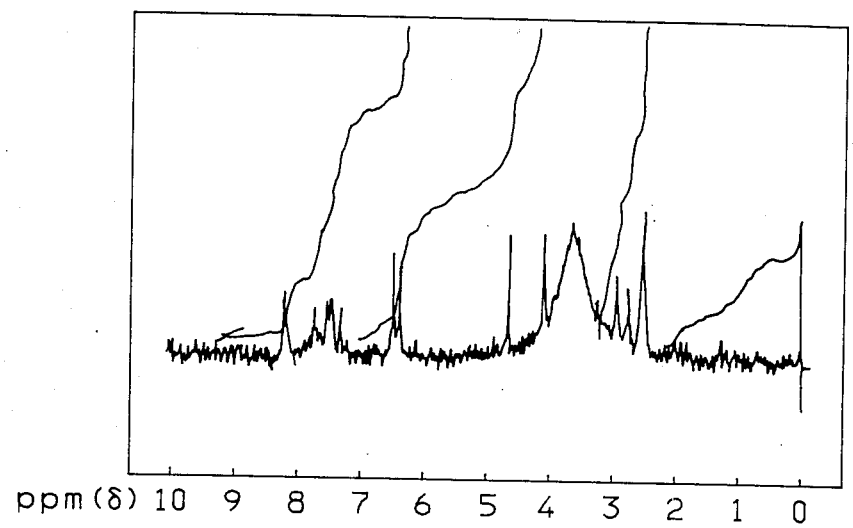
Figure 127:
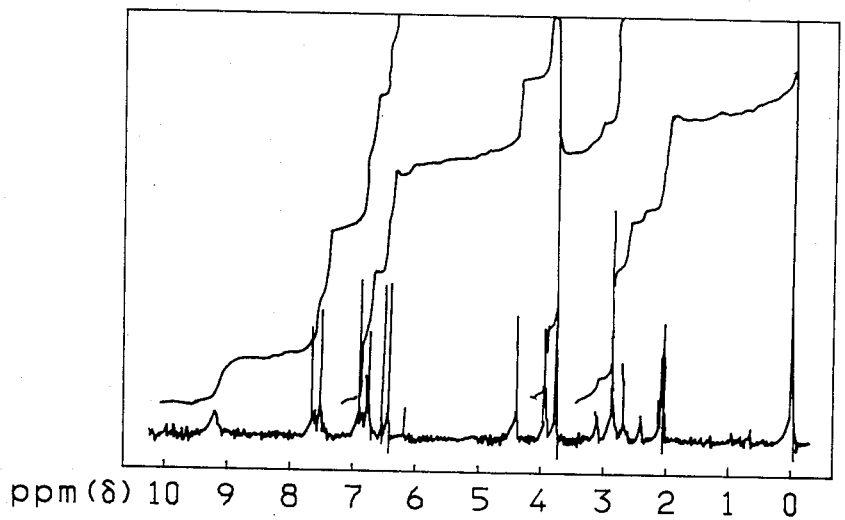
Figure 128:
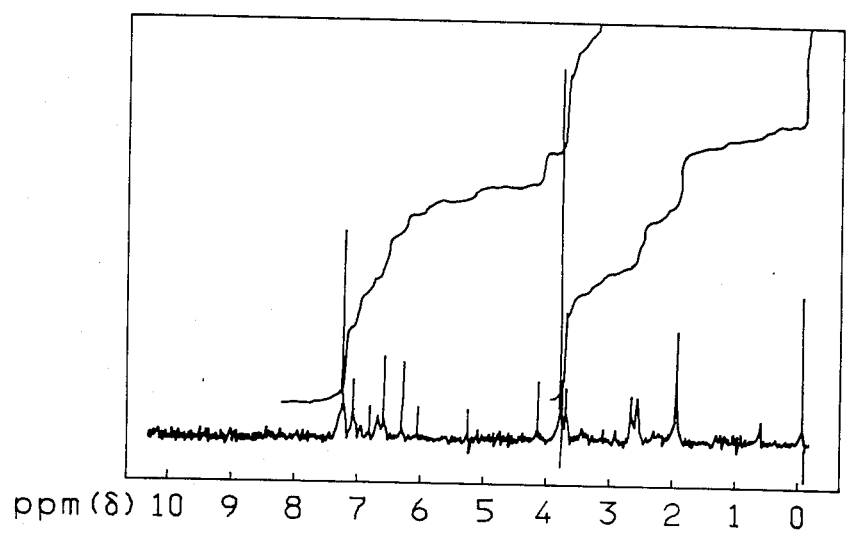
Figure 129:
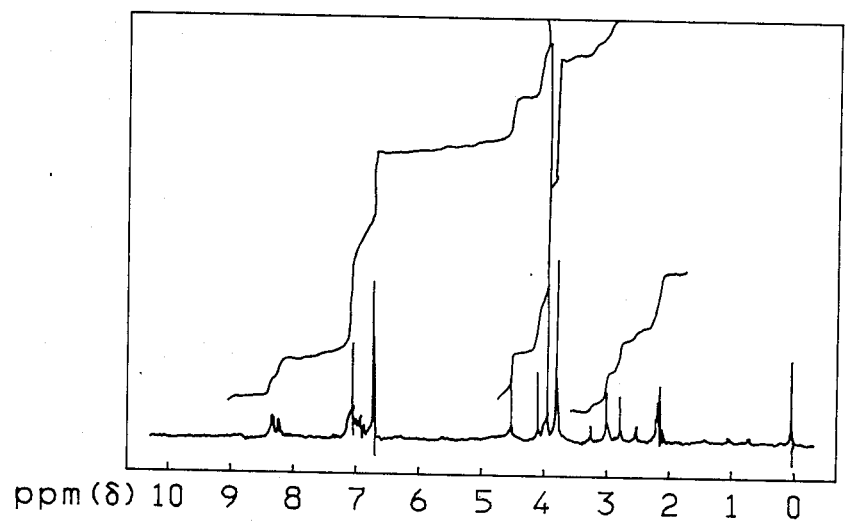

| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 50 | —NH—(phenyl)-COOCH$_3$ (meta) | acicular crystal | >150 (coloration) | FIG. 43 | FIG. 124 ((CD$_3$)$_2$CO) |
| 51 | —NH—(phenyl)-COOH (para) | micro-acicular crystal | >110 (coloration) | FIG. 44 | FIG. 125 ((CD$_3$)$_2$CO) |
| 52 | —NH—(phenyl)-COOH (meta) | micro-acicular crystal | 125 (coloration) | FIG. 45 | FIG. 126 ((CD$_3$)$_2$CO) |
| 53 | —NH—(phenyl)-OCH$_3$ (para) | acicular crystal | >160 (decomp. and coloration) | — | FIG. 127 ((CD$_3$)$_2$CO) |
| 54 | —NH—(phenyl)-OCH$_3$ (meta) | acicular crystal | >165 (decomp. and coloration) | FIG. 46 | FIG. 128 (CDCl$_3$ + CD$_3$OD) |
| 55 | —NH—(phenyl)-OCH$_3$ (ortho) | acicular crystal | >134 (coloration) | FIG. 47 | FIG. 129 ((CD$_3$)$_2$CO + D$_2$O) |

TABLE 1-continued

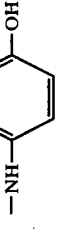

Figure 48:
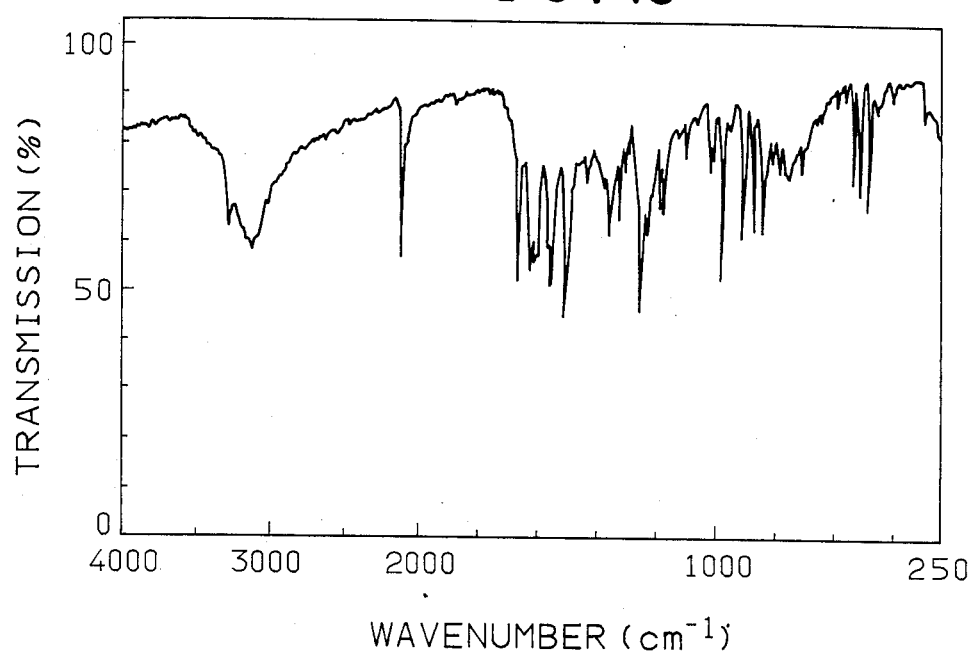
Figure 49:
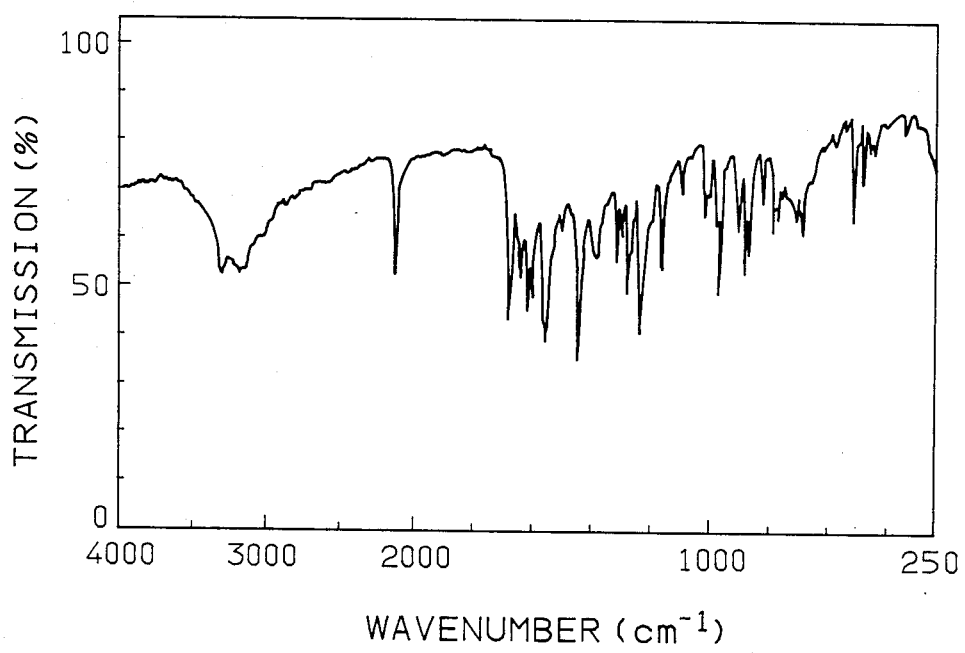
Figure 50:
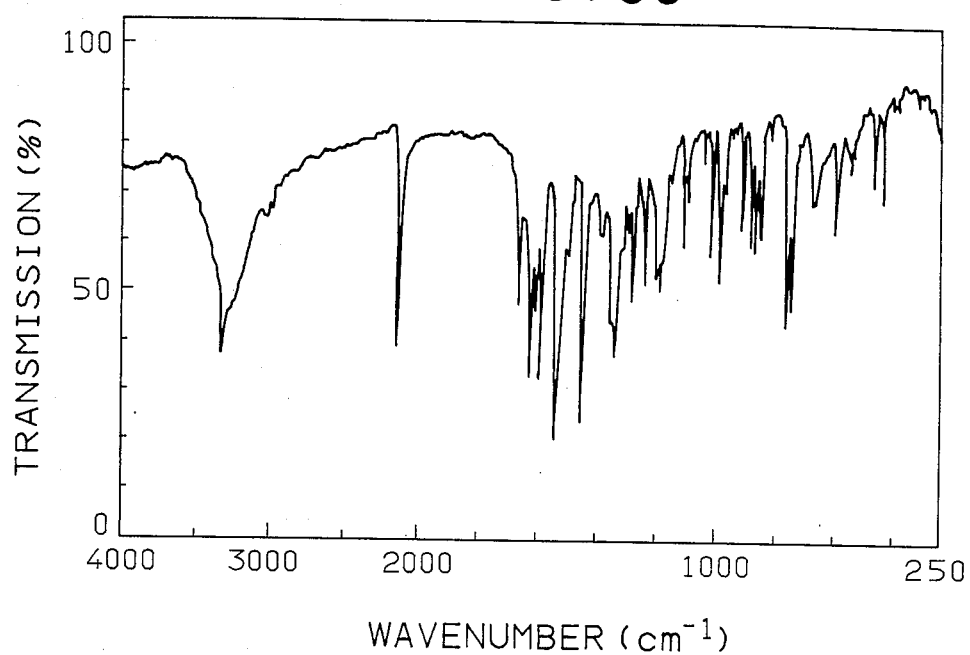
Figure 51:
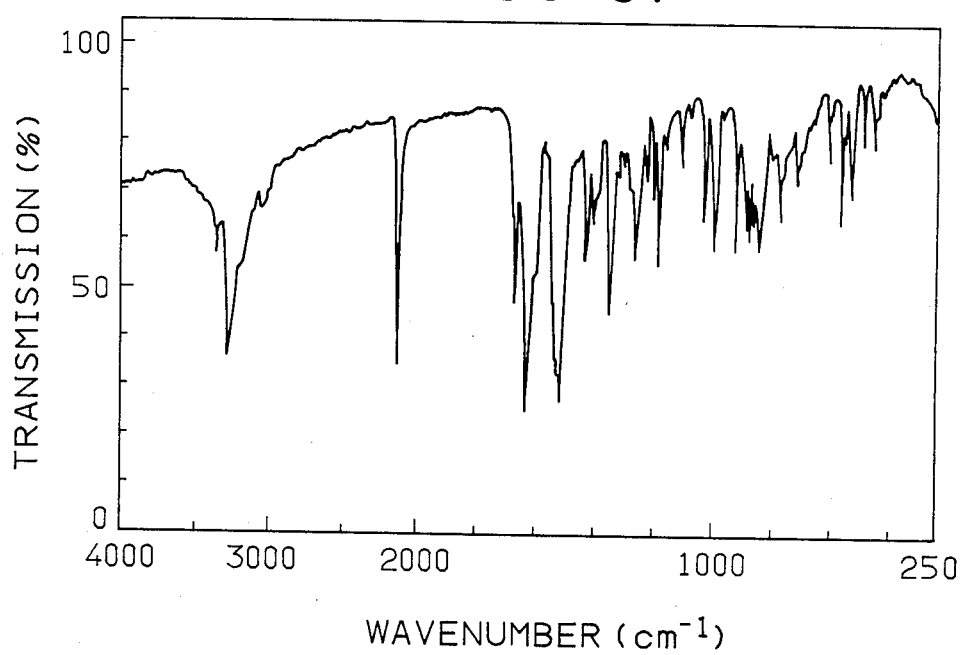
Figure 52:
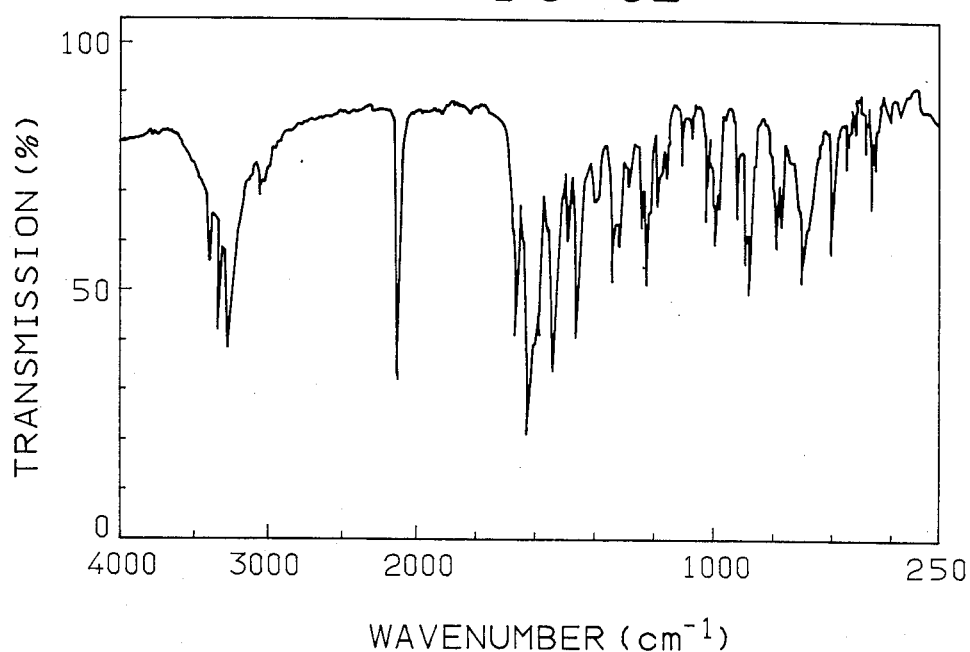
Figure 53:
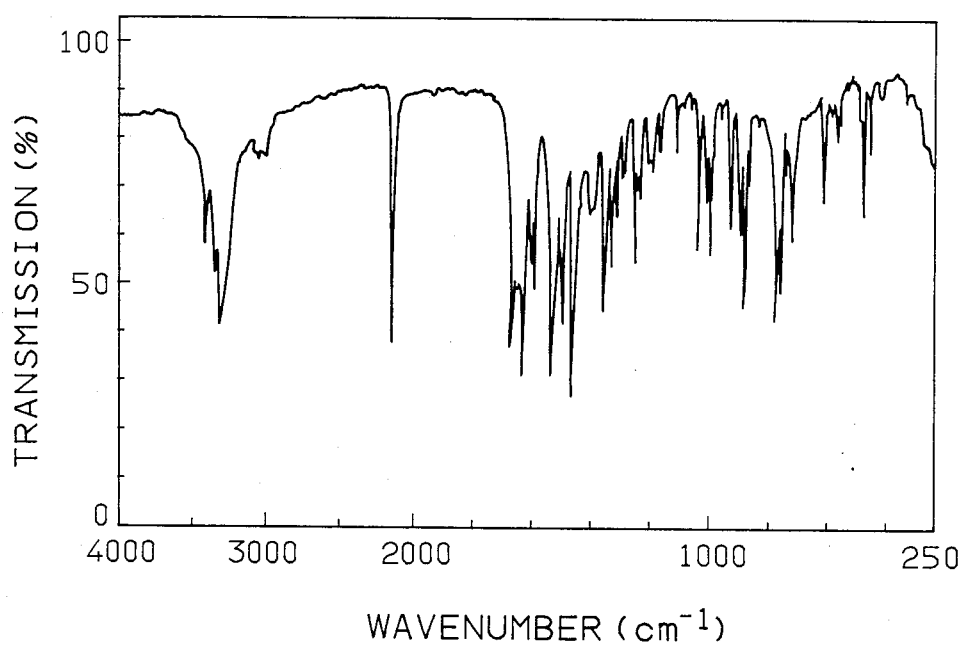
Figure 130:
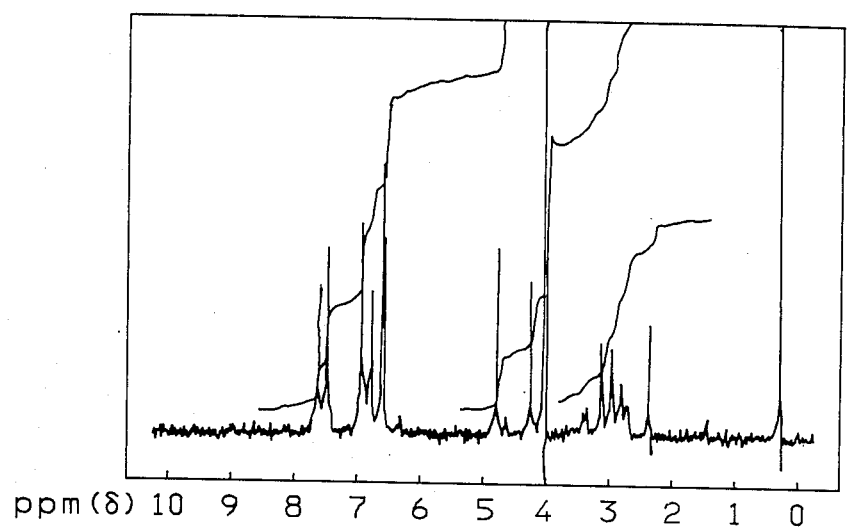
Figure 131:
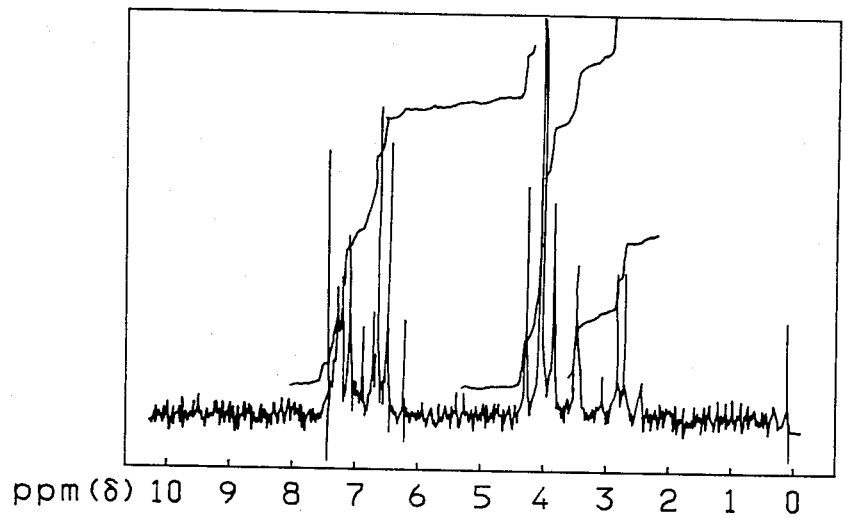
Figure 132:
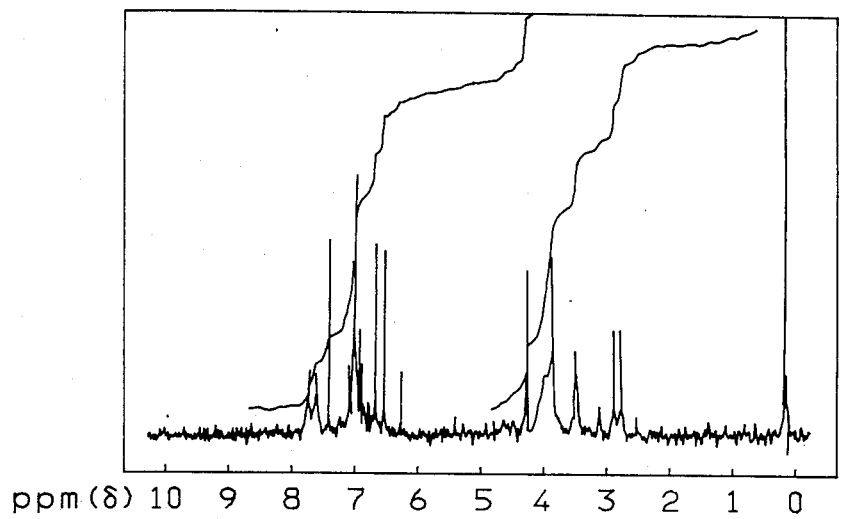
Figure 133:
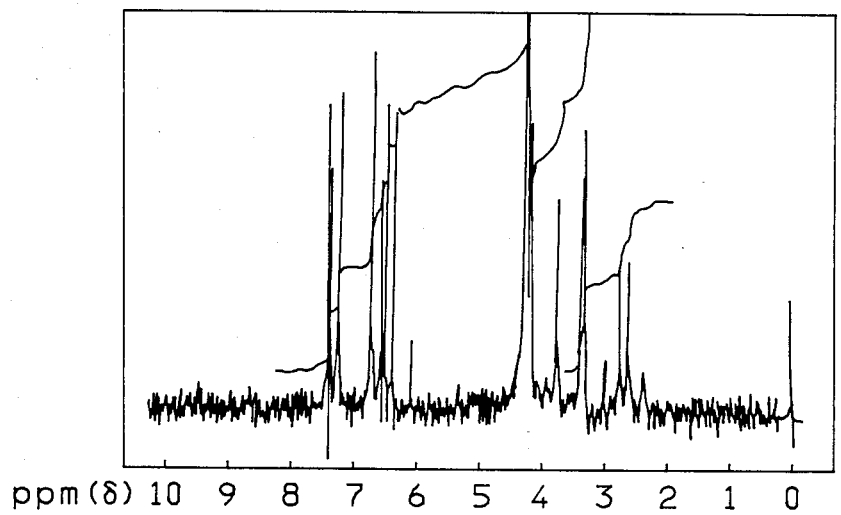
Figure 134:
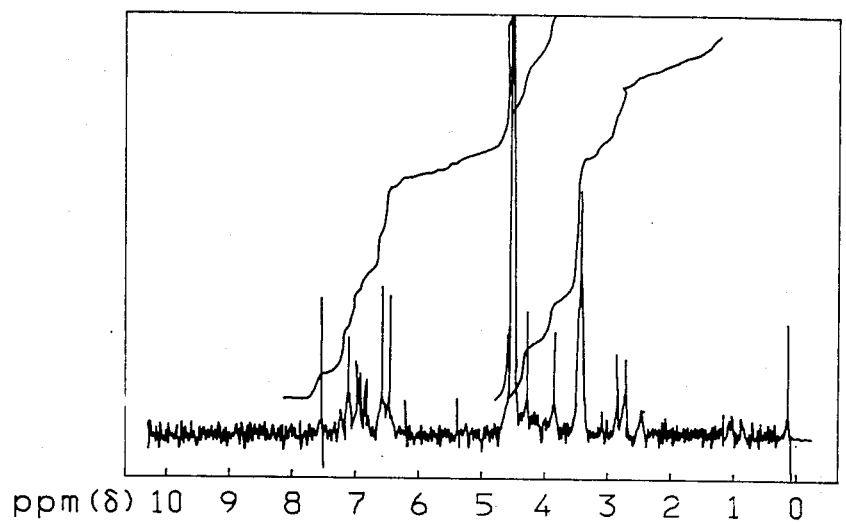
Figure 135:
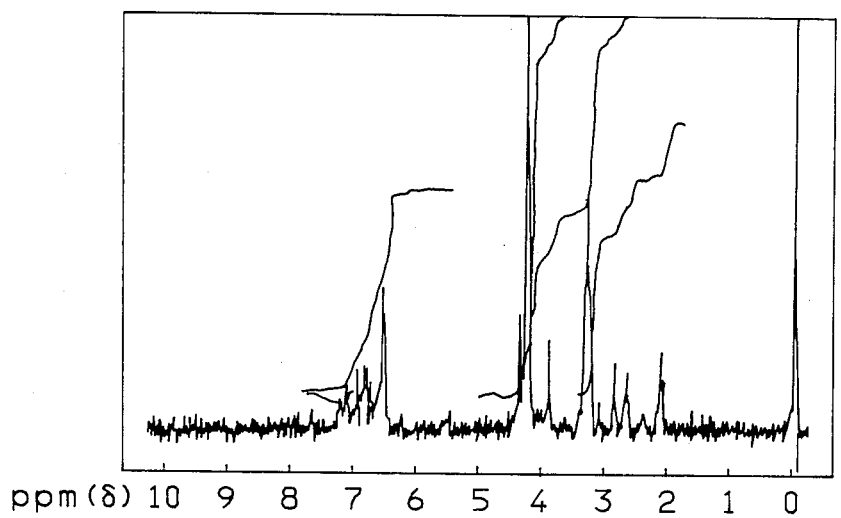

| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 56 | 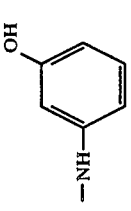 | micro-acicular crystal | >180 (decom. and coloration) | FIG. 48 | FIG. 130 ((CD$_3$)$_2$CO + D$_2$O) |
| 57 | 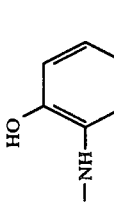 | micro-acicular crystal | >170 (decomp. and coloration) | FIG. 49 | FIG. 131 (CDCl$_3$ + CD$_3$OD) |
| 58 | 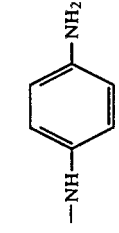 | micro-acicular crystal | >145 (decomp. and coloration) | FIG. 50 | FIG. 132 (CDCl$_3$ + CD$_3$OD + D$_2$O) |
| 59 | 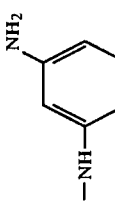 | micro-acicular crystal | >170 (decomp. and coloration) | FIG. 51 | FIG. 133 (CDCl$_3$ + CD$_3$OD) |
| 60 | 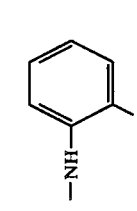 | micro-acicular crystal | >165 (decomp. and coloration) | FIG. 52 | FIG. 134 (CDCl$_3$ + CD$_3$OD) |
| 61 |  | micro-acicular crystal | >140 (decomp. and coloration) | FIG. 53 | FIG. 135 ((CD$_3$)$_2$CO + CD$_3$OD) |

TABLE 1-continued

![structure: CN and O-containing ring with CH=CH-C(=O)-A substituent]

Figure 54:
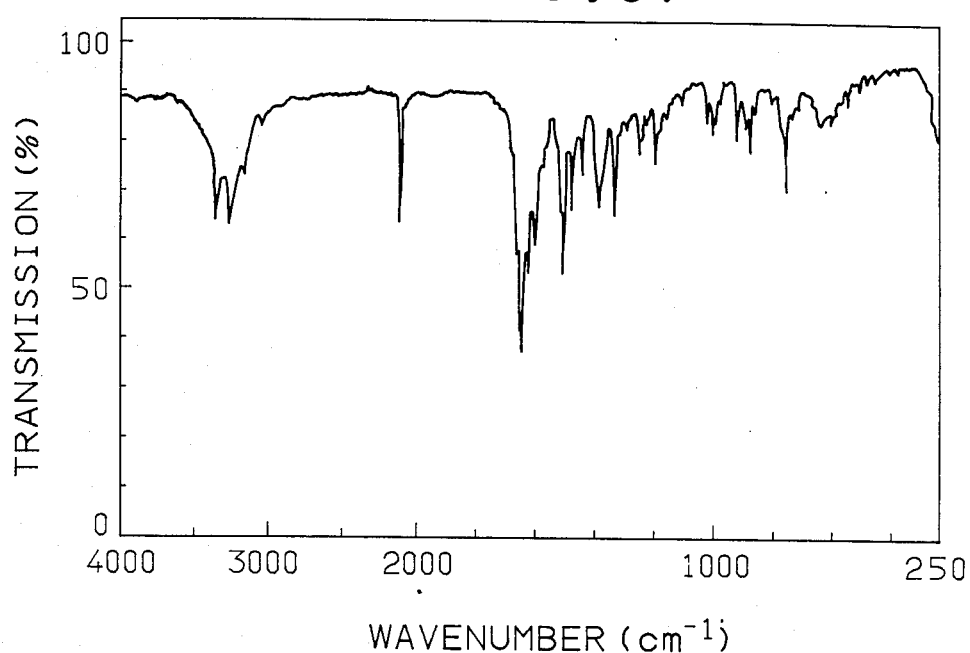
Figure 55:
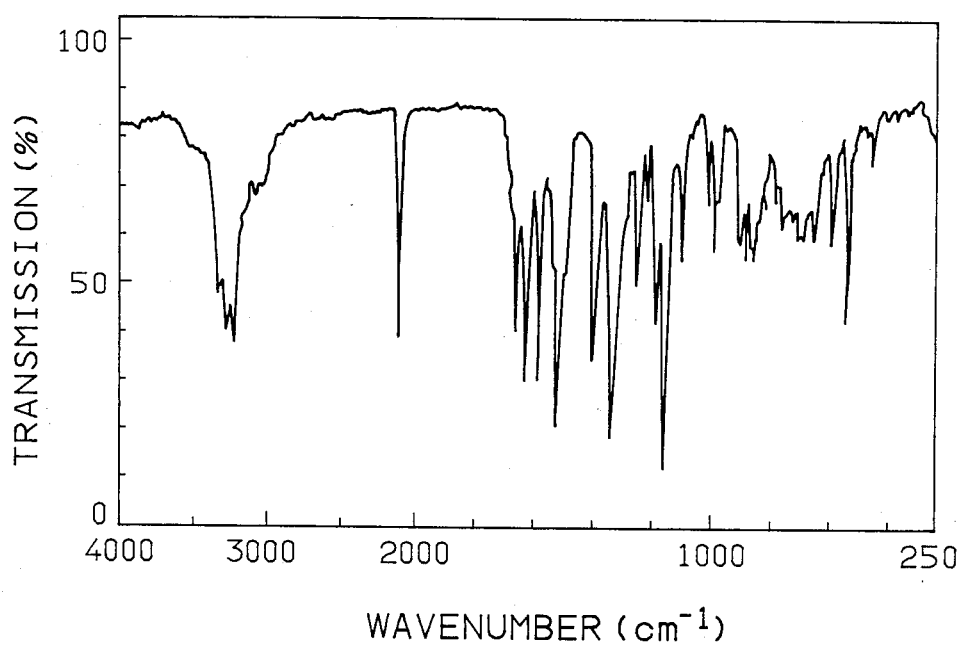
Figure 56:
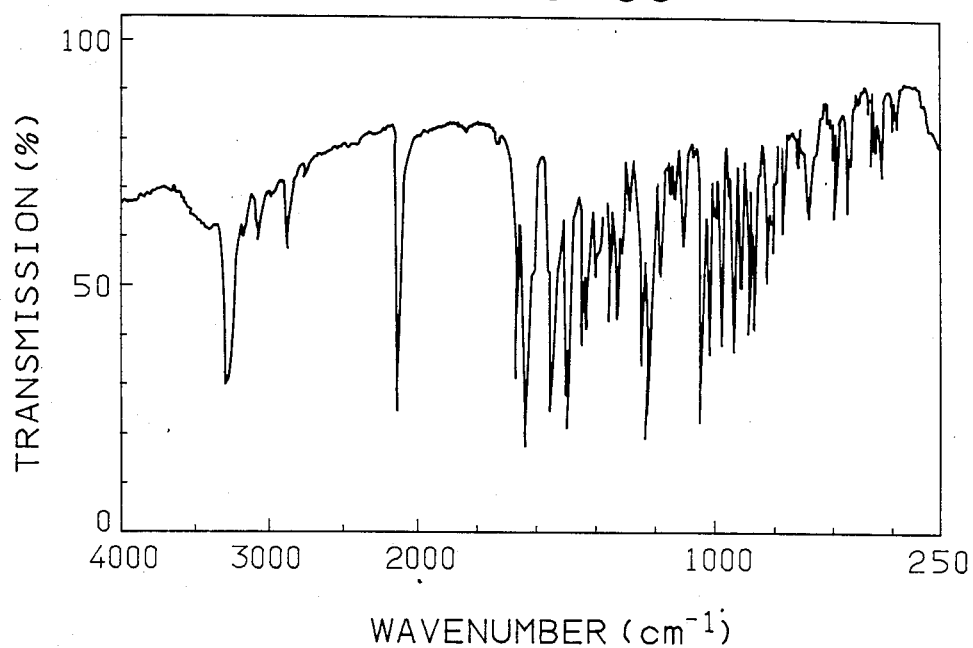
Figure 57:
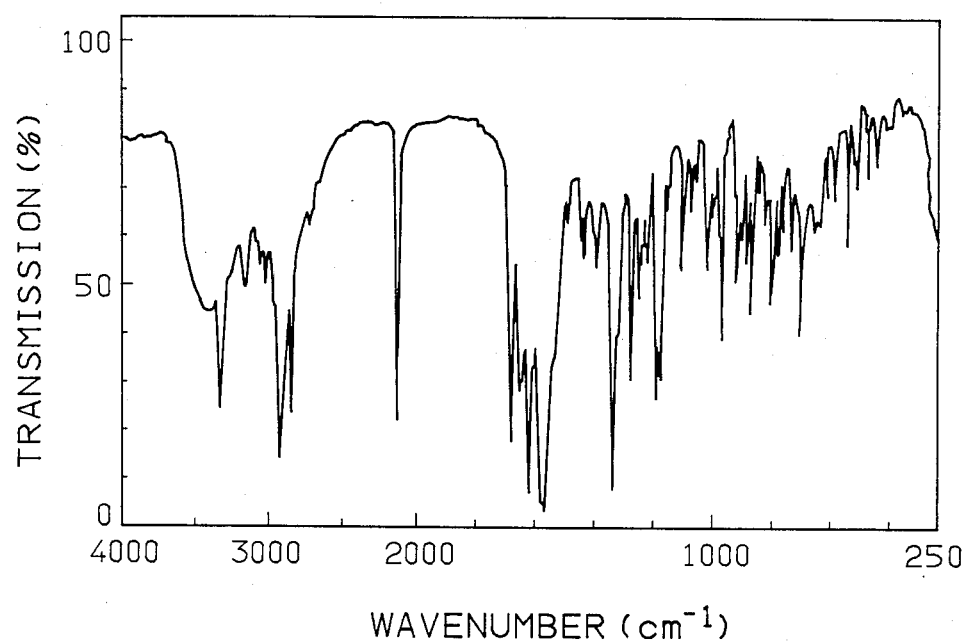
Figure 58:
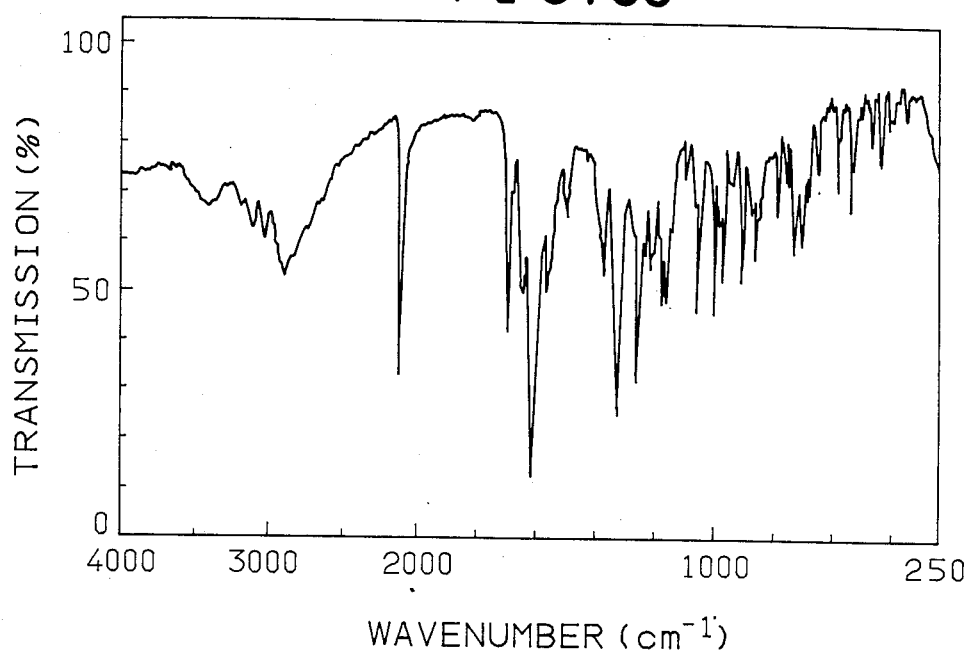
Figure 59:
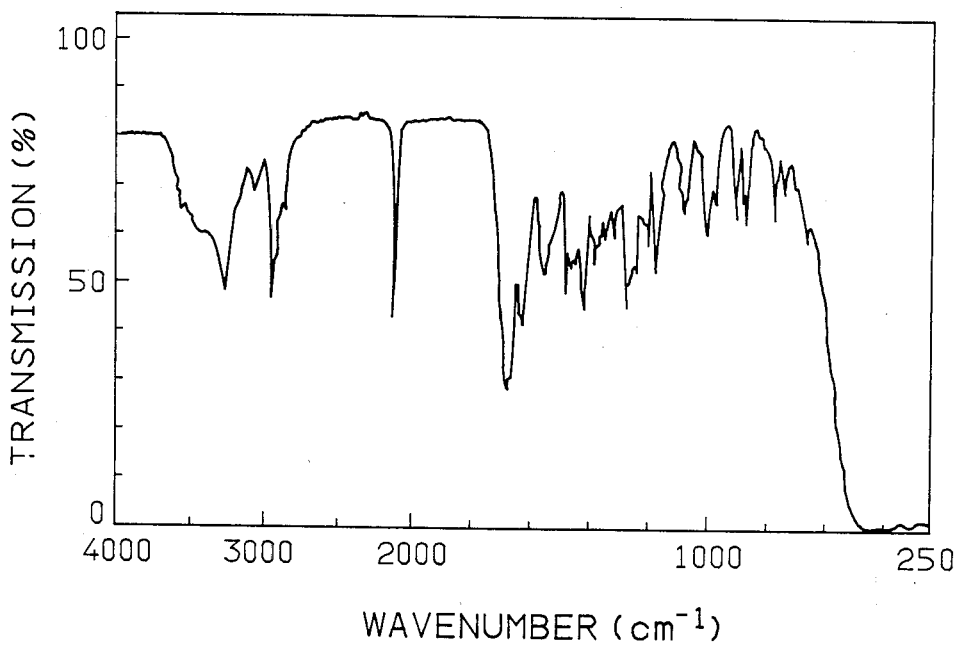
Figure 60:
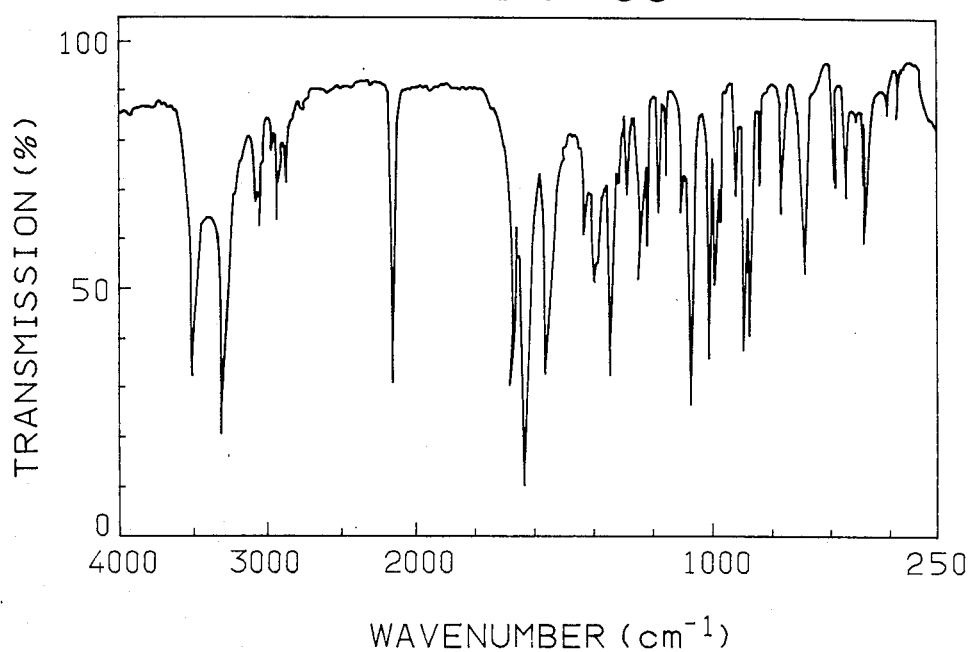
Figure 136:
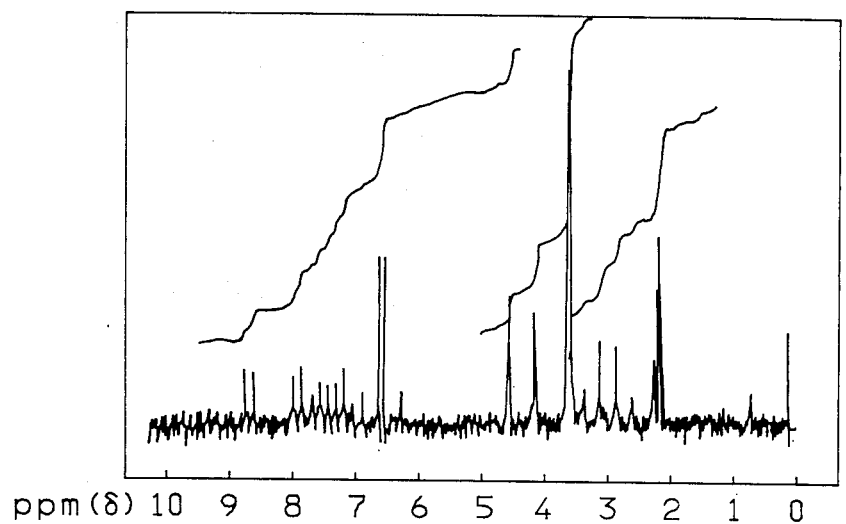
Figure 137:
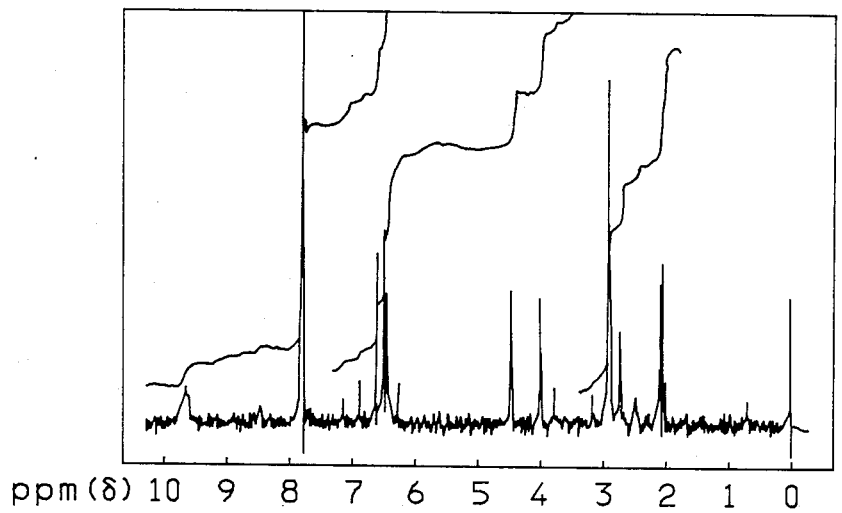
Figure 138:
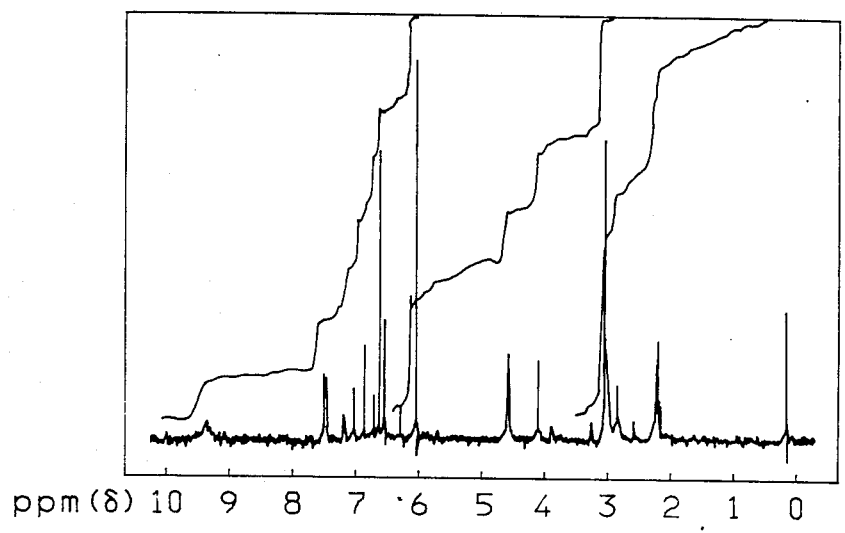
Figure 139:
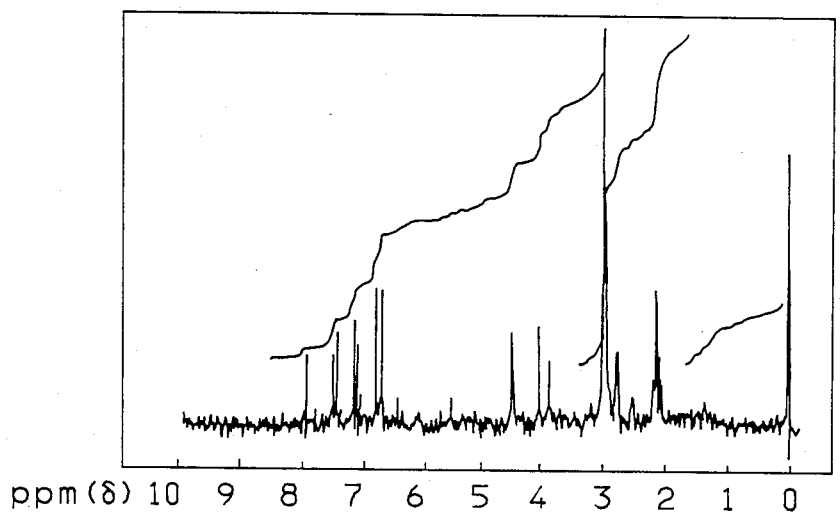
Figure 140:
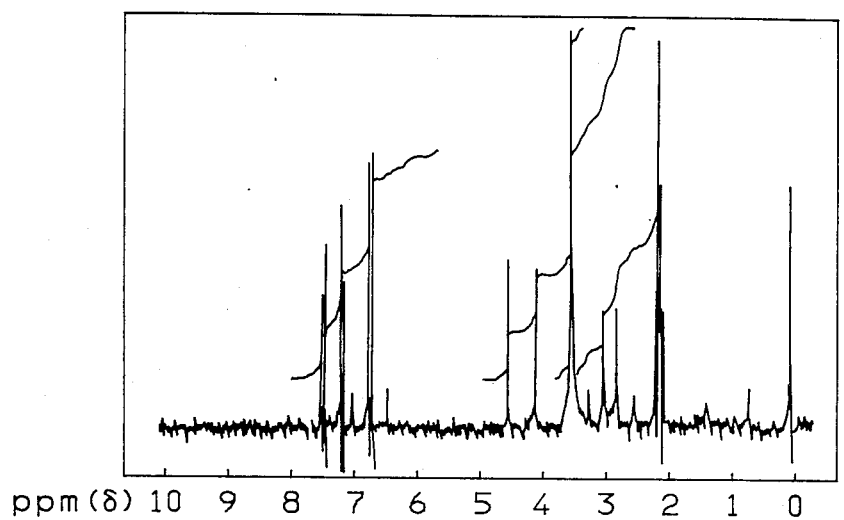
Figure 141:
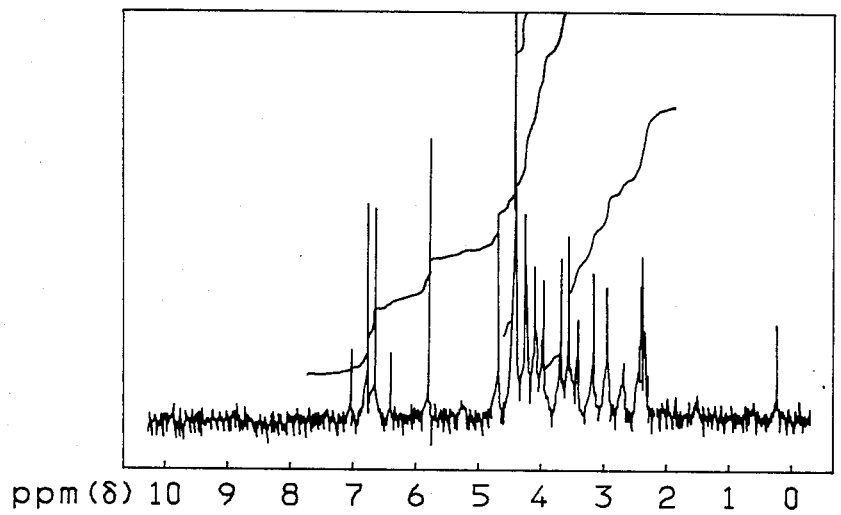
Figure 142:
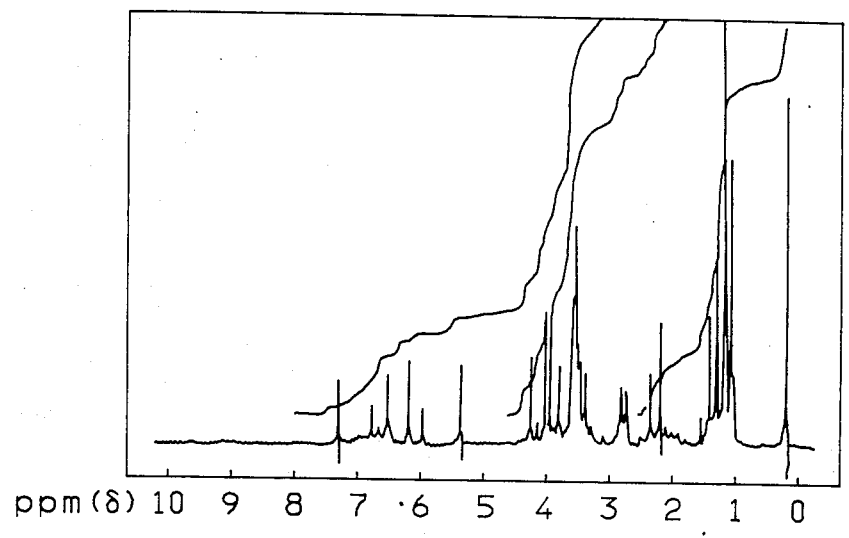
Figure 143:
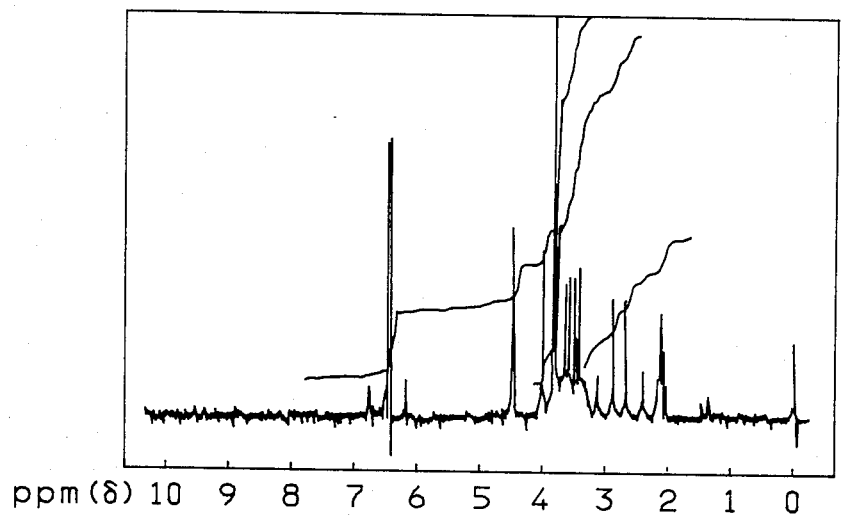

| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 62 | ![2-(aminocarbonyl)phenylamino: -NH-C6H4-CONH2] | micro-acicular crystal | >140 (decomp. and coloration) | FIG. 54 | FIG. 136 ((CD$_3$)$_2$CO + D$_2$O) |
| 63 | ![4-sulfamoylphenylamino: -NH-C6H4-SO2NH2] | micro-acicular crystal | >135 (decomp. and coloration) | FIG. 55 | FIG. 137 ((CD$_3$)$_2$CO) |
| 64 | ![benzo[1,3]dioxol-5-ylamino] | micro-acicular crystal | >150 (dec.) | FIG. 56 | FIG. 138 ((CD$_3$)$_2$CO) |
| 65 | ![thiazol-2-ylamino] | micro-acicular crystal | >140 (dec.) | FIG. 57 | FIG. 139 ((CD$_3$)$_2$CO) and FIG. 140 ((CD$_3$)$_2$CO + D$_2$O) |
| 66 | ![4,5-dihydrothiazol-2-ylamino] | micro-acicular crystal | >115 (dec.) | FIG. 58 | FIG. 141 ((CD$_3$)$_2$CO + D$_2$O) |
| 67 | —N(C$_2$H$_5$)—(CH$_2$)$_2$—NHCO—i-C$_4$H$_9$ | oil | | FIG. 59 | FIG. 142 (CDCl$_3$) |
| 68 | —NH—(CH$_2$)$_2$OH | acicular crystal | >160 (dec.) | FIG. 60 | FIG. 143 ((CD$_3$)$_2$CO + D$_2$O) |

TABLE 1-continued

Figure 61:
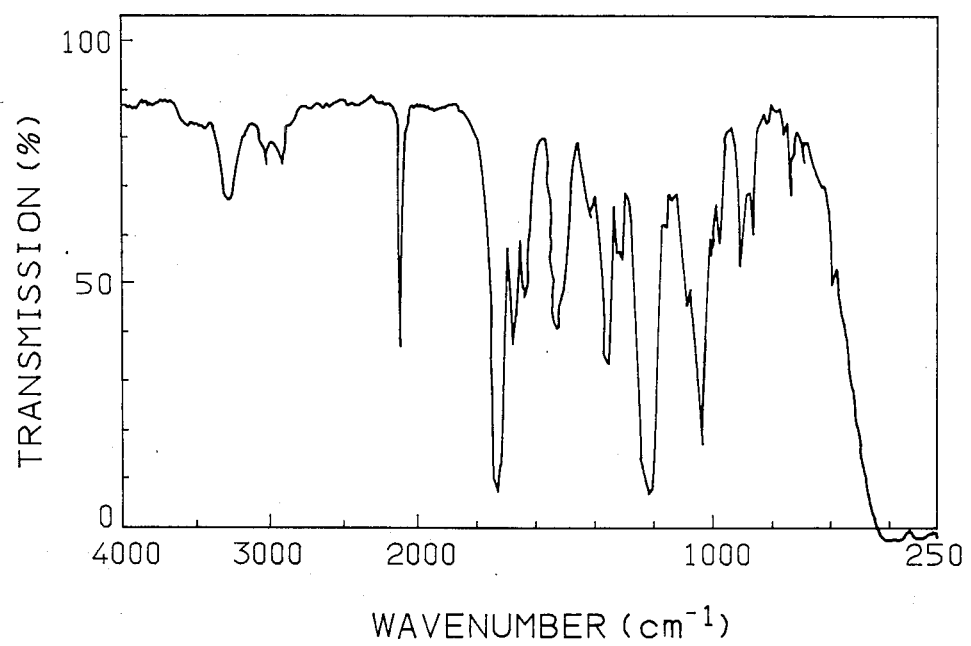
Figure 62:
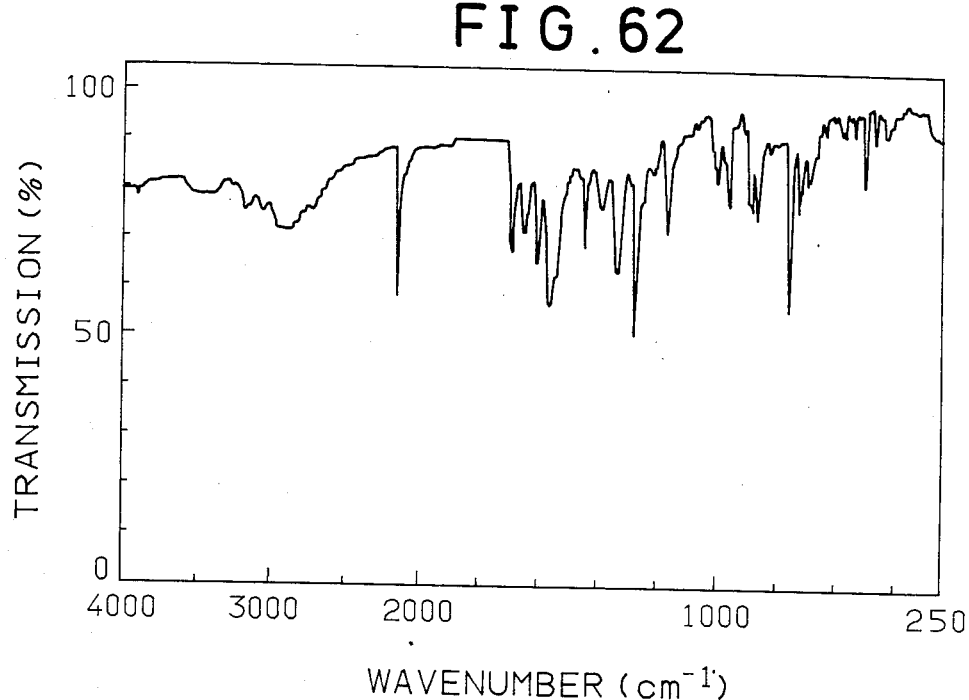
Figure 63:
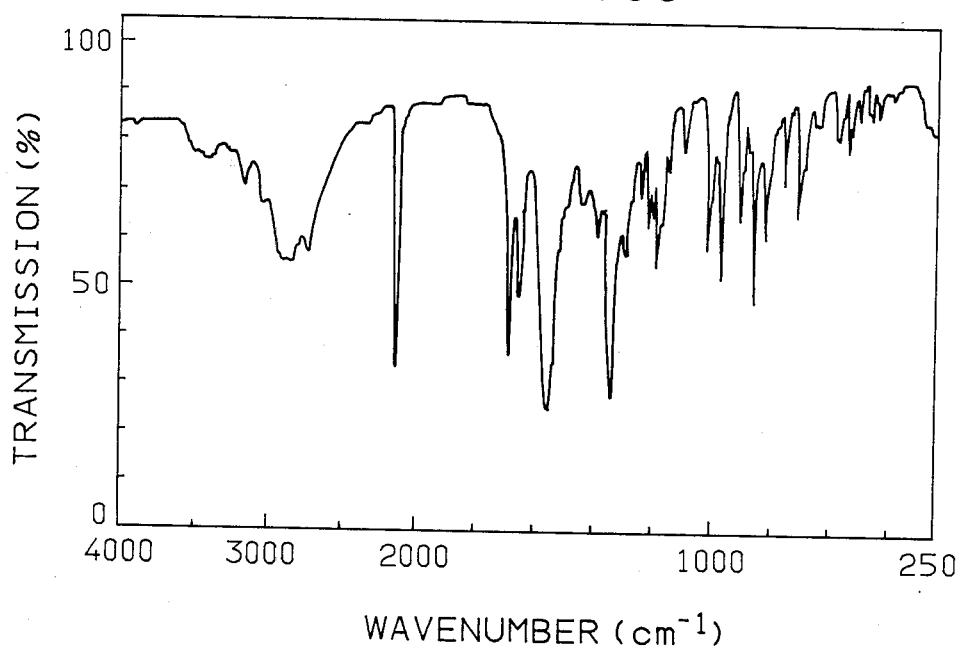
Figure 64:
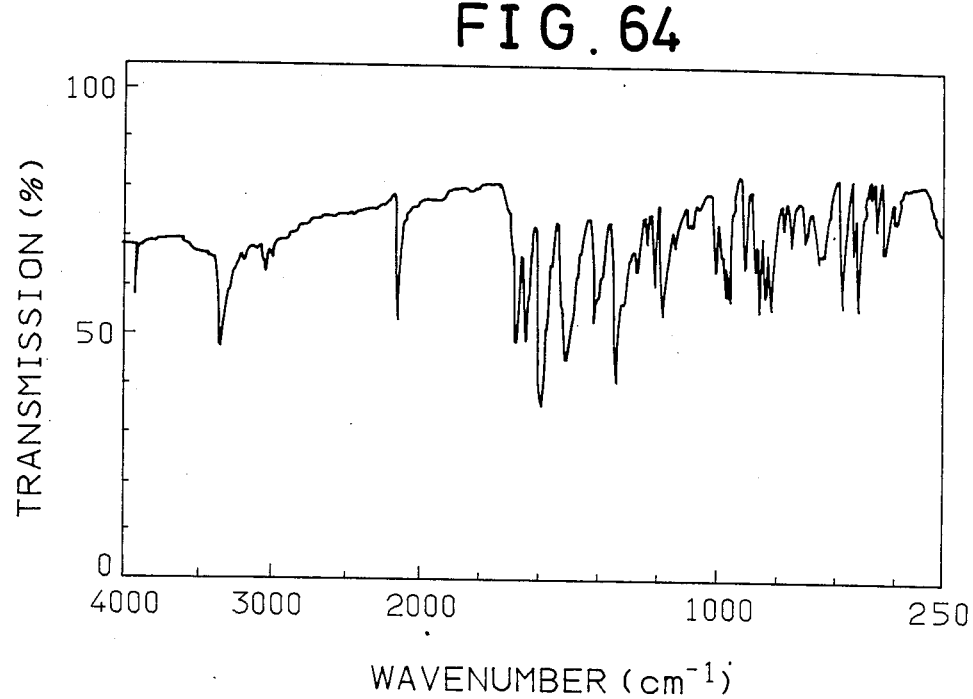
Figure 65:
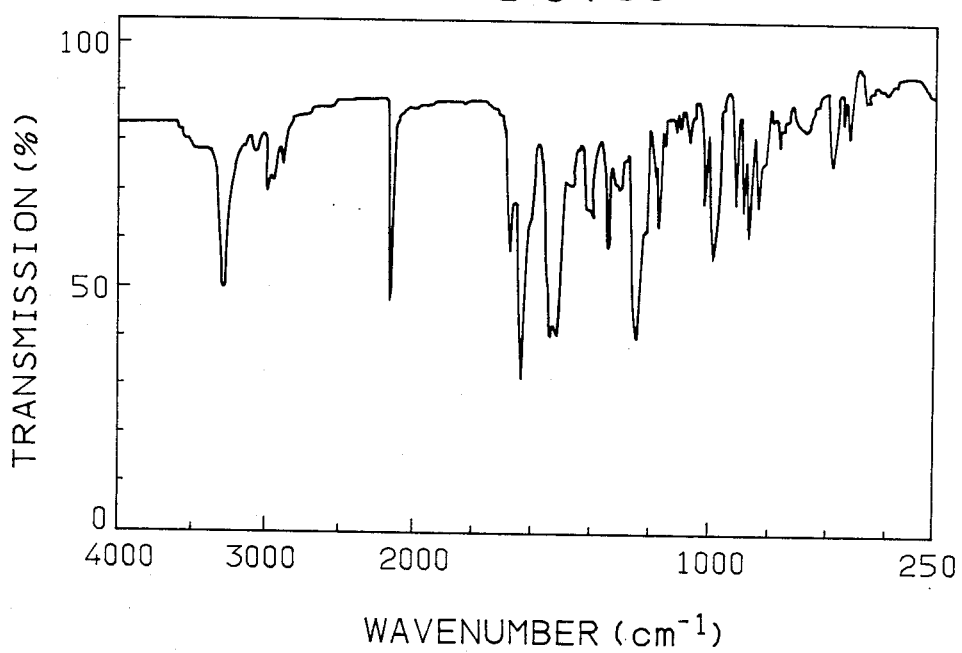
Figure 66:
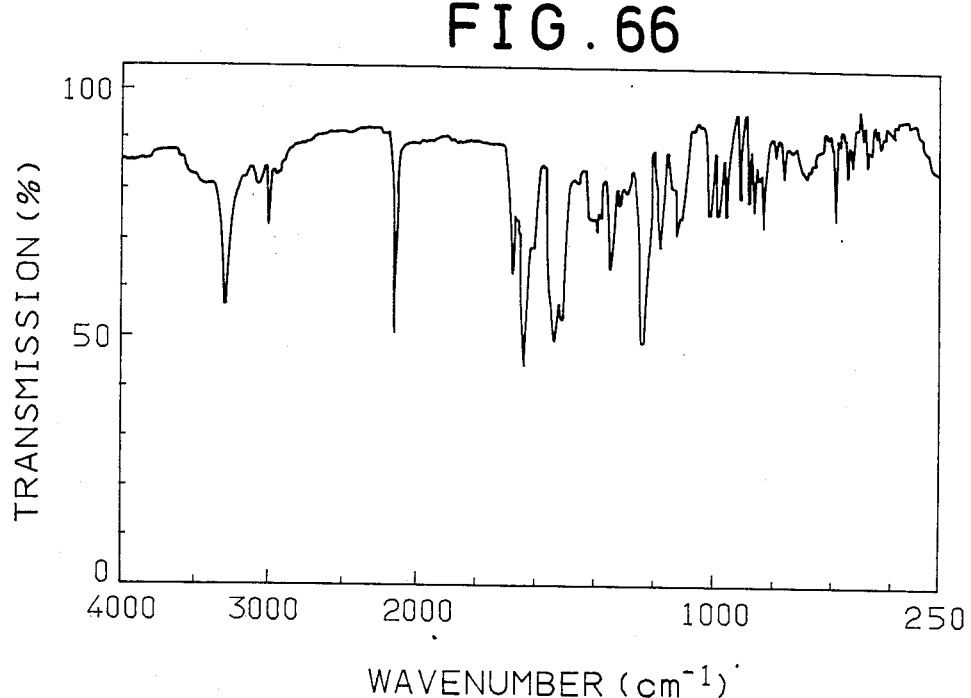
Figure 144:
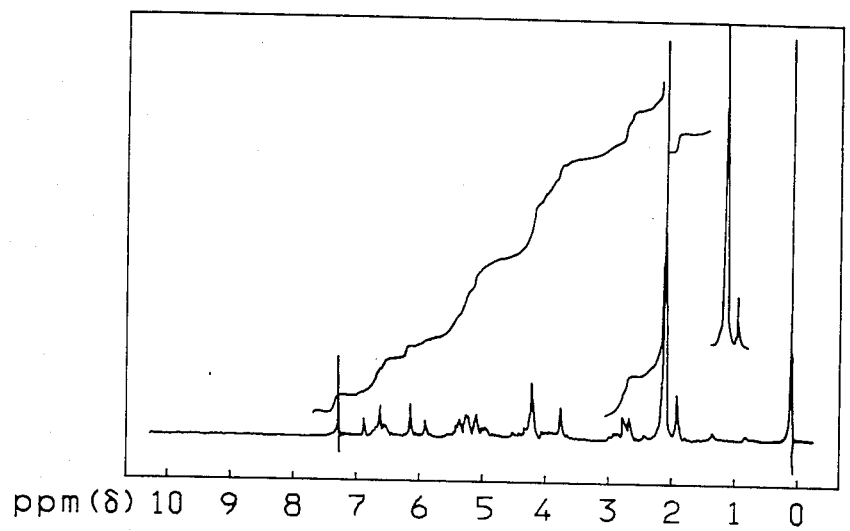
Figure 145:
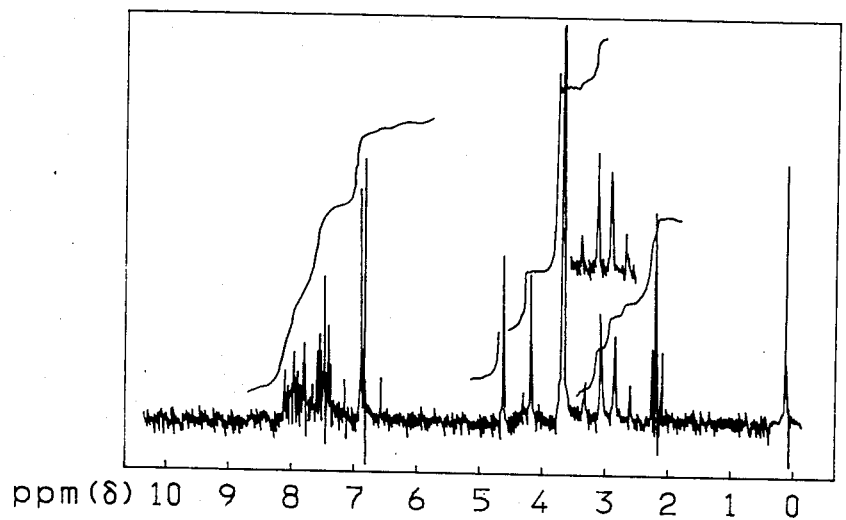
Figure 146:
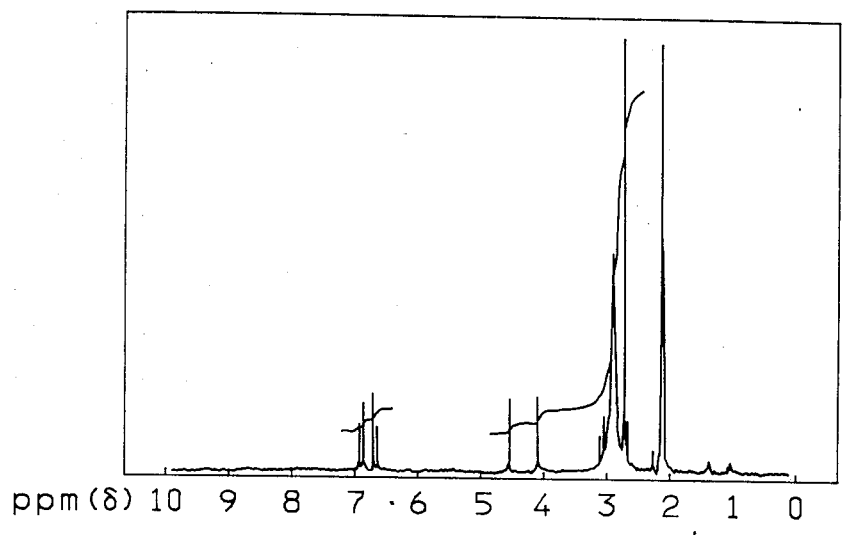
Figure 147:
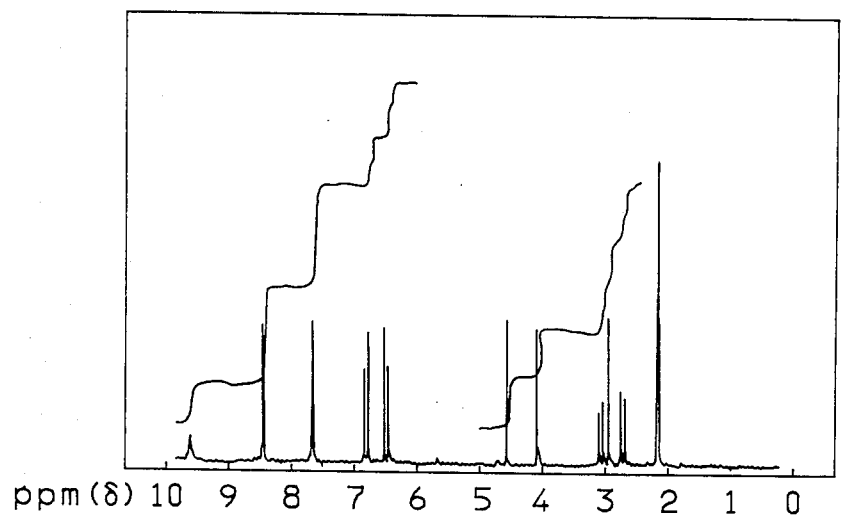
Figure 148:
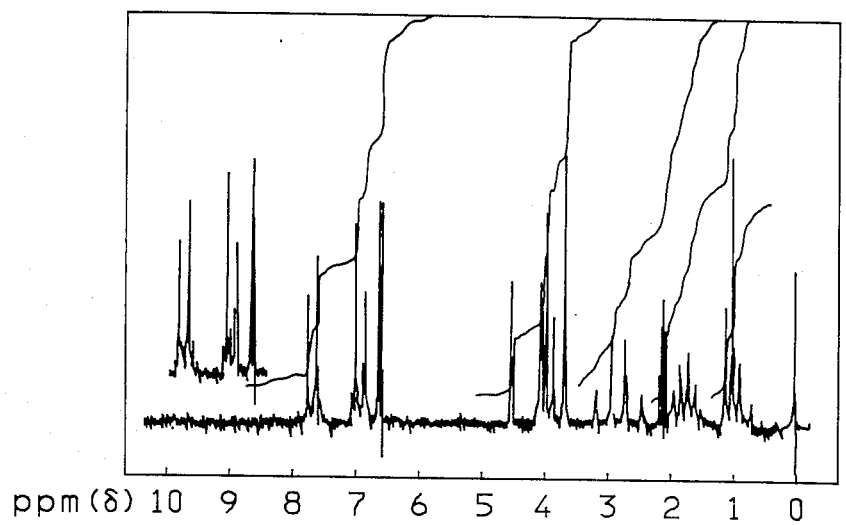
Figure 149:
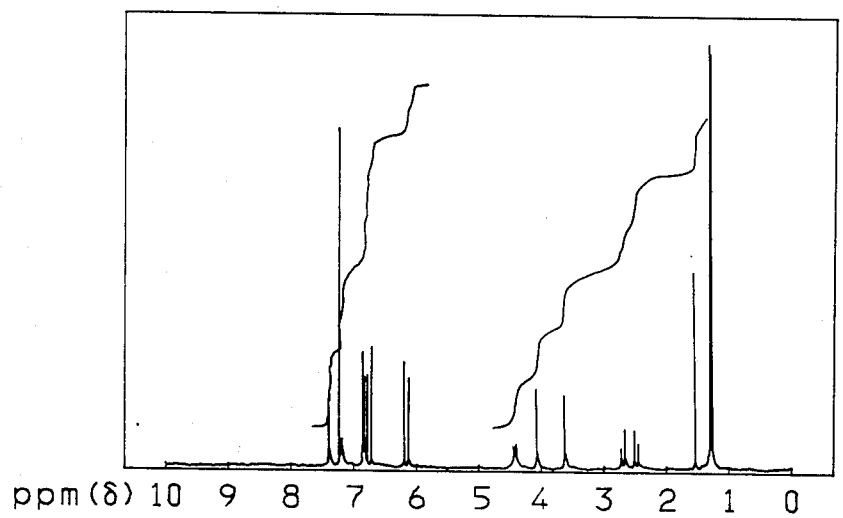

| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 69 | —NH—[sugar-OAc structure] | oil | | FIG. 61 | FIG. 144 (CDCl$_3$) |
| 70 | —NH—[benzothiazole] | acicular crystal | >130 (dec.) | FIG. 62 | FIG. 145 |
| 71 | —NH—C(CH$_3$)=N—N—S | acicular crystal | >130 (dec.) | FIG. 63 | FIG. 146 |
| 72 | —NH—[pyridyl] | acicular crystal | >100 (dec.) | FIG. 64 | FIG. 147 |
| 73 | —NH—C$_6$H$_4$—O(CH$_2$)$_2$—CH$_3$ | acicular crystal | >135 (dec.) | FIG. 65 | FIG. 148 |
| 74 | —NH—C$_6$H$_4$—OCH(CH$_3$)$_2$ | acicular crystal | >135 (dec.) | FIG. 66 | FIG. 149 |

TABLE 1-continued

[Structure: cyclopentane/dioxolane with CN and CH=CH-C(=O)-A substituents]

Figure 67:
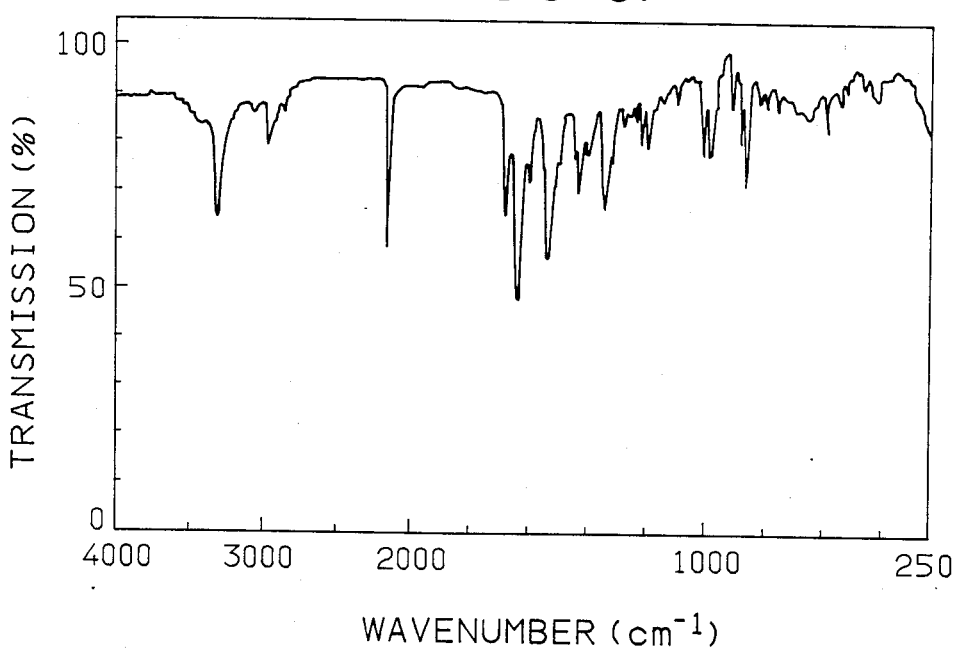
Figure 68:
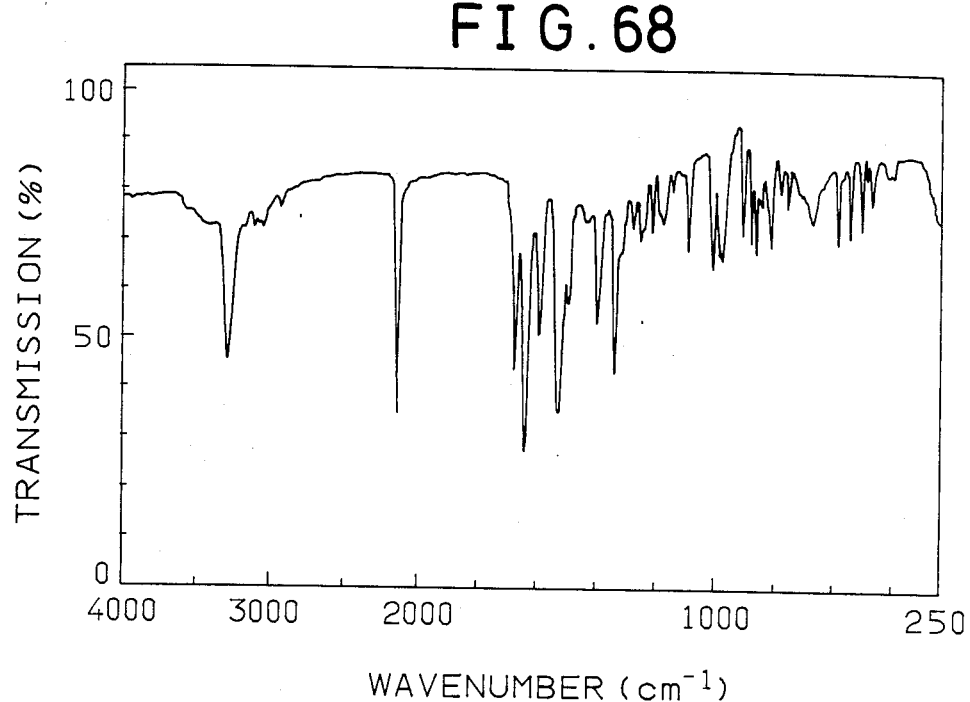
Figure 69:
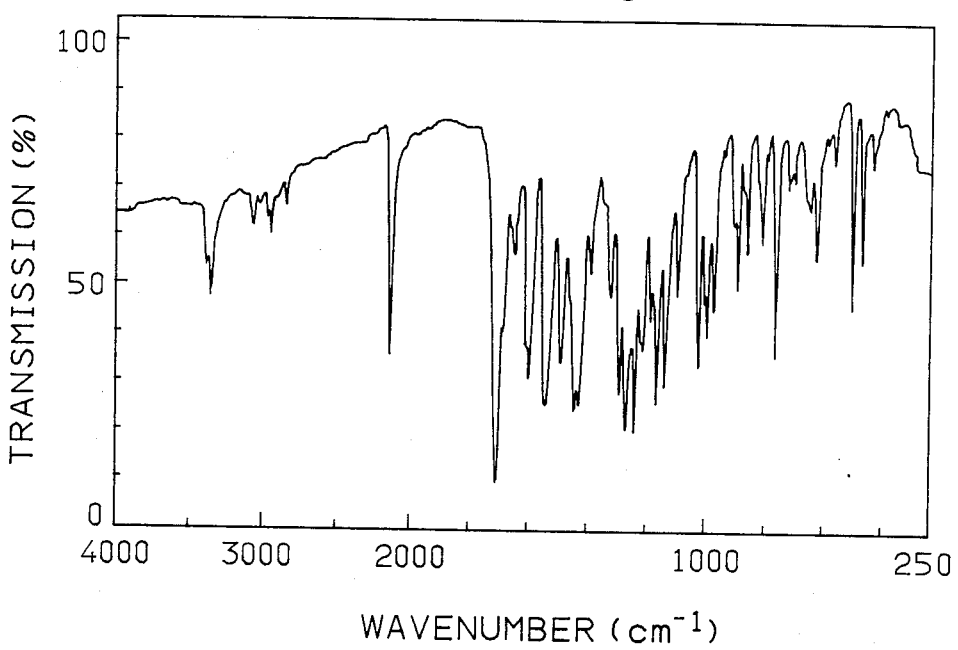
Figure 70:
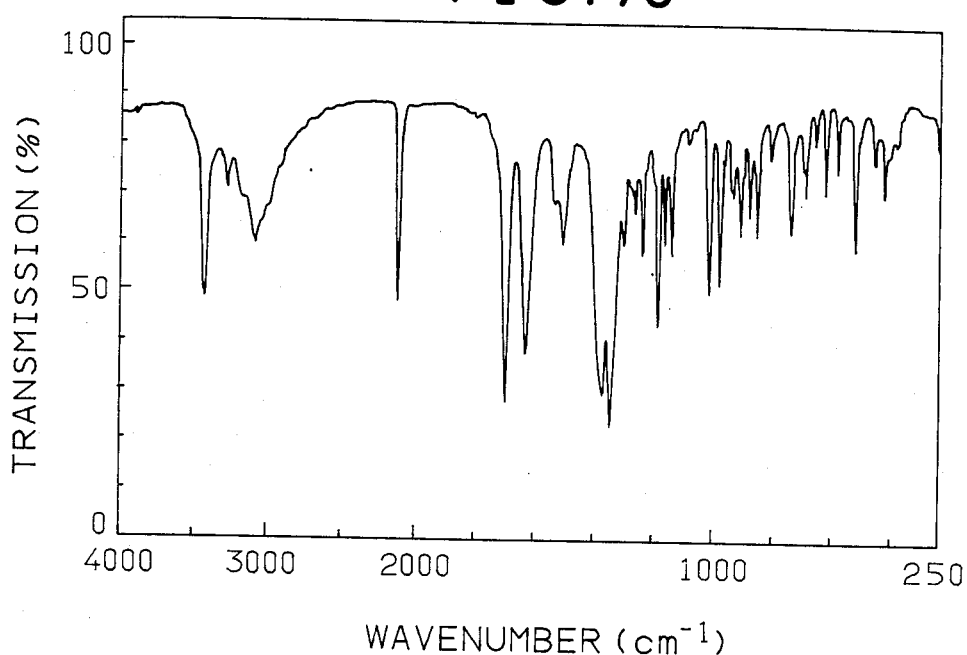
Figure 71:
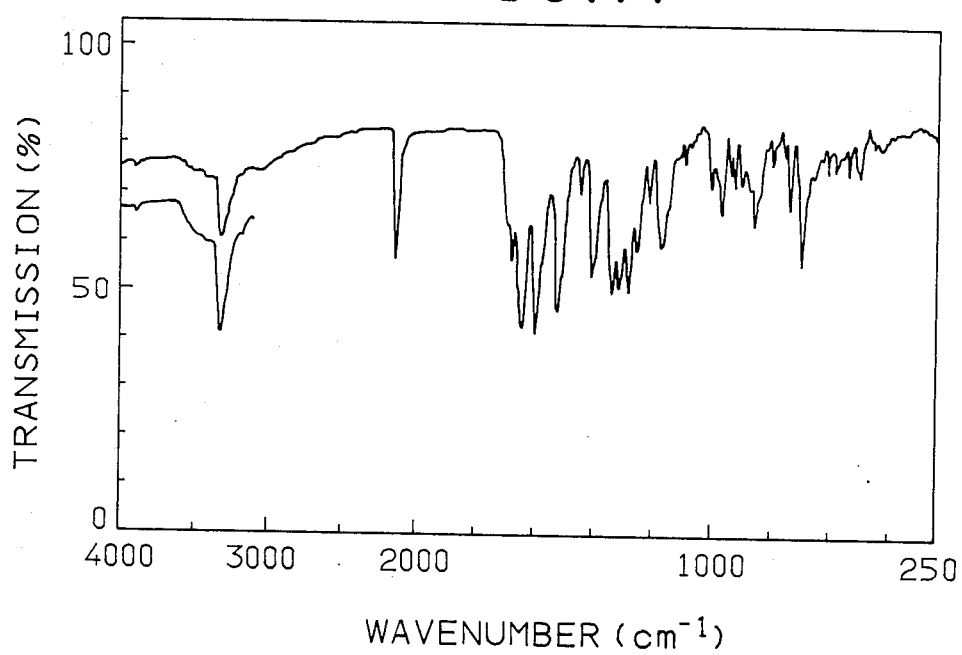
Figure 72:
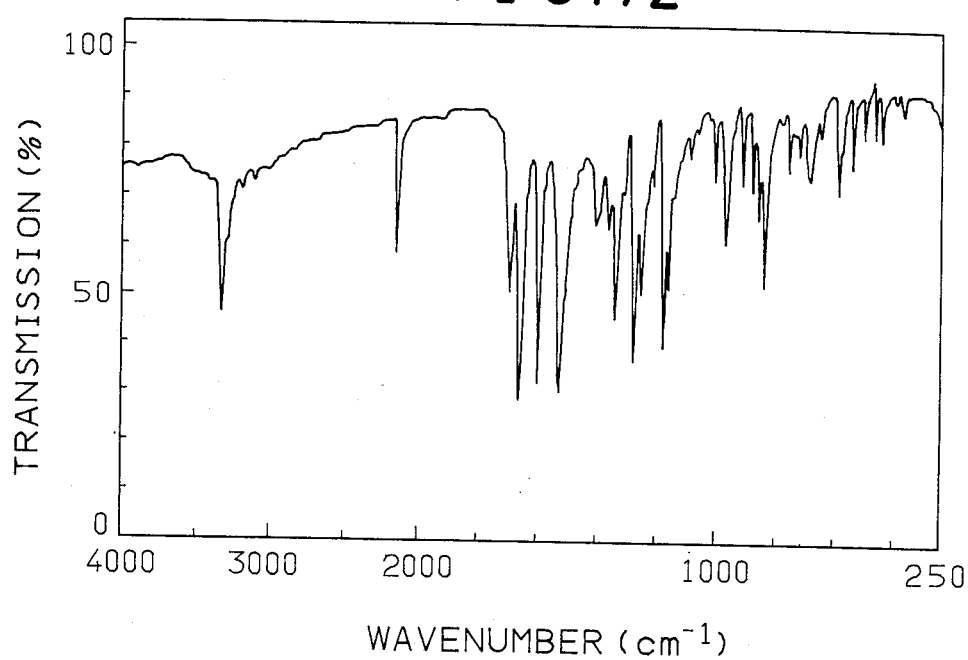
Figure 73:
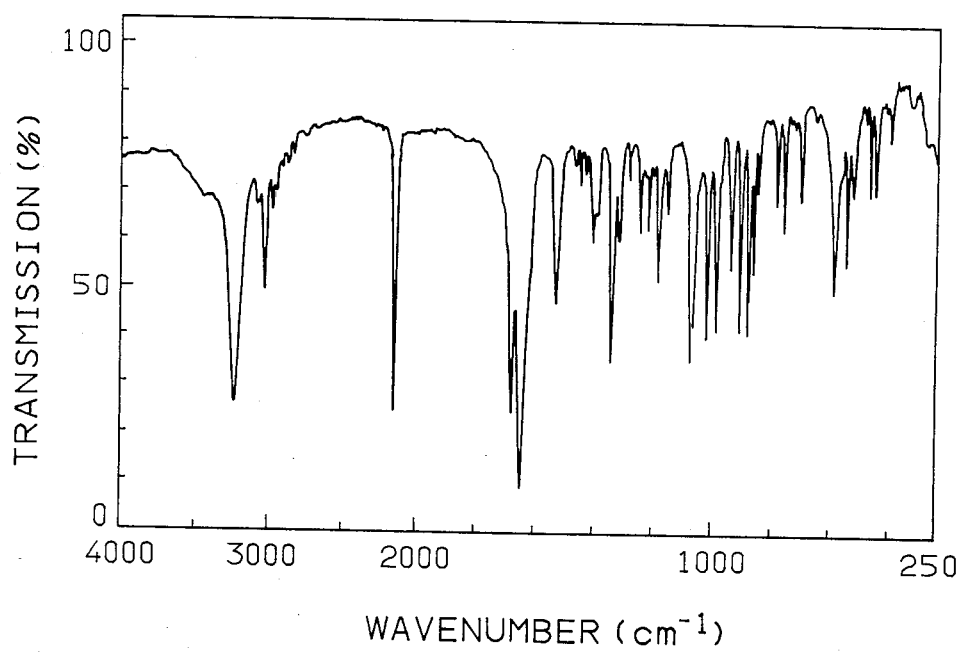
Figure 150:
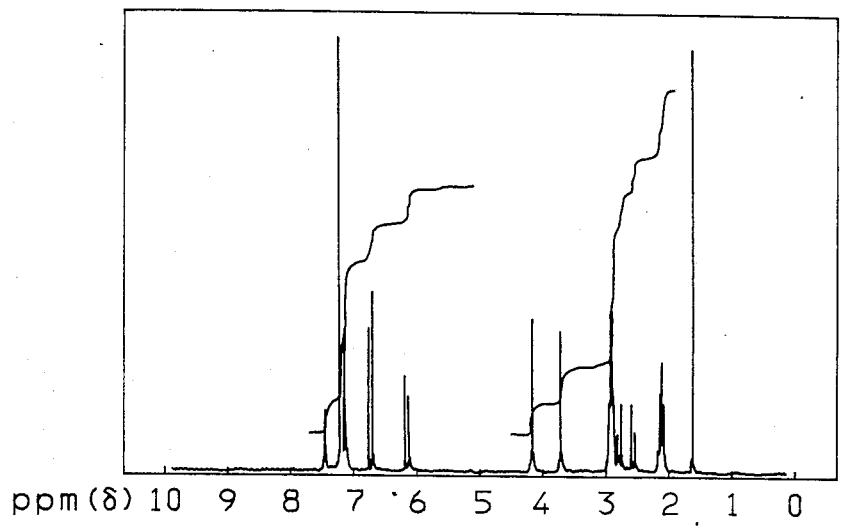
Figure 151:
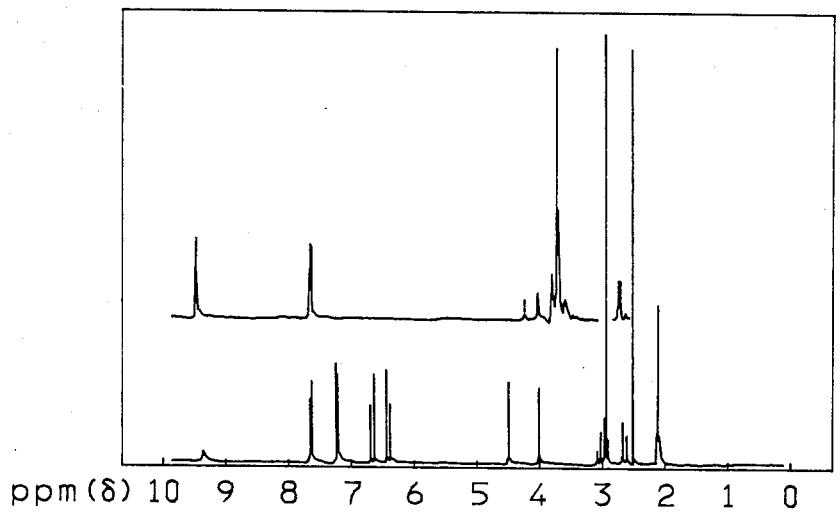
Figure 152:
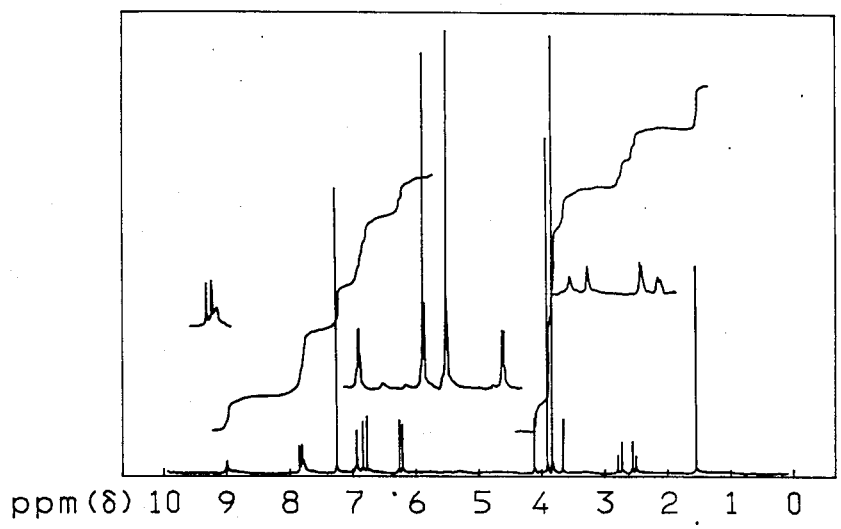
Figure 153:
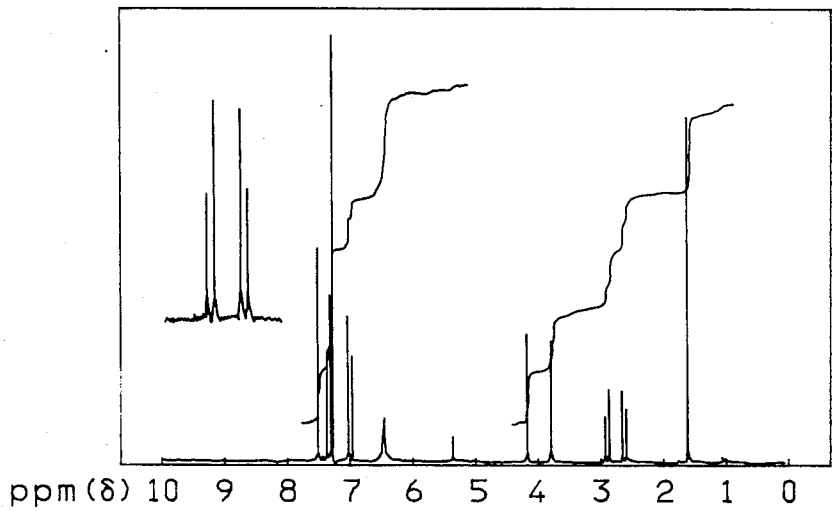
Figure 154:
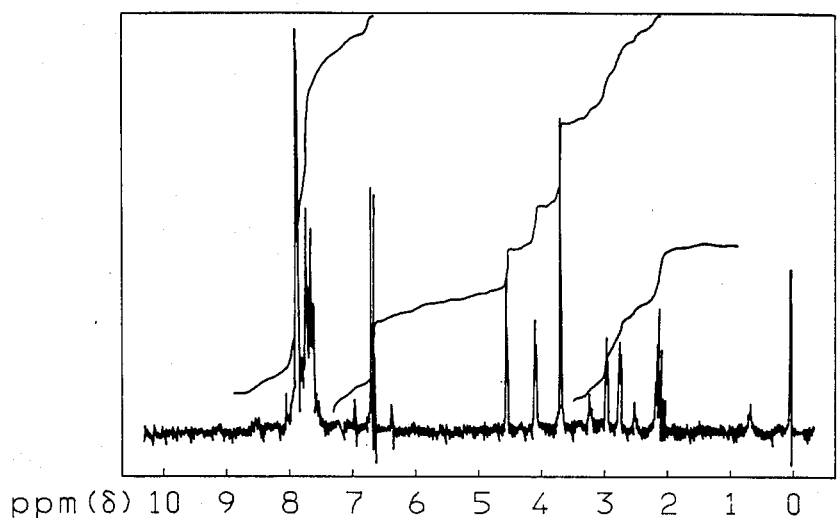
Figure 155:
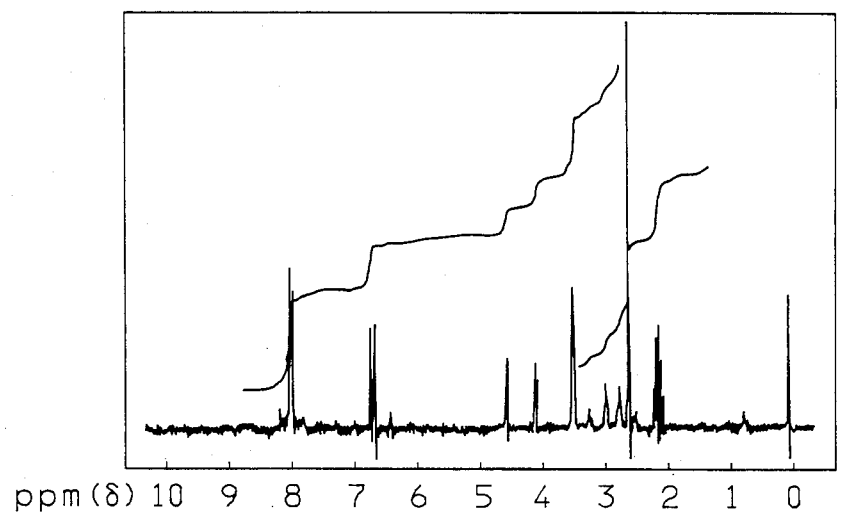
Figure 156:
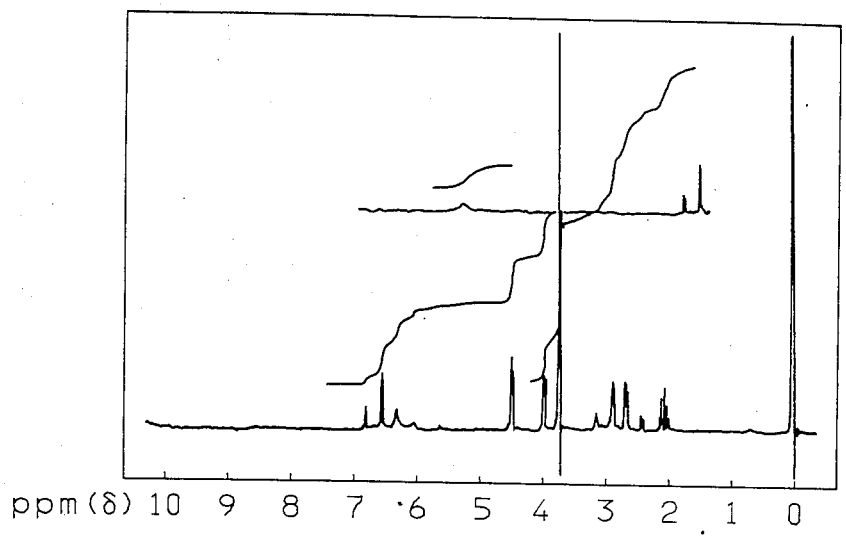

| No. of the compound of the present invention | A | Appearance | Melting point (°C.) | Infrared spectrum (KBr-method or Neat-method) | ¹H—nuclear magnetic resonance spectrum (Solvent) |
|---|---|---|---|---|---|
| 75 | —NH—(indanyl) | acicular crystal | >125 (dec.) | FIG. 67 | FIG. 150 |
| 76 | —NH—C₆H₄—SCH₃ | acicular crystal | >130 (dec.) | FIG. 68 | FIG. 151 |
| 77 | —NH—C₆H₃(COOCH₃)(OCH₃) | acicular crystal | >140 (dec.) | FIG. 69 | FIG. 152 |
| 78 | —NH—C(=N)—NH (imidazole) | acicular crystal | >120 (dec.) | FIG. 70 | FIG. 153 |
| 79 | —NH—C₆H₄—C(=O)—C₆H₅ | acicular crystal | >125 (dec.) | FIG. 71 | FIG. 154 |
| 80 | —NH—C₆H₄—COCH₃ | acicular crystal | >130 (dec.) | FIG. 72 | FIG. 155 |
| 81 | —NH—OCH₃ | acicular crystal | >115 (dec.) | FIG. 73 | FIG. 156 |

Figure 74:
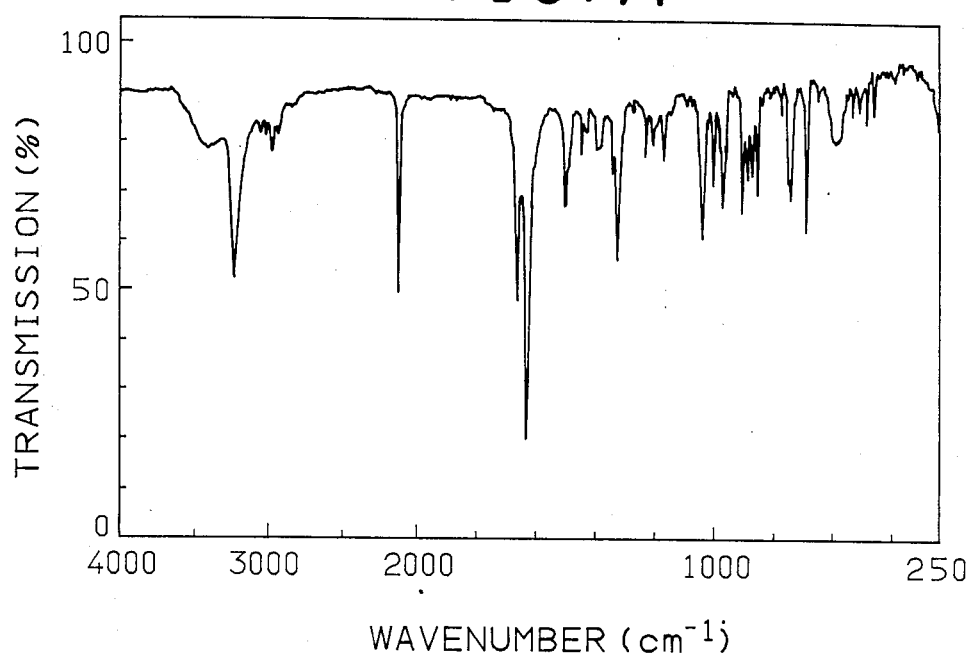
Figure 157:
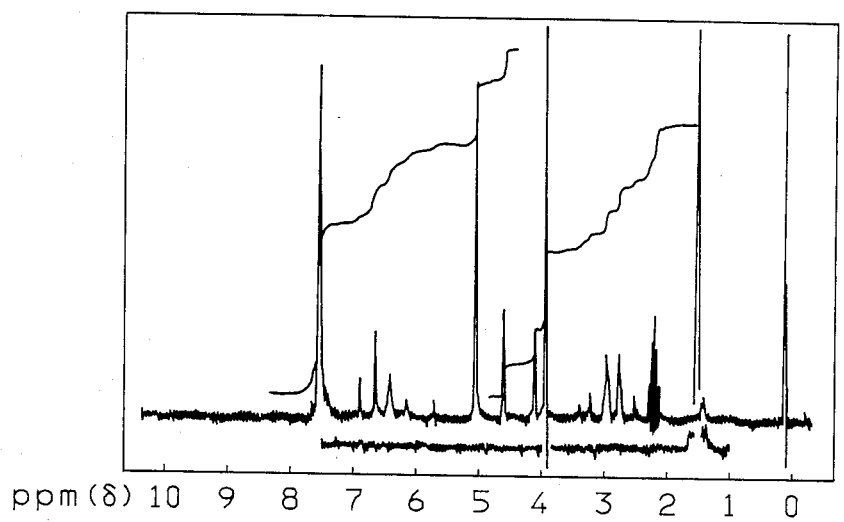

TABLE 1-continued
| No. of the compound of the present invention | A | Appearance | Melting point (°C.) | Infrared spectrum (KBr-method or Neat-method) | $^1$H—nuclear magnetic resonance spectrum (Solvent) |
|---|---|---|---|---|---|
| 82 | —NHOCH$_2$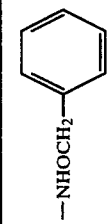 | acicular crystal | >145 (dec.) | FIG. 74 | FIG. 157 |
Notes:
*Steric configuration (L)
**Steric configuration (D)

TABLE 2

Minimum Inhibitory Concentration

| No. of Organism | No. of Compound | | | | | | | | | | | | | | | | | | | | | |
|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| 1 | 12.5 | 12.5 | 0.2 | 0.4 | 0.05 | 0.39 | 0.39 | 12.5 | 50 | 0.39 | 3.13 | 1.56 | 0.39 | 200 | 25 | 6.25 | >200 | 0.39 | 6.25 | 1.56 | 50 | 50 |
| 2 | 12.5 | 12.5 | 3.13 | 0.78 | 0.78 | 25 | 6.25 | 25 | 50 | 1.56 | 6.25 | 3.13 | 0.39 | 200 | 50 | 6.25 | >200 | 12.5 | 25 | 12.5 | 100 | 100 |
| 3 | 6.25 | 12.5 | 0.05 | 1.56 | 0.78 | 0.78 | 0.39 | 12.5 | 50 | 0.39 | 3.13 | 0.78 | 0.39 | 200 | 25 | 6.25 | >200 | 3.13 | 6.25 | 1.56 | 50 | 50 |
| 4 | 200 | >200 | 6.25 | 12.5 | 12.5 | >100 | 12.5 | 50 | 100 | 3.13 | 3.13 | 3.13 | 100 | >200 | 50 | 200 | >200 | 0.78 | 100 | 6.25 | 100 | 50 |
| 5 | 12.5 | 50 | 50 | 6.25 | 6.25 | >100 | 25 | 25 | 50 | 6.25 | 25 | 6.25 | 100 | >200 | 50 | 200 | >200 | 12.5 | 6.25 | >200 | >200 | 50 |
| 6 | 12.5 | 25 | 50 | 6.25 | <0.05 | 50 | 3.13 | 25 | 200 | 3.13 | 6.25 | 0.39 | 100 | >200 | 50 | >200 | >200 | 12.5 | 6.25 | >200 | >200 | 50 |
| 7 | 6.25 | 6.25 | 6.25 | 6.25 | 6.25 | >100 | 25 | 50 | 50 | <0.1 | 12.5 | 3.13 | 100 | >200 | 50 | 50 | >200 | 1.56 | 12.5 | 0.39 | 50 | 50 |
| 8 | 12.5 | 25 | 50 | 6.25 | 6.25 | 50 | 3.13 | 12.5 | 200 | 3.13 | 6.25 | 3.13 | 25 | >200 | 25 | 50 | 200 | 12.5 | 12.5 | 100 | 100 | 25 |
| 9 | 3.13 | 6.25 | 12.5 | 3.13 | 3.13 | 50 | 25 | 25 | 50 | <0.1 | 12.5 | 3.13 | 50 | >200 | 50 | >200 | >200 | 3.13 | 1.56 | 6.25 | 50 | 6.25 |
| 10 | 6.25 | 6.25 | 6.25 | <0.05 | <0.05 | >100 | 6.25 | 25 | 50 | 0.78 | 6.25 | 3.13 | 25 | >200 | 25 | 50 | >200 | 1.56 | 6.25 | 6.25 | 100 | 25 |
| 11 | 6.25 | 6.25 | 6.25 | <0.05 | <0.05 | 50 | 6.25 | 12.5 | 50 | <0.1 | 12.5 | 3.13 | 12.5 | >200 | 25 | >200 | >200 | 0.78 | 12.5 | 3.13 | 50 | 25 |
| 12 | 6.25 | 6.25 | 12.5 | 3.13 | 3.13 | >100 | 6.25 | 12.5 | 50 | 3.13 | 12.5 | 3.13 | 200 | >200 | 50 | 100 | >200 | 6.25 | 3.13 | 12.5 | 50 | 25 |
| 13 | 200 | >200 | >100 | >100 | >100 | >100 | 25 | 100 | 200 | 12.5 | 12.5 | 12.5 | 100 | >200 | >100 | 25 | >100 | 200 | 50 | 50 | >200 | 12.5 |
| 14 | 50 | 50 | 50 | 12.5 | 12.5 | 100 | 6.25 | 25 | 200 | 0.78 | 0.78 | 1.56 | 25 | >200 | 50 | >200 | >100 | 0.78 | 50 | >200 | 200 | >200 |
| 15 | >200 | >200 | >100 | >100 | >100 | >100 | >100 | >100 | >200 | >100 | >100 | >100 | >200 | >200 | >100 | >200 | >200 | >200 | 100 | >200 | >200 | >200 |
| 16 | >200 | >200 | >100 | >100 | >100 | >100 | >100 | >100 | >200 | >100 | >100 | >100 | >200 | >200 | >100 | >200 | >200 | 200 | >200 | >200 | >200 | >200 |
| 17 | >200 | >200 | >100 | >100 | >100 | >100 | >100 | >100 | >200 | >100 | >100 | >100 | >200 | >200 | >100 | >200 | >200 | >200 | 200 | >200 | >200 | >200 |
| 18 | 6.25 | 6.25 | 3.13 | 100 | 100 | 12.5 | 12.5 | 25 | 50 | 0.39 | 3.13 | 1.56 | 12.5 | >200 | 25 | 12.5 | >200 | 3.13 | 3.13 | 0.78 | 50 | 6.25 |
| 19 | 6.25 | 25 | 50 | >200 | 100 | >100 | 12.5 | 100 | 200 | <0.1 | 12.5 | 3.13 | >200 | >200 | 100 | >200 | >200 | 6.25 | 50 | >200 | >200 | >200 |
| 20 | 6.25 | 6.25 | 1.56 | 0.39 | 0.39 | 1.56 | 1.56 | 12.5 | 25 | <0.1 | 6.25 | 0.78 | 25 | 12.5 | 6.25 | 3.13 | >200 | 0.2 | 3.13 | 0.78 | 25 | 12.5 |
| 21 | 0.2 | 0.2 | 0.05 | 0.39 | 0.39 | 0.2 | 0.39 | 12.5 | 25 | <0.1 | 3.13 | <0.1 | 0.1 | 12.5 | <0.1 | 3.13 | >200 | 0.1 | 1.56 | 0.1 | 1.56 | 1.56 |
| 22 | 25 | >200 | 50 | 100 | 100 | >100 | >100 | >100 | >200 | >100 | >100 | >100 | 100 | >200 | >100 | 100 | >200 | 100 | 6.25 | >200 | >200 | >200 |
| 23 | >200 | >200 | >100 | >100 | 100 | >100 | >100 | >100 | >200 | <0.1 | >100 | >100 | >200 | >200 | >100 | >200 | >200 | 200 | 100 | >200 | >200 | >200 |
| 24 | 25 | >200 | 6.25 | >100 | 50 | >100 | >100 | >100 | >200 | 6.25 | >100 | >100 | >200 | >200 | >100 | >200 | >200 | 200 | 6.25 | >200 | >200 | >200 |
| 25 | 6.25 | 1.56 | 6.25 | <0.05 | <0.05 | 0.39 | 0.39 | 12.5 | 25 | 50 | <0.1 | <0.1 | <0.1 | 0.78 | <0.1 | <0.1 | >200 | <0.2 | 25 | <0.05 | 0.39 | 0.39 |
| 26 | 100 | 100 | 6.25 | 6.25 | 1.56 | >100 | >100 | 50 | 100 | 3.13 | 3.13 | 3.13 | 100 | >200 | 50 | 200 | >200 | 1.56 | 100 | 6.25 | >200 | 200 |
| 27 | 12.5 | <0.2 | 3.13 | 12.5 | 12.5 | 25 | 12.5 | 25 | 50 | 1.56 | <0.2 | 0.4 | 0.2 | 0.78 | 50 | 200 | 100 | 12.5 | 100 | 12.5 | >200 | >200 |
| 28 | <0.2 | <0.2 | 0.05 | <0.05 | <0.05 | <0.2 | <0.2 | 1.56 | 6.25 | 0.8 | <0.2 | 1.56 | 0.8 | 0.78 | 12 | 3.13 | >100 | <0.2 | <0.2 | <0.05 | >200 | 1.56 |
| 29 | 6.25 | 3.13 | 0.8 | 1.56 | 1.56 | 0.8 | 1.56 | 25 | >100 | 1.56 | 1.56 | 1.56 | 0.8 | 3.13 | 6.25 | 3.13 | >100 | 0.2 | 12.5 | 1.56 | 6.25 | 6.25 |
| 30 | 12.5 | 12.5 | 3.13 | 6.25 | 6.25 | 3.13 | 3.13 | 100 | >100 | 1.56 | 6.25 | 3.13 | 6.25 | 25 | 6.25 | 6.25 | >100 | 0.78 | 6.25 | 6.25 | 3.13 | 3.13 |

| No. of Organism | No. of Compound | | | | | | | | | | | | | | | | | | | | | |
|---|---|---|---|---|---|---|---|---|---|---|---|---|---|---|---|---|---|---|---|---|---|---|
| | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
| 1 | 200 | 0.78 | 0.1 | 25 | 25 | 12.5 | <1.56 | >200 | >200 | 200 | 1.56 | >100 | 25 | 0.39 | 0.39 | <0.05 | 0.78 | <0.05 | 0.2 | 0.39 | 0.78 | 0.39 |
| 2 | >200 | 1.56 | 0.78 | 100 | 100 | 12.5 | 6.25 | >200 | >200 | 200 | 0.78 | >100 | 25 | 0.78 | 1.56 | 0.1 | 3.13 | 0.1 | 0.39 | 1.56 | 3.13 | 3.13 |
| 3 | 200 | 0.78 | 0.78 | 25 | 25 | 12.5 | 3.13 | >200 | >200 | 200 | 1.56 | >100 | 25 | 0.39 | 0.39 | <0.05 | 1.56 | <0.05 | 0.1 | 0.39 | 1.56 | 0.39 |
| 4 | 50 | 6.25 | 1.56 | 50 | 50 | >200 | >200 | >200 | >200 | >200 | 0.78 | >100 | 50 | 1.56 | 12.5 | 6.25 | 100 | 200 | >200 | >200 | 25 | >200 |
| 5 | 50 | 12.5 | 12.5 | 100 | 100 | >200 | >200 | >200 | >200 | >200 | 25 | >100 | 50 | 12.5 | 25 | 12.5 | >200 | >200 | >200 | >200 | >200 | >200 |
| 6 | 50 | 6.25 | 6.25 | 50 | 50 | >200 | >200 | >200 | >200 | >200 | 25 | >100 | 50 | 6.25 | 25 | <0.05 | 1.56 | <0.05 | 200 | >200 | 25 | >200 |
| 7 | 200 | 1.56 | 100 | 50 | 25 | >200 | >200 | >200 | >200 | >200 | 12.5 | >100 | >200 | 0.39 | 0.1 | 6.25 | >200 | >200 | >200 | >200 | 6.25 | >200 |
| 8 | 50 | 6.25 | 100 | 50 | 25 | >200 | >200 | >200 | >200 | >200 | 25 | >100 | 100 | 12.5 | 6.25 | 6.25 | >200 | >200 | >200 | 25 | 25 | 0.2 |
| 9 | 12.5 | 1.56 | 100 | 25 | 25 | >200 | >200 | >200 | >200 | >200 | 3.13 | >100 | >200 | 0.39 | 1.56 | 1.56 | >200 | 12.5 | 3.13 | 12.5 | 0.78 | 12.5 |
| 10 | 25 | 3.13 | 0.1 | 50 | 25 | >200 | >200 | >200 | >200 | >200 | 12.5 | >100 | 6.25 | 12.5 | 0.2 | <0.05 | 25 | 0.39 | 3.13 | 6.25 | 6.25 | 3.13 |
| 11 | 50 | 0.78 | 100 | 50 | 25 | >200 | >200 | >200 | >200 | >200 | 0.38 | >100 | 12.5 | 0.39 | 0.2 | <0.05 | 12.5 | 0.1 | 3.13 | 3.13 | 0.78 | 3.13 |
| 12 | 50 | 1.56 | 100 | 50 | 25 | >200 | >200 | >200 | >200 | >200 | 0.38 | >100 | 100 | 0.78 | 0.2 | <0.05 | 3.13 | 0.1 | 0.2 | 25 | 3.13 | 3.13 |
| 13 | 25 | 3.13 | 0.39 | 50 | 25 | >200 | >200 | >200 | >200 | >200 | 1.56 | >100 | 25 | 12.5 | 1.56 | 1.56 | 50 | 3.13 | 3.13 | 25 | 3.13 | 50 |
| 14 | 200 | 12.5 | 0.39 | 100 | 100 | >1.56 | 25 | >200 | >200 | >200 | 0.78 | >100 | | 12.5 | 6.25 | 3.13 | >200 | 6.25 | 1.56 | 6.25 | 6.25 | 25 |

TABLE 2-continued

Minimum Inhibitory Concentration

| No. of Organism | 45 | 46 | 47 | 48 | 49 | 50 | 51 | 52 | 53 | 54 | 55 | 56 | 57 | 58 | 59 | 60 | 61 | 62 | 63 | 64 | 65 | 66 |
|---|---|---|---|---|---|---|---|---|---|---|---|---|---|---|---|---|---|---|---|---|---|---|
| 15 | >200 | >100 | <0.05 | 0.2 | <0.05 | 0.2 | 12.5 | 12 | <0.05 | 0.39 | 1.56 | 1.56 | 1.56 | 3.13 | 6.25 | 3.13 | 3.13 | 12.5 | 3.13 | 0.2 | <0.1 | 12.5 |
| 16 | >200 | >100 | 0.2 | 0.39 | <0.05 | 1.56 | 12.5 | 50 | <0.05 | 1.56 | 3.13 | 6.25 | 6.25 | 3.13 | 25 | 12.5 | 12.5 | 50 | 25 | 0.78 | 0.39 | 25 |
| 17 | >200 | >100 | <0.05 | 0.1 | <0.05 | 0.39 | 6.25 | 25 | <0.05 | 0.2 | 0.78 | 1.56 | 1.56 | 3.13 | 6.25 | 3.13 | 3.13 | 12.5 | 3.13 | 0.2 | <0.1 | 12.5 |
| 18 | 12.5 | 1.56 | >200 | — | 12.5 | >200 | 12.5 | 25 | 6.25 | 25 | 200 | 25 | 12.5 | 12.5 | 50 | 25 | — | >200 | >200 | 12.5 | 12.5 | 12.5 |
| 19 | >200 | 12.5 | 200 | 25 | 50 | >200 | 200 | 200 | 12.5 | 50 | 200 | 25 | 12.5 | 12.5 | 25 | 25 | 12.5 | 3.13 | 3.13 | 25 | 6.25 | 25 |
| 20 | 25 | 0.78 | 200 | 25 | 50 | 0.39 | 100 | 200 | 3.13 | 0.2 | 0.39 | 25 | 1.56 | 0.78 | 3.13 | 1.56 | 1.56 | 3.13 | >200 | 12.5 | 6.25 | 50 |
| 21 | 25 | <0.05 | 0.1 | 0.2 | <0.05 | >200 | 50 | 100 | <0.05 | 6.25 | 25 | 1.56 | 3.13 | 3.13 | 12.5 | 12.5 | 6.25 | 50 | 3.13 | 0.2 | 1.56 | 6.25 |
| 22 | >200 | 0.39 | >200 | 3.13 | >200 | 0.39 | 50 | 50 | 1.56 | 3.13 | 12.5 | 12.5 | 3.13 | 6.25 | 12.5 | 3.13 | 6.25 | 25 | 12.5 | 3.13 | 3.13 | 6.25 |
| 23 | >200 | 50 | >200 | 3.13 | >200 | 50 | 50 | 50 | 0.39 | 0.78 | 3.13 | 3.13 | 1.56 | 1.56 | 3.13 | 3.13 | 3.13 | >200 | 12.5 | 0.39 | 1.56 | 12.5 |
| 24 | 50 | 0.78 | 0.1 | 0.39 | 0.1 | 1.56 | 25 | 50 | <0.05 | 0.39 | <0.05 | 6.25 | 3.13 | 1.56 | 1.56 | 6.25 | 1.56 | 3.13 | 1.56 | 0.39 | 1.56 | 6.25 |
| 25 | 50 | 0.78 | 0.78 | 0.39 | 0.39 | 6.25 | 50 | 50 | 0.39 | 0.78 | 0.39 | 3.13 | 6.25 | 3.13 | 6.25 | 3.13 | 3.13 | 3.13 | 6.25 | 3.13 | 3.13 | 6.25 |
| 26 | >200 | 25 | >200 | 6.25 | >200 | >200 | >200 | >200 | 6.25 | 3.13 | >200 | 50 | 12.5 | 12.5 | 200 | 200 | 25 | 50 | >200 | 50 | 12.5 | >200 |
| 27 | >200 | 200 | 25 | >200 | >200 | 25 | >200 | >200 | 25 | 100 | 25 | 200 | 100 | 100 | 200 | 200 | 100 | >200 | 25 | >200 | >200 | 25 |
| 28 | <0.05 | <0.2 | 0.78 | 0.39 | 0.39 | 1.56 | 1.56 | 25 | 0.78 | 0.3 | 0.78 | 0.78 | 0.78 | 0.2 | 0.78 | 0.39 | 0.78 | 3.13 | 1.56 | 0.05 | 0.2 | 0.1 |
| 29 | >200 | <0.2 | 0.39 | 6.25 | 25 | 12.5 | 12.5 | 100 | 0.39 | 6.25 | 3.13 | 3.13 | 3.13 | 3.13 | 6.25 | 3.13 | 6.25 | 6.25 | 6.25 | 1.56 | 12.5 | — |
| 30 | <0.2 | <0.2 | <0.2 | <0.2 | <0.2 | <0.2 | <0.2 | <0.2 | <0.2 | 0.3 | <0.2 | <0.2 | <0.2 | <0.2 | <0.2 | <0.2 | <0.2 | <0.2 | <0.2 | <0.2 | — | — |

| No. of Organism | 45 | 46 | 47 | 48 | 49 | 50 | 51 | 52 | 53 | 54 | 55 | 56 | 57 | 58 | 59 | 60 | 61 | 62 | 63 | 64 | 65 | 66 |
|---|---|---|---|---|---|---|---|---|---|---|---|---|---|---|---|---|---|---|---|---|---|---|
| 1 | 12.5 | 0.1 | <0.05 | 0.2 | <0.05 | 0.2 | 12.5 | 12 | <0.05 | 0.39 | 1.56 | 1.56 | 1.56 | 3.13 | 6.25 | 3.13 | 3.13 | 12.5 | 3.13 | 0.2 | <0.1 | 12.5 |
| 2 | >200 | 0.39 | 0.2 | 0.39 | <0.05 | 1.56 | 12.5 | 50 | <0.05 | 1.56 | 3.13 | 6.25 | 6.25 | 3.13 | 25 | 12.5 | 12.5 | 50 | 25 | 0.78 | 0.39 | 25 |
| 3 | 12.5 | <0.05 | <0.05 | 0.1 | <0.05 | 0.39 | 6.25 | 25 | <0.05 | 0.2 | 0.78 | 1.56 | 1.56 | 3.13 | 6.25 | 3.13 | 3.13 | 12.5 | 3.13 | 0.2 | <0.1 | 12.5 |
| 4 | >200 | >200 | 200 | — | 12.5 | >200 | 12.5 | 200 | 6.25 | 25 | 200 | 25 | 12.5 | 12.5 | 50 | 25 | — | >200 | >200 | 12.5 | 12.5 | 12.5 |
| 5 | >200 | >200 | 200 | 25 | 50 | >200 | 200 | 200 | 12.5 | 50 | 200 | 25 | 12.5 | 12.5 | 25 | 25 | 12.5 | 3.13 | 3.13 | 25 | 6.25 | 25 |
| 6 | 6.25 | 0.39 | 25 | 25 | 50 | 0.39 | 100 | 200 | 3.13 | 0.2 | 0.39 | 25 | 1.56 | 0.78 | 3.13 | 1.56 | 1.56 | 3.13 | >200 | 12.5 | 6.25 | 50 |
| 7 | 25 | 50 | 0.1 | 0.2 | <0.05 | >200 | 50 | 100 | <0.05 | 6.25 | 25 | 1.56 | 3.13 | 3.13 | 12.5 | 12.5 | 6.25 | 50 | 3.13 | 0.2 | 1.56 | 6.25 |
| 8 | >200 | 50 | 3.13 | 3.13 | <0.05 | 50 | 50 | 50 | 1.56 | 3.13 | 12.5 | 12.5 | 3.13 | 6.25 | 12.5 | 3.13 | 6.25 | 25 | 12.5 | 3.13 | 3.13 | 6.25 |
| 9 | >200 | 50 | 3.13 | 3.13 | <0.05 | 25 | 50 | 50 | 0.39 | 0.78 | 3.13 | 3.13 | 1.56 | 1.56 | 3.13 | 3.13 | 3.13 | >200 | 12.5 | 0.39 | 1.56 | 12.5 |
| 10 | >200 | 0.78 | 0.1 | 0.39 | 0.1 | 1.56 | 25 | 50 | <0.05 | 0.39 | <0.05 | 6.25 | 3.13 | 1.56 | 1.56 | 6.25 | 1.56 | 3.13 | 1.56 | 0.39 | 1.56 | 6.25 |
| 11 | 50 | 0.39 | 0.1 | 0.39 | <0.05 | 6.25 | 50 | 50 | 0.39 | 0.78 | <0.05 | 3.13 | 6.25 | 3.13 | 6.25 | 3.13 | 3.13 | 3.13 | 6.25 | 3.13 | 3.13 | 6.25 |
| 12 | >200 | 200 | 50 | 1.56 | >200 | >200 | >200 | >200 | 6.25 | 3.13 | 25 | 50 | 12.5 | 12.5 | 200 | 200 | 25 | 50 | >200 | 50 | 12.5 | >200 |
| 13 | >200 | 25 | 25 | >200 | 12.5 | 25 | >200 | >200 | 25 | 100 | 25 | 200 | 100 | 100 | 200 | 200 | 100 | >200 | 25 | >200 | >200 | 25 |
| 14 | >200 | 6.25 | 0.78 | 6.25 | 0.78 | 6.25 | 50 | >200 | 6.25 | 3.13 | 25 | 12.5 | 6.25 | 12.5 | 12.5 | 12.5 | 25 | 25 | 50 | 6.25 | 25 | 25 |
| 15 | >200 | >200 | >200 | >200 | >200 | >200 | >200 | >200 | 3.13 | >200 | >200 | >200 | >200 | >200 | >200 | >200 | >200 | >200 | >200 | >200 | >200 | >200 |
| 16 | >200 | >200 | >200 | >200 | >200 | >200 | >200 | >200 | <0.05 | >200 | >200 | >200 | >200 | >200 | >200 | >200 | >200 | >200 | >200 | >200 | >200 | >200 |
| 17 | 100 | 1.56 | >200 | >200 | 12.5 | 1.56 | 1.56 | 12.5 | 3.13 | 0.05 | <0.05 | 3.13 | 1.56 | 1.56 | 3.13 | 1.56 | 1.56 | 3.13 | 1.56 | >200 | 1.56 | 3.13 |
| 18 | >200 | 1.56 | >200 | 12.5 | >200 | >200 | >200 | 12.5 | >200 | 0.39 | >200 | >200 | 1.56 | 12.5 | >200 | >200 | >200 | >200 | >200 | >200 | >200 | 200 |
| 19 | 0.78 | >200 | >200 | >200 | <0.05 | 1.56 | >200 | 50 | <0.05 | >200 | 6.25 | 12.5 | 1.56 | 12.5 | 6.25 | >200 | 12.5 | 3.13 | 1.56 | >200 | 3.13 | 3.13 |
| 20 | 0.78 | 0.39 | <0.05 | 0.39 | <0.05 | 6.25 | 12.5 | 50 | <0.05 | 0.39 | <0.05 | 3.13 | 3.13 | 1.56 | 1.56 | 0.39 | 3.13 | 3.13 | 1.56 | 0.2 | 0.2 | 3.13 |
| 21 | >200 | 200 | 200 | >200 | >200 | >200 | >200 | >200 | 0.78 | 0.3 | 25 | 200 | 100 | 100 | 200 | 200 | 25 | >200 | 6.25 | 3.13 | 100 | >200 |
| 22 | >200 | >200 | >200 | >200 | >200 | >200 | >200 | >200 | >200 | 6.25 | >200 | >200 | >200 | >200 | >200 | >200 | >200 | >200 | >200 | >200 | >200 | >200 |
| 23 | >200 | >200 | >200 | >200 | >200 | >200 | >200 | >200 | 3.13 | >200 | 6.25 | >200 | 3.13 | 12.5 | 3.13 | 12.5 | 12.5 | 12.5 | 3.13 | 6.25 | >200 | >200 |
| 24 | 100 | <0.05 | 25 | 25 | 0.05 | 1.56 | 1.56 | 25 | <0.05 | 0.05 | <0.05 | 200 | 0.1 | 100 | 6.25 | 0.39 | 6.25 | 6.25 | 6.25 | 6.25 | >200 | >200 |
| 25 | <0.05 | <0.05 | 0.39 | 0.39 | <0.05 | <0.05 | 12.5 | 100 | 0.39 | 0.39 | 6.25 | 3.13 | 3.13 | 12.5 | 12.5 | 3.13 | 12.5 | 12.5 | 25 | 25 | 25 | 3.13 |
| 26 | >200 | 3.13 | 3.13 | 0.39 | 0.39 | 1.56 | 12.5 | 50 | <0.05 | 0.39 | 6.25 | 6.25 | 3.13 | 12.5 | 6.25 | 3.13 | 6.25 | 6.25 | 6.25 | >200 | 3.13 | 3.13 |
| 27 | <0.2 | <0.2 | <0.2 | <0.2 | <0.2 | <0.2 | <0.2 | <0.2 | <0.2 | <0.2 | <0.2 | <0.2 | <0.2 | <0.2 | <0.2 | <0.2 | <0.2 | <0.2 | <0.2 | 0.05 | 0.2 | 0.1 |
| 28 | <0.2 | <0.2 | <0.2 | <0.2 | <0.2 | <0.2 | <0.2 | <0.2 | <0.2 | 0.79 | <0.2 | <0.2 | <0.2 | <0.2 | <0.2 | <0.2 | <0.2 | <0.2 | <0.2 | <0.2 | <0.2 | <0.2 |
| 29 | 3.13 | 1.56 | 1.56 | 3.13 | 1.56 | 0.79 | 12.5 | 100 | 0.79 | 0.79 | 3.13 | 50 | 50 | 12.5 | 12.5 | 25 | 25 | 100 | 100 | 0.39 | 12.5 | 25 |
| 30 | 3.13 | 3.13 | 3.13 | 3.13 | 3.13 | 1.56 | 100 | 100 | 1.56 | 1.56 | 3.13 | 50 | 50 | 12.5 | 12.5 | 100 | 100 | 100 | 100 | 6.25 | 50 | 50 |

No. of Compound

α-substituted

TABLE 2-continued

Minimum Inhibitory Concentration

| No. of Organism | 67 | 68 | 69 | 70 | 71 | 72 | 73 | 74 | 75 | 76 | 77 | 78 | 79 | 80 | 81 | 82 | acrylic acid |
|---|---|---|---|---|---|---|---|---|---|---|---|---|---|---|---|---|---|
| 1 | <0.05 | 3.13 | 100 | 0.39 | 1.56 | 1.56 | 0.78 | 0.78 | 0.39 | 0.39 | >200 | 50 | 0.39 | 0.39 | 25 | <0.05 | 25 |
| 2 | 0.2 | 25 | >200 | 0.78 | 12.5 | 6.25 | 1.56 | 6.25 | 1.56 | 1.56 | >200 | 200 | 0.78 | 1.56 | 25 | 0.2 | 50 |
| 3 | <0.05 | 6.25 | 100 | 0.39 | 6.25 | 3.13 | 1.56 | 1.56 | 0.78 | 0.78 | >200 | 50 | 0.39 | 0.78 | 12.5 | <0.05 | 25 |
| 4 | — | 200 | >200 | 1.56 | 12.5 | 12.5 | 100 | 100 | >200 | 100 | >200 | 100 | 3.13 | 6.25 | 25 | 0.78 | 25 |
| 5 | >200 | 25 | >200 | >200 | >200 | 50 | >200 | >200 | >200 | >200 | >200 | 100 | >200 | >200 | 12.5 | 12.5 | 12.5 |
| 6 | >200 | 200 | >200 | >200 | >200 | 50 | >200 | >200 | >200 | >200 | >200 | 100 | >200 | >200 | 12.5 | 12.5 | 12.5 |
| 7 | 3.13 | 25 | >200 | 1.56 | >200 | 3.13 | 1.56 | 1.56 | 0.78 | 0.78 | 100 | 200 | 3.13 | 0.78 | 200 | 0.39 | 50 |
| 8 | >200 | 200 | >200 | >200 | >200 | 25 | 50 | 12.5 | >200 | 25 | >200 | 100 | >200 | 100 | 12.5 | 6.25 | 12.5 |
| 9 | 100 | 25 | >200 | 3.13 | 12.5 | 12.5 | 0.39 | 1.56 | 0.78 | 0.78 | >200 | 25 | 3.13 | 12.5 | 6.25 | 0.78 | 6.25 |
| 10 | 100 | 6.25 | 200 | >200 | 100 | 3.13 | >200 | >200 | 1.56 | 1.56 | >200 | 50 | 3.13 | 3.13 | 12.5 | 0.78 | 12.5 |
| 11 | 100 | 12.5 | >200 | >200 | 200 | 6.25 | >200 | 3.13 | 1.56 | 1.56 | >200 | 50 | 6.25 | 3.13 | 12.5 | 0.78 | 12.5 |
| 12 | 200 | 25 | >200 | >200 | >200 | 12.5 | >200 | 200 | >200 | >200 | >200 | 50 | >200 | 12.5 | 6.25 | 0.78 | 12.5 |
| 13 | >200 | 6.25 | >200 | >200 | >200 | 100 | >200 | >200 | 200 | >200 | >200 | >200 | >200 | 200 | >200 | 50 | 3.13 |
| 14 | 50 | 100 | >200 | 3.13 | >200 | 12.5 | 12.5 | 6.25 | 1.56 | 12.5 | 100 | 100 | 1.56 | 6.25 | 50 | 6.25 | 25 |
| 15 | >200 | >200 | >200 | >200 | >200 | >200 | >200 | >200 | >200 | >200 | >200 | >200 | >200 | >200 | 200 | >200 | 200 |
| 16 | >200 | >200 | >200 | >200 | >200 | >200 | >200 | >200 | >200 | >200 | >200 | >200 | >200 | >200 | 200 | >200 | 200 |
| 17 | >200 | >200 | >200 | >200 | 12.5 | 6.25 | 12.5 | 6.25 | 3.13 | 3.13 | 200 | 50 | >200 | 6.25 | 25 | 0.78 | 200 |
| 18 | 100 | 6.25 | >200 | 6.25 | >200 | 6.25 | >200 | >200 | >200 | >200 | 100 | 50 | 6.25 | >200 | 100 | >200 | 12.5 |
| 19 | >200 | 200 | >200 | >200 | >200 | >200 | >200 | >200 | >200 | >200 | >200 | 50 | >200 | >200 | 50 | >200 | 12.5 |
| 20 | 50 | 12.5 | 100 | 1.56 | 6.25 | 6.25 | 1.56 | 1.56 | 1.56 | 1.56 | >200 | 50 | 1.56 | 1.56 | 6.25 | 0.2 | 6.25 |
| 21 | 3.13 | 6.25 | 50 | 1.56 | 6.25 | 6.25 | 0.78 | 1.56 | 0.78 | 0.78 | >200 | 50 | 1.56 | 1.56 | 12.5 | 0.1 | 6.25 |
| 22 | >200 | 200 | >200 | >200 | >200 | 200 | >200 | 100 | >200 | 100 | >200 | 200 | >200 | >200 | 100 | >200 | 50 |
| 23 | >200 | >200 | >200 | >200 | >200 | >200 | >200 | >200 | >200 | >200 | 50 | 100 | >200 | >200 | >200 | >200 | 200 |
| 24 | >200 | >200 | 100 | >200 | >200 | 200 | >200 | >200 | 200 | 200 | 6.25 | 3.13 | >200 | >200 | 100 | >200 | 100 |
| 25 | <0.05 | 6.25 | 50 | — | 12.5 | 50 | 1.56 | 12.5 | 0.78 | 50 | 3.13 | >200 | 0.78 | 3.13 | 100 | 12.5 | 6.25 |
| 26 | 1.56 | 12.5 | — | — | — | — | — | — | 1.56 | 1.56 | >200 | 3.13 | 0.78 | 1.56 | 6.25 | 1.56 | 50 |
| 27 | 1.56 | 200 | — | — | — | — | — | 12.5 | 1.56 | 1.56 | >200 | >200 | 0.78 | 1.56 | 12.5 | 1.56 | 6.25 |
| 28 | <0.2 | <0.2 | >200 | 1.56 | 12.5 | 6.25 | 12.5 | 12.5 | <0.2 | <0.2 | 3.13 | 3.13 | <0.2 | <0.2 | <0.2 | <0.2 | <0.2 |
| 29 | 12.5 | 100 | 100 | 1.56 | 12.5 | 6.25 | 12.5 | 12.5 | 200 | 25 | >200 | >200 | 0.39 | 0.39 | 12.5 | 0.39 | 12.5 |
| 30 | 50 | 100 | 100 | 6.25 | 200 | 100 | 12.5 | 12.5 | 200 | 100 | 200 | 200 | 3.13 | 3.13 | 6.25 | 3.13 | 25 |

TABLE 3

| No. | Species | Strain | Official deposition No. |
|---|---|---|---|
| 1 | Staphylococcus aureus | | FDA 209PJc-1 |
| 2 | Staphylococcus aureus | Terajima | |
| 3 | Staphylococcus aureus | | MS 353 |
| 4 | Streptococcus pyogenes | Cook | |
| 5 | Escherichia coli | | NIHJ-JC-2 |
| 6 | Escherichia coli | K12 C600 | IAM 1264 |
| 7 | Klebsiella pneumoniae | | PCI-602 |
| 8 | Salmonella typhimurium | | IID 971 |
| 9 | Salmonella typhi | 901 | |
| 10 | Salmonella paratyphi-A | 1015 | |
| 11 | Salmonella shottmuelleri | 8006 | |
| 12 | Salmonella enteritidis | G 14 | |
| 13 | Serratia marcescens | | IAM 1184 |
| 14 | Bacillus subtilis | | ATCC 6633 |
| 15 | Pseudomonas aeruginosa | | IFO 3445 |
| 16 | Pseudomonas aeruginosa | | NCTC 10490 |
| 17 | Pseudomonas aeruginosa | | PAO 1 |
| 18 | Proteus morganii | | IFO 3848 |
| 19 | Proteus mirabilis | | IFO 3849 |
| 20 | Proteus vulgaris | OX-19 | |
| 21 | Proteus vulgaris | HX-19 | |
| 22 | Proteus rettgeri | | IFO 3850 |
| 23 | Enterobacter aerogenes | | ATCC 13048 |
| 24 | Enterobacter cloacae | 963 | |
| 25 | Micrococcus luteus | | ATCC 9341 |
| 26 | Streptococcus pyogenes | | IFO 3340 |
| 27 | Streptococcus faecium | | IFO 3826 |
| 28 | Mycoplasma pneumoniae | | |
| 29 | Candida albicans | | IAM 4905 |
| 30 | Aspergillus niger | | IFO 6342 |

As are seen in Table 2, each of the present compounds shows an antibacterial activity against both Gram-positive bacteria and Gram-negative bacteria, antifungal activity against *Candida albicans* and *Aspergillus niger* and shows antimycoplasmal activity against *Mycoplasma pneumoniae* and accordingly, the present compound can be used as a therapeutic medicine and a disinfectant.

In the case where the present compound is used as a pharmaceutical preparation, the compound is contained therein as an active ingredient in the range of from 0.01 to 100% by weight in general. In the case where the present compound is used as an active ingredient of the pharmaceutical composition, the compound can be used as a mixture with a pharmaceutically allowable carrier(s). As such a carrier, an inert organic- or inorganic carrier material such as water, gelatin, gum arabic, lactose, starch, magnesium stearate, talc, vegetable oils, polyalkylene glycol, vaselinum flavum, etc. may be mentioned. In addition, in the pharmaceutical preparation, another medicine and/or adjuvants, for instance, preservative, stabilizer, wetting agent, emulsifier, osmotic pressure-regulator, buffer, etc. may be contained.

The present compound is administered orally or parenterally and accordingly, the pharmaceutical preparation containing thereof can take an optional form or shape, for instance, a solid form (powder, granule, tablet, sugar-coated tablet, capsule, sappository, etc.), a semi-solid form (ointment, etc.) and a liquid form (suspension, solution, emulsion, ampoule, injection, etc.).

Although the dose rate of the present compound depends on the age, the state of illness and the individual difference of the patient, of course, in the case when it is administered orally to a human being, the rate is in the range of from 100 to 1000 mg/day for an adult of 60 kg in body weight, preferably, from 250 to 500 mg/day. In the parenterally administered case, the rate is in the range of from 50 to 500 mg for an adult of 60 kg in body weight, preferably, from 100 to 200 mg/day. The daily dose is generally divided into from one to four portions.

The present invention will be explained more in detail while referring to the following non-limitative examples.

EXAMPLE 1

Synthesis of Compound No. 4 according to the present invention

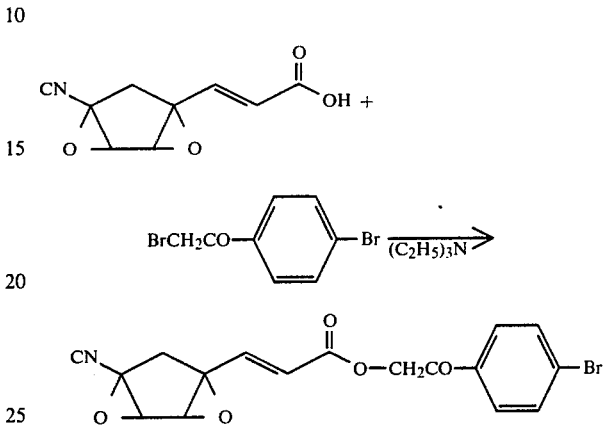

After dissolving 197 mg (1.02 mmol) of β-substituted acrylic acid represented by the formula (II) in 20 ml of methylene chloride, 512 mg (1.84 mmol) of p-bromophenacyl bromide and 250 μl (1.80 mmol) of triethylamine were added to the thus prepared solution and the mixture was reacted for 10 min by heating thereof under a reflux condenser. After the reaction was over, the solvent was distilled off from the reaction mixture, and the residue was subjected to silica gel chromatography while using methylene chloride as a developing solvent, thereby obtaining the product, which was recrystallized from a mixed solvent of n-hexane and methylene chloride to obtain 349 mg of acicular crystaline p-bromophenacyl β-substituted acrylate (Compound No. 4). The physicochemical properties of Compound No. 4 are shown in Table 1.

EXAMPLE 2

Synthesis of Compound No. 2 according to the present invention

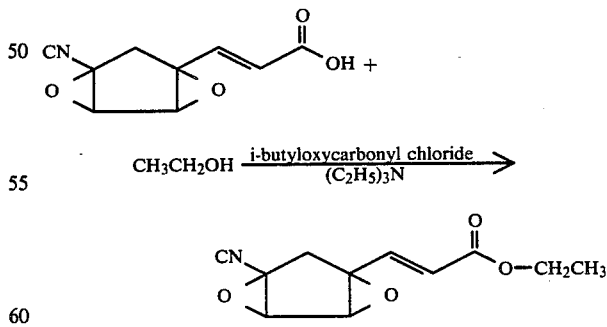

Into a solution of 193 mg (1.0 mmol) of β-substituted acrylic acid in 30 ml of methylene chloride, 147 μl (1.05 mmol) of triethylamine were added, and while stirring the mixture at −15° to −10° C., 136 μl (1.05 mmol) of isobutyloxycarbonyl chloride were added thereto, and after 15 min, 62 μl (1.05 mmol) of ethanol were added also to the mixture. After reacting the mixture by stirring thereof for one hour at a sub-zero temperature and continuing the stirring for a night at room temperature, the solvent was distilled off from the reaction mixture, and the residue was subjected to silica gel chromatography while using methylene chloride as a developing solvent to separate and purify the reaction product, thereby obtaining 176.8 mg of oily ethyl β-substituted acrylate (Compound No. 2). The product was preserved as a solution in methylene chloride because of its decomposing and colouring tendency in a non-solvent state. The physicochemical properties of Compound No. 2 are shown in Table 1.

EXAMPLE 3

Syntheses of Compounds Nos. 16 and 17 according to the present invention

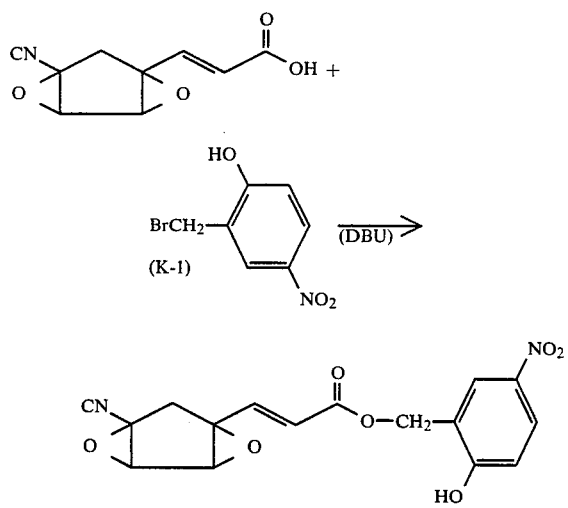

Into a solution of 100 mg (0.52 mmol) of β-substituted acrylic acid in 5 ml of methylene chloride, 180 mg (0.78 mmol) of Koshland's reagent No. 1 represented by the formula (K-1) and 0.08 ml (0.52 mmol) of 1,8-diazabicyclo[5,4,0]-7-undecene were added, and the mixture was stirred for 30 min at room temperature to react the mixture. After the reaction was over, the solvent was distilled off from the reaction mixture, and the residue was subjected to silica gel chromatography while using methylene chloride as a developing solvent, thereby separating and purifying the reaction product, to obtain about 140 mg of the object product (Compound No. 17) as an oily matter. The physicochemical properties are shown in Table 1. The thus obtained Compound No. 17 was preserved as a solution in methylene chloride because of the tendency thereof of decomposition in a non-solvent state.

In a similar manner to above except for using Koshland's reagent No. 2 represented by the formula:

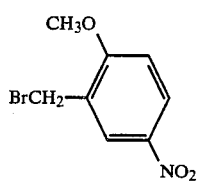

Compound No. 16 was obtained as an oily matter.

EXAMPLE 4

Synthesis of Compound No. 10 according to the present invention

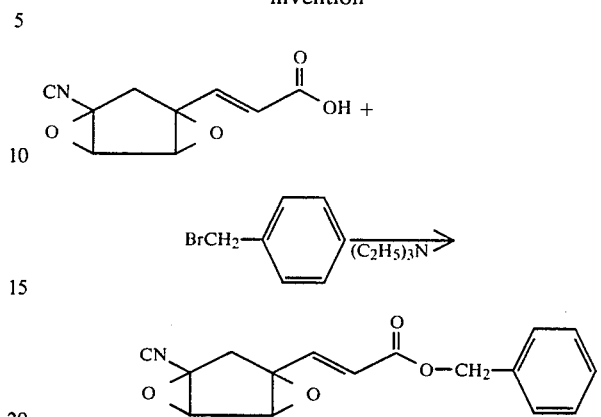

Into a solution of 87 mg (0.45 mmol) of β-substituted acrylic acid in 5 ml of methylene chloride, 56 μl (0.47 mmol) of benzyl bromide and 66 μl (0.47 mmol) of triethylamine were added, and the mixture was reacted by heating under a reflux condenser for about 20 min.

After the reaction was over, the reaction mixture was concentrated, and the concentrate was subjected to silica gel chromatography while using methylene chloride as the developing solvent for purification of the reaction product, thereby obtaining 41.1 mg of the objective compound, benzyl β-substituted acrylate, as an oily material which decomposed and coloured when left in a non-solvent state. For preservation of the product, it was made to be a solution in methylene chloride. The physicochemical properties are shown in Table 1.

EXAMPLE 5

Synthesis of Compound No. 9 according to the present invention

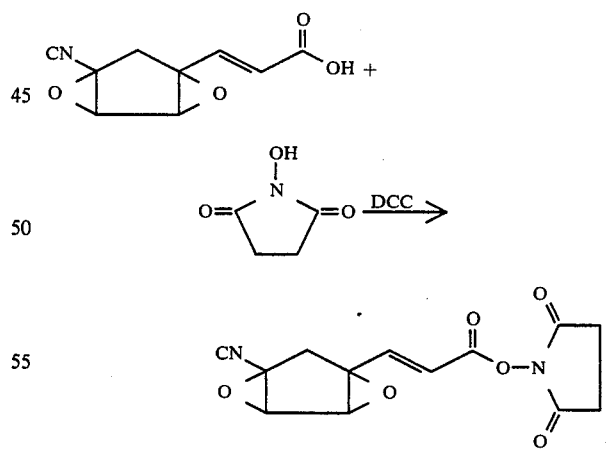

In a solution of 573 mg (3.0 mmol) of β-substituted acrylic acid and 358 mg (3.1 mmol) of N-hydroxysuccinimide in 60 ml of methylene chloride, a solution of 655 mg of dicyclohexylcarbodiimide (DCC) in 15 ml of methylene chloride was added dropwise at 20° to 25° C. After stirring the mixture at the same temperature as above for 3 hours, the thus crystallized dicyclohexylurea was removed by filtration with a glass-filter (grade of 3G4), and after concentrating the thus obtained filtrate to 10 to 20 ml, the concentrate was subjected to silica gel chromatography while using a 10:1 by volume mixed solvent of methylene chloride and ethyl acetate as the developing solvent to completely remove the remaining dicyclohexylurea.

By collecting the fractions containing the objective compound and concentrating the thus collected fractions to about 10 ml, 788 mg of crystals of the objective compound which decomposed and coloured at a temperature of higher than 115° C. were obtained. The physicochemical properties of the object compound are shown in Table 1.

EXAMPLE 6

Synthesis of Compound No. 19 according to the present invention

Into a solution of 196 mg (1.01 mmol) of β-substituted acrylic acid in 30 ml of methylene chloride, an equimolar amount (147 μl) of triethylamine was added. After adding 137 μl of isobutyl chloroformate while following a conventional method to the solution to convert the reaction mixture into a mixed acid anhydride at −12° to −15° C., gaseous ammonia was introduced into the reaction mixture at the same temperature as above. After having confirmed the disappearance of the mixed acid anhydride by testing the reaction mixture with TLC (silica gel and methylene chloride), the solvent was distilled off from the reaction mixture under a reduced pressure, and the residue was dissolved in a small amount of a mixed solvent (15:1 by volume) of methylene chloride and methanol, and the solution was subjected to silica gel chromatography to purify the reaction product (Rf of 0.28). The thus obtained crude amide was recrystallized from a mixed solvent of acetone and n-hexane to obtain 159 mg of colourless acicular crystals of Compound No. 19 of a melting point of higher than 120° C. with decomposition in a yield of 82%.

EXAMPLE 7

Syntheses of Compounds Nos. 25 and 36 according to the present invention by DCC direct process Into a solution of 306 mg (1.59 mmol) of β-substituted acrylic acid in 16 ml of methylene chloride, a solution of 345 mg of dicyclohexylcarbodiimide in 10 ml of methylene chloride was added dropwise at room temperature.

After leaving the mixture to react for 10 to 20 min, a solution of 155 mg of aniline in 10 ml of methylene chloride was added to the mixture dropwise in 30 min at room temperature. After the reaction was over, the reaction mixture was filtered to collect the filtrate and the filtrate was concentrated and subjected to silica gel chromatography while using a mixed solvent (20:1 by volume) of methylene chloride and ethyl acetate. Thereby, both 132 mg of Compound No. 36 as an amide corresponding to Rf value of 0.33 and 233 mg of Compound No. 25 as an addition product with DCC corresponding to Rf value of 0.25 were obtained, respectively in a yield of 31% and 37%.

EXAMPLE 8

Synthesis of Compound No. 36 according to the present invention by a mixed acid anhydride process Into a solution of 1159 mg (6 mmol) of 62-substituted acrylic acid in 80 ml of methylene chloride, 879 μl of triethylamine were added and, further 817 μl of isobutyl chloroformate (hereinafter referred to as IBCF) were added to the mixture dropwise at a temperature of from −15° to −10° C., and the mixture was reacted at the same temperature as above for 20 to 30 min. Then, a solution of 793 μl of aniline in 20 ml of methylene chloride was added to the mixture in 15 min, and after heating the mixture to room temperature, the mixture was reacted for 3 to 12 hours. After the reaction was over, the solvent in the reaction mixture was distilled off from the mixture under a reduced pressure, and the residue was subjected to silica gel chromatography while using a mixture (20:1 by volume) of methlene chloride and ethyl acetate as the developing solvent to obtain a roughly purified reaction product. By recrystallizing the thus roughly purified product from a mixed solvent of hexane and methylene chloride, 1121.2 mg of fine acicular crystals of Compound No. 36 were obtained in a yield of 70%.

EXAMPLE 9

Synthesis of Compound No. 24 according to the present invention

Into a solution of 193 mg of β-substituted acrylic acid and 115 mg of N-hydroxysuccinimide in 40 ml of methylene chloride, a solution of 207 μl of dicyclohexylcarbodiimide (DCC) in 10 ml of methylene chloride was added dropwise while cooling the solution by ice-water. After 30 min of the addition, ice-water bath was remoed and the mixture was stirred for 3 to 12 hours at room temperature.

After separating the thus crystallized dicyclohexylurea from the reaction mixture by filtration, a solution of 109 μl of benzylamine in 5 ml of methylene chloride was added to the thus prepared filtrate. After the reaction was over, the solvent was distilled from the reaction mixture and the residue was concentrated to 10 ml, and about 2 times by volume of n-hexane (20 ml) was added to the concentrate. After leaving the mixture for one hour, the separted precipitate was collected by filtration, and after dissolving the collected precipitate in a small amount of a mixture (20:1 by volume) of methylene chloride and ethyl acetate, the solution was subjected to silica gel chromatography while using a mixed solvent (20:1 by volume) of methylene chloride and ethyl acetate for purifying the precipitate, and the thus purified matter was recrystallized from a mixed solvent of methylene chloride and hexane to obtain 240 mg of acicular crystals of the objective product, Compound No. 24, in a yield of 85%. The acicular crystals melted with decomposition and coloration at a temperature of higher than 160° C.

EXAMPLE 10

Syntheses of Compounds Nos. 26, 27, 28 and 29 according to the present invention Both 193 mg (1 mmol) of β-substituted acrylic acid and 115 mg (1 mmol) of N-hydroxysuccinimide were dissolved in 15 ml of methylene chloride to obtain an active ester under the same conditions in Example 9. To the thus obtained solution of the active ester, a free base prepared preliminarily from a hydrochloride (or a p-toluenesulfonate) of a corresponding amino acid to that in Example 9 and an organic base (for instance, triethylamine) was added dropwise at room temperature. After carrying out the reaction for 12 to 24 hours, the solvent was distilled off from the reaction mixture, and the residue was concentrated. After preliminary purifying the concentrate by subjecting thereof to short silica gel column-chromatography while using a mixed solvent (10:1 by volume) of methylene chloride and ethyl acetate, the eluate was concentrated to 5 to 7 ml and 2 times by volume of n-hexane were added to the concentrate. The precipitate was purified by silica gel chromatography while using a mixed solvent (20:1 by volume) of methylene chloride and ethyl acetate, and the thus preliminarily purified substance was further purified by recrystallization from a mixed solvent of hexane and methylene chloride to obtain 156.6 mg of fine acicular crystals of the object Compound No. 26 in a yield of 45%.

In a similar manner, the following compounds were obtained.

| Compound No. (according to the present invention) | Amount obtained (mg) | Yield (%) |
|---|---|---|
| No. 27 | 100 | 30 |
| No. 28 | 478 | 61 |
| No. 29 | 394 | 52 |

The salt of amino acid for preparation of the free base in syntheses of Compounds Nos. 27, 28 and 29 was as follows:

dimethyl asparaginate hydrochloride for Compound No. 27, dibenzyl glutamate p-toluenesulfochloride for Compound No. 28 and dibenzyl asparaginate p-toluenesulfochloride for Compound No. 29.

EXAMPLE 11

Syntheses of Compounds Nos. 33, 34 and 35 according to the present invention

Into a solution of 47.5 mg (0.25 mmol) of β-substituted acrylic acid in 2 ml of methylene chloride, a solution of 51.2 mg of dicyclohexylcarbodiimide in 2 ml of methylene chloride was added dropwise at room temperature. After one hour of the addition, a solution of 103 mg of p-bromophenacyl 6-aminopenicillanate (refer to P. Brmberg et al. "Acta Chem. Scand." Vol. 21, page 2210 (1967)) was added to the mixture dropwise. After the reaction was over, the separated dicyclohexylurea was removed from the reaction mixture by filtration, and after adding about 1.5 times by volume of n-hexane to the filtrate, the precipitate was collected by filtration. By purifying the precipitate in silica gel chromatography while using a mixed solvent (20:1 by volume) of methylene chloride and ethyl acetate, recrystallizing the thus obtained substance from a mixed solvent of methylene chloride and hexane, 72.4 mg of the object Compound No. 33 were obtained as fine acicular crystals in a yield of 50%.

In a similar manner, the following Compounds according to the present invention were obtained:

| No. of Compound according to the present invention | Amount obtained (mg) | Yield (%) |
|---|---|---|
| No. 34 | 4.2 | 2.9 |
| No. 35 | 53 | 35 |

What is claimed is:

1. β-(4-isocyano-1,2-3,4-diepoxycyclopentyl)acrylamide.

2. A pharmaceutical composition having antibacterial activity, antifungal activity or antimycoplasmal activity in dosage unit form which comprises a dosage effective to produce the activities of a derivative of β-(4-isocyano-1,2-3,4-diepoxycyclopentyl)acrylic acid represented by formula (I):

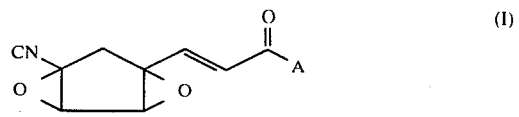

wherein the derivative is β-(4-isocyano-1,2-3,4-diepoxycyclopentyl)acrylamide.

3. A derivative of β-(4-isocyano-1,2-3,4-diepoxycyclopentyl)acrylic acid represented by the formula (I):

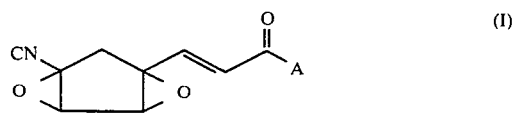

wherein A represents $$-OR \qquad (1)$$

wherein R represents

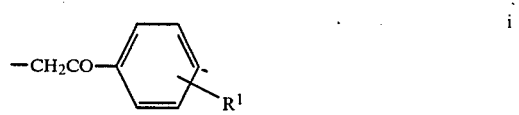

wherein $R^1$ represents a hydrogen atom, a chlorine atom, a bromine atom, a methyl group or a methoxy group or

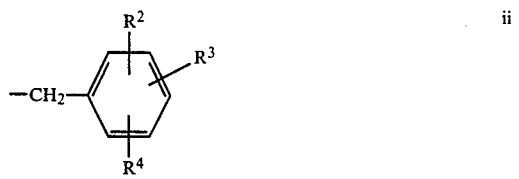

wherein $R^2$, $R^3$ and $R^4$ are the same or different from each other and represent respectively a hydrogen atom, a nitro group, a methyl group, or a methoxy group, or

wherein X and Y may be the same or different from each other and represent respectively a hydrogen atom, a phenyl group, a cyclohexyl group, a methylphenyl group, a fluorophenyl group, a chlorophenyl group, a bromophenyl group, an iodophenyl group, a 3-trifluoromethylphenyl group, a 4-trifluoromethylphenyl group, a 3-nitrophenyl group, a 3-methoxycarbonylphenyl group, a 4-methoxycarbonylphenyl group, a 4-carboxyphenyl group, a methoxyphenyl group, a hydroxyphenyl group, an aminophenyl group, a 4-sulfamidophenyl group, a 4-propoxyphenyl group, a 4-isopropoxyphenyl group, a 4-methylthiophenyl group, a 4-benzoylphenyl group, a 4-acetylphenyl group,

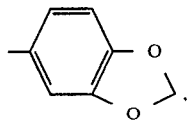

a benzyl group, a methoxy group, a benzyloxy group, a 2-hydroxyethyl group,

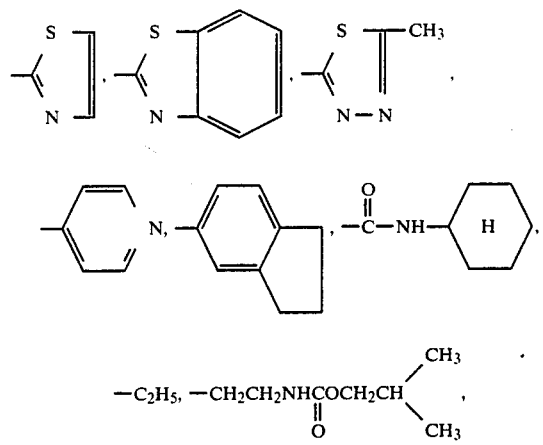

$-C_2H_5, -CH_2CH_2NHCOCH_2CH\begin{matrix}CH_3\\CH_3\end{matrix}$,

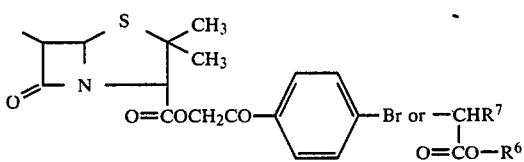

wherein $R^6$ represents a benzyl group and $R^7$ represents a methoxycarbonylmethyl group, a 2-methoxycarbonylethyl group, a benzyloxycarbonylmethyl group or a 2-benzoyloxycarbonylethyl group, or X and Y may form a ring together with N.

4. A derivative of β-(4-isocyano-1,2,3,4-diepoxycyclopentyl)acrylic acid represented by the formula (I):

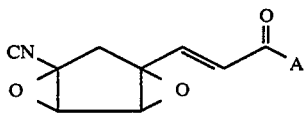

wherein A represents

—OR    (1)

wherein R represents

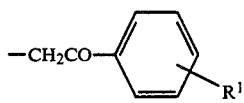

wherein $R^1$ represents a hydrogen atom, a chlorine atom, a bromine atom, a methyl group or a methoxy group or

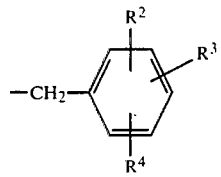

wherein $R^2$, $R^3$ and $R^4$ are the same or different from each other and represent respectively a hydrogen atom, a methyl group or a methoxy group or

wherein X and Y may be the same or different from each other and represent respectively a hydrogen atom, phenyl group, a cyclohexyl group, a methylphenyl group, a fluorophenyl group, a chlorophenyl group, a bromophenyl group, a 3-trifluoromethylphenyl group, a 4-trifluoromethylphenyl group, a 3-nitrophenyl group, a 3-methoxycarbonylphenyl group, a 4-methoxycarbonylphenyl group, a methoxyphenyl group, a 4-benzoylphenyl group, a 4-acetylphenyl group, a benzyl group, a benzyloxy group,

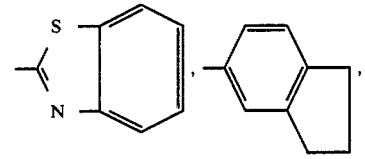

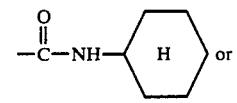

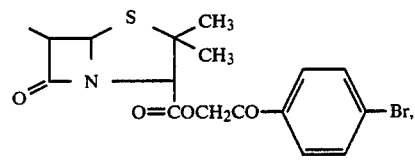

5. A compound represented by formula (I):

wherein A represents

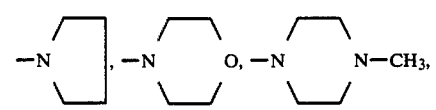

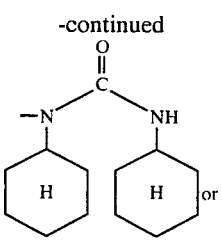 or

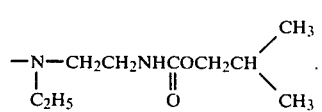

6. A pharmaceutical composition having antibacterial activity, antifungal activity or antimycoplasmal activity in dosage unit form which comprises a dosage effective to produce the activities of a derivative of β-(4-isocyano-1,2-3,4-diepoxycyclopentyl)acrylic acid represented by the formula (I):

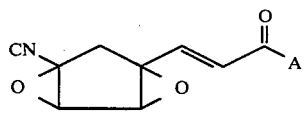 (I)

wherein A represents

—OR (1)

wherein R represents

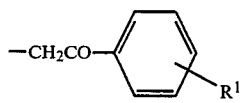 i wherein $R^1$ represents a hydrogen atom, a chlorine atom, a bromine atom, a methyl group or a methoxy group or

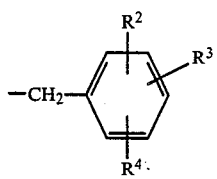 ii wherein $R^2$, $R^3$ and $R^4$ are the same or different from each other and represent respectively a hydrogen atom, a nitro group, a methyl group or a methoxy group or

 (2)

wherein X and Y may be the same or different from each other and represent respectively a hydrogen atom, a phenyl group, a cyclohexyl group, a methylphenyl group, a fluorophenyl group, a chlorophenyl group, a bromophenyl group, an iodophenyl group, a 3-trifluoromethylphenyl group, a 4-trifluoromethylphenyl group, a 3-nitrophenyl group, a 3-methoxycarbonylphenyl group, a 4-methoxycarbonylphenyl group, a 4-carboxyphenyl group, a methoxyphenyl group, a hydroxyphenyl group, an aminophenyl group, a 4-sulfamidophenyl group, a 4-propoxyphenyl group, a 4-isopropoxyphenyl group, a 4-methylthiophenyl group, a 4-benzoylphenyl group, a 4-acetylphenyl group, a benzyl group, a methoxy group, a benzyloxy group, a 2-hydroxyethyl group,

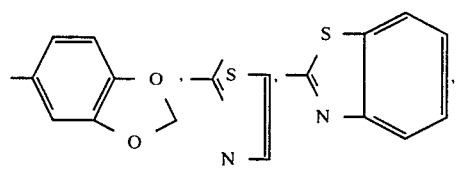

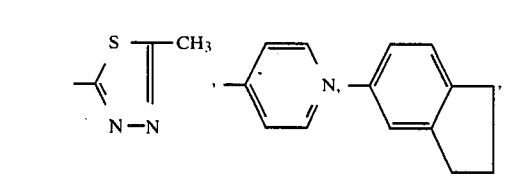

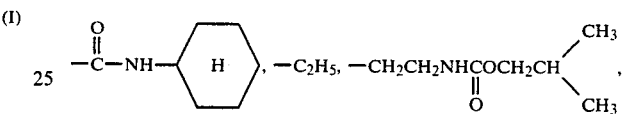

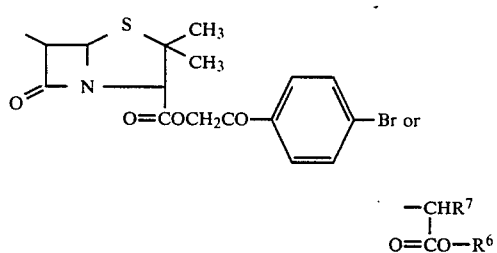

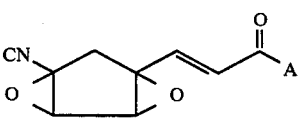 or

—CHR$^7$
|
O=CO—R$^6$ wherein $R^6$ represents a benzyl group and $R^7$ represents a methoxycarbonylmethyl group, a 2-methoxycarbonylethyl group, a benzyloxycarbonylmethyl group or a 2-benzoyloxycarbonylethyl group or X and Y may form a ring together with N, and a pharmaceutically acceptable carrier.

7. A pharmaceutical composition having antibacterial activity, antifungal activity and antimycoplasmal activity in dosage unit form which comprises a dosage effective to produce the activities of a derivatives of β-(4-isocyano-1,2-3,4-diepoxycyclopentyl)acrylic acid represented by the formula (I):

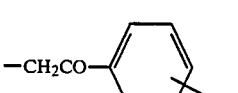 (I)

wherein A represents

—OR (1)

wherein R represents

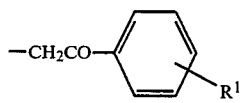 i

—CH$_2$CO—⟨phenyl⟩—R$^1$ wherein R¹ represents a hydrogen atom, a chlorine atom, a bromine atom, a methyl group or a methoxy group or

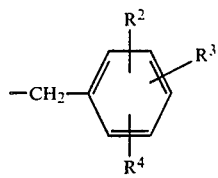

wherein R², R³ and R⁴ are the same or different from each other and represent respectively a hydrogen atom, a methyl group or a methoxy group or

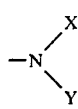
(2)

wherein X and Y may be the same or different from each other and represent respectively a hydrogen atom, a phenyl group, a cyclohexyl group, a methylphenyl group, a fluorophenyl group, a chlorophenyl group, a bromophenyl group, a 3-trifluoromethylphenyl group, a 4-trifluoromethylphenyl group, a 3-nitrophenyl group, a 3-methoxycarbonylphenyl group, a 4-methoxycarbonylphenyl group, a methoxyphenyl group, a 4-benzoylphenyl group, a 4-acetylphenyl group, a benzyl group, a benzyloxy group,

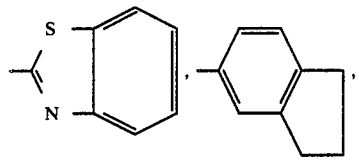

-continued

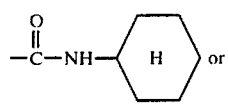

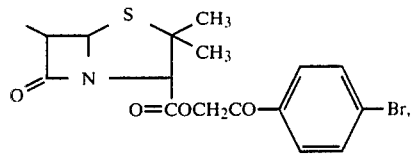

and a pharmaceutically acceptable carrier.

8. A pharmaceutical composition having antibacterial activity, antifungal activity or antimycoplasmal activity in dosage unit form which comprises a dosage effective to produce the activities of a derivative of β-(4-isocyano-1,2-3,4-diepoxy-cyclopentyl)acrylic acid represented by formula (I):

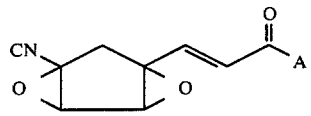
(I)

wherein A represents

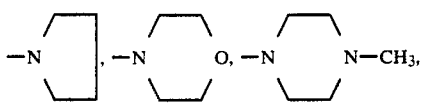

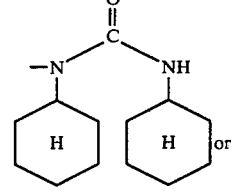

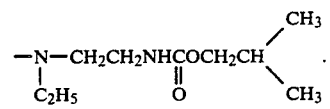

* * * * *